US012364750B1

(12) United States Patent
Korber et al.

(10) Patent No.: US 12,364,750 B1
(45) Date of Patent: Jul. 22, 2025

(54) CONSERVED REGION T CELL VACCINES FOR CORONAVIRUS AND METHODS OF USE

(71) Applicants: Triad National Security, LLC, Los Alamos, NM (US); The Trustees of The University of Pennsylvania, Philadelphia, PA (US); Beth Israel Deaconess Medical Center, Inc., Boston, MA (US); Oxford University Innovation Limited, Oxford (GB)

(72) Inventors: Bette T. M. Korber, Los Alamos, NM (US); James Theiler, Los Alamos, NM (US); Dan Barouch, Boston, MA (US); Drew Weissman, Philadelphia, PA (US); Tomas Hanke, Oxford (GB)

(73) Assignees: Triad National Security, LLC, Los Alamos, NM (US); Oxford University Innovation Limited, Oxford (GB); The Trustees of the University of Pennsylvania, Philadelphia, PA (US); Beth Israel Deaconess Medical Center, Inc., Boston, MA (US)

(*) Notice: Subject to any disclaimer, the term of this patent is extended or adjusted under 35 U.S.C. 154(b) by 0 days.

(21) Appl. No.: 18/670,452

(22) Filed: May 21, 2024

Related U.S. Application Data

(62) Division of application No. 17/234,590, filed on Apr. 19, 2021, now Pat. No. 12,023,376.

(60) Provisional application No. 63/011,816, filed on Apr. 17, 2020.

(51) Int. Cl.

| | | |
|---|---|---|
| *A61K 39/215* | (2006.01) | |
| *A61K 9/51* | (2006.01) | |
| *A61K 48/00* | (2006.01) | |
| *A61P 31/14* | (2006.01) | |
| *C07K 14/005* | (2006.01) | |
| *C12N 7/00* | (2006.01) | |
| *C12N 9/12* | (2006.01) | |
| *C12N 9/14* | (2006.01) | |
| *C12N 15/86* | (2006.01) | |
| *A61K 39/00* | (2006.01) | |

(52) U.S. Cl.
CPC .......... *A61K 39/215* (2013.01); *A61K 9/5123* (2013.01); *A61P 31/14* (2018.01); *C07K 14/005* (2013.01); *C12N 7/00* (2013.01); *C12N 9/127* (2013.01); *C12N 9/14* (2013.01); *C12N 15/86* (2013.01); *C12Y 207/07048* (2013.01); *C12Y 306/04013* (2013.01); *A61K 2039/5254* (2013.01); *A61K 2039/53* (2013.01); *A61K 48/00* (2013.01); *C12N 2750/14143* (2013.01); *C12N 2770/18022* (2013.01); *C12N 2770/18034* (2013.01)

(58) Field of Classification Search
None
See application file for complete search history.

(56) References Cited

U.S. PATENT DOCUMENTS

| | | |
|---|---|---|
| 9,670,152 B2 | 6/2017 | Payne et al. |
| 10,221,127 B2 | 3/2019 | Du et al. |
| 2019/0175716 A1 | 6/2019 | Gilbert et al. |
| 2020/0155691 A1 | 5/2020 | Derosa et al. |

FOREIGN PATENT DOCUMENTS

| | | |
|---|---|---|
| WO | WO 2017/075531 | 5/2017 |
| WO | WO 2020/214946 | 10/2020 |
| WO | WO 2020/219941 | 10/2020 |

OTHER PUBLICATIONS

Gao W, Tamin A, Soloff A, D'Aiuto L, Nwanegbo E, Robbins PD, Bellini WJ, Barratt-Boyes S, Gambotto A. Effects of a SARS-associated coronavirus vaccine in monkeys. Lancet. Dec. 6, 2003;362(9399):1895-6. doi: 10.1016/S0140-6736(03)14962-8. PMID: 14667748; PMCID: PMC7112457. (Year: 2003).*
Lau, et al. Proc Natl Acad Sci U S A. Sep. 27, 2005;102(39):14040-5. doi: 10.1073/pnas.0506735102. Epub Sep. 16, 2005. PMID: 16169905. (Year: 2005).*
EMBL; DQ022305 (Year: 2005).*
Genbank accession QHR63259.1 Mar. 18, 2020. (Year: 2020).*
Pardi and Weissman. Abstract, Methods Mol Biol. 2017;1499:109-121. doi: 10.1007/978-1-4939-6481-9_6. PMID: 27987145. (Year: 2017).*
Dicks et al., "A Novel Chimpanzee Adenovirus Vector with Low Human Seroprevalence: Improved Systems for Vector Derivation and Comparative Immunogenicity," *PloS One*, 7(77): e40385, 12 pages, 2012.
Gao et al., "Effects of a SARS-associated coronavirus vaccine in monkeys," *Lancet*, 362(9399): 1895-1896, 2003.
GenBank accession NC_045512.2 (Mar. 30, 2020), 2020.
Hassett et al., "Optimization of Lipid Nanoparticles for Intramuscular Administration of mRNA Vaccines," *Molecular Therapy: Nucleic Acids*, 15: 1-11, 2019.
Li et al., "Emergence of SARS-CoV-2 through recombination and strong purifying selection," *Scientific Advances.*, 6(27): eabb9153, 11 pages, 2020.
Moghimi et al., "Allergic Reactions and Anaphylaxis to LNP-Based COVID-19 Vaccines," *Molecular Therapy*, 29(3): 898-900, 2021.

(Continued)

*Primary Examiner* — Benjamin P Blumel
*Assistant Examiner* — Jeffrey Mark Sifford
(74) *Attorney, Agent, or Firm* — Klarquist Sparkman, LLP

(57) ABSTRACT

Immunogenic compositions and methods of their use in eliciting immune responses to coronaviruses, such as SARS-CoV-2 are provided.

20 Claims, 25 Drawing Sheets
Specification includes a Sequence Listing.

(56) References Cited

OTHER PUBLICATIONS

Ondondo et al., "Novel Conserved-region T-cell Mosaic Vaccine With High Global HIV-1 Coverage Is Recognized by Protective Responses in Untreated Infection," *Molecular Therapy*, 24(4): 832-842, 2016.

Pardi et al., "Characterization of HIV-1 Nucleoside-Modified mRNA Vaccines in Rabbits and Rhesus Macaques," *Molecular Therapy: Nucleic Acids*, 15: 36-47, 2019.

Pardi et al., "Nucleoside-modified mRNA immunization elicits influenza virus hemagglutinin stalk-specific antibodies," *Nature Communications*, 9: 3361, 12 pages, 2018.

Teigler et al., "Vaccination with adenovirus serotypes 35, 26, and 48 elicits higher levels of innate cytokine responses then adenovirus serotype 5 in rhesus monkeys," *Journal of Virology*, 86(18): 9590-9598, 2012.

Theiler and Korber, "Graph-based optimization of epitope coverage for vaccine antigen design," *Statistics in Medicine*, 37: 181-194, 2018.

Theiler et al., "Epigraph: A Vaccine Design Tool Applied to an HIV Therapeutic Vaccine and a Pan-Filovirus Vaccine," *Scientific Reports*, 6: 33987, 15 pages, 2016.

\* cited by examiner

WB with 336 (α-Pk)

Coomassie-stained kDa: 268, 238, 171, 117, 71, 55

1. ChAdOx1.COVconsv-infected HeLa lysate
2. ChAdOx2.COVconsv-infected HeLa lysate
3. Uninfected HeLa lysate FIG. 8A
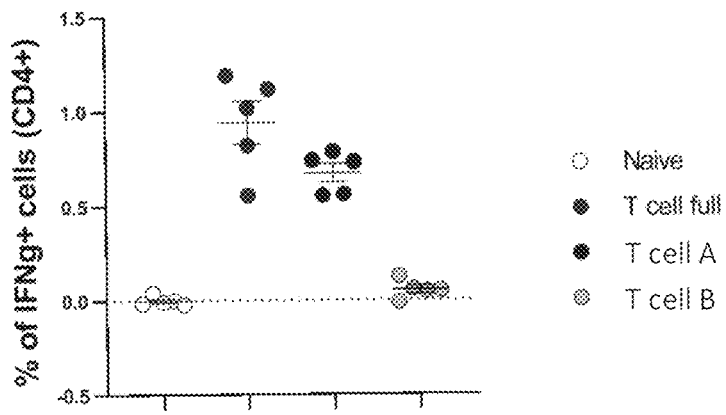
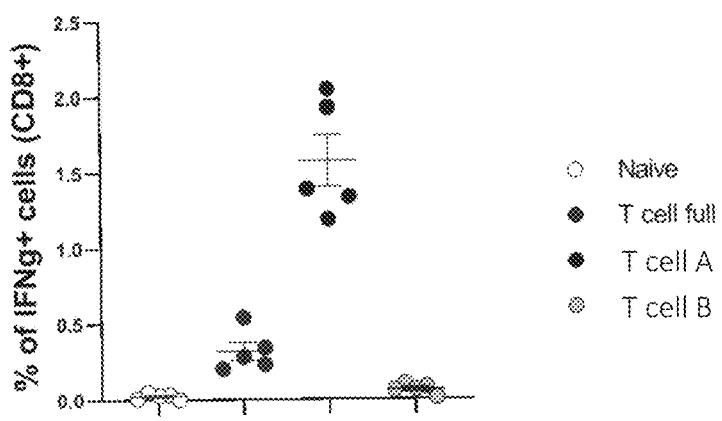
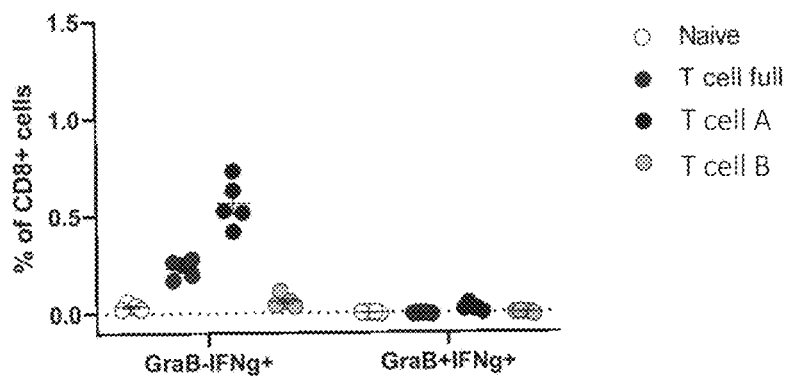

FIG. 8B
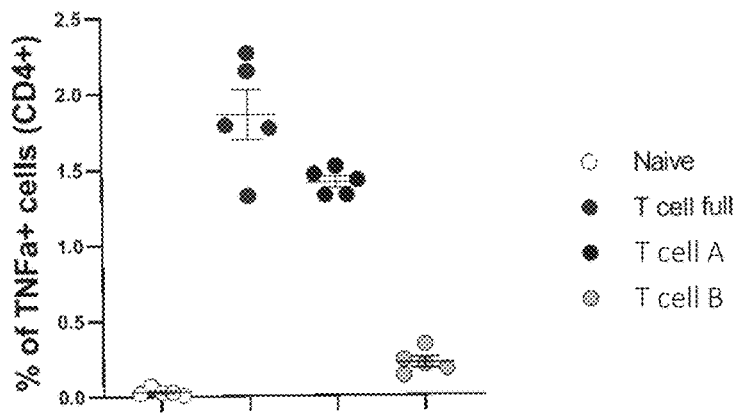
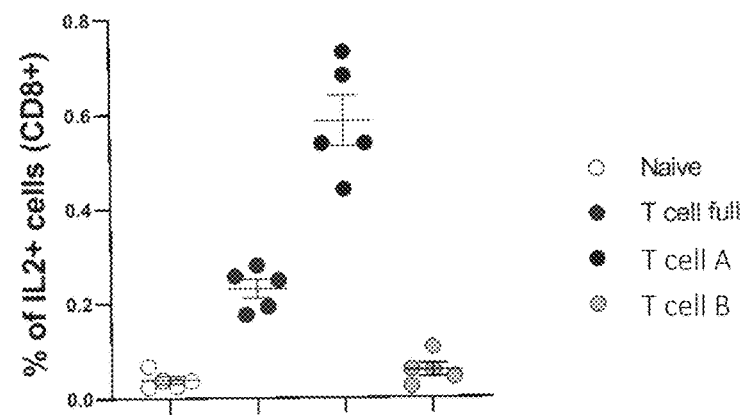
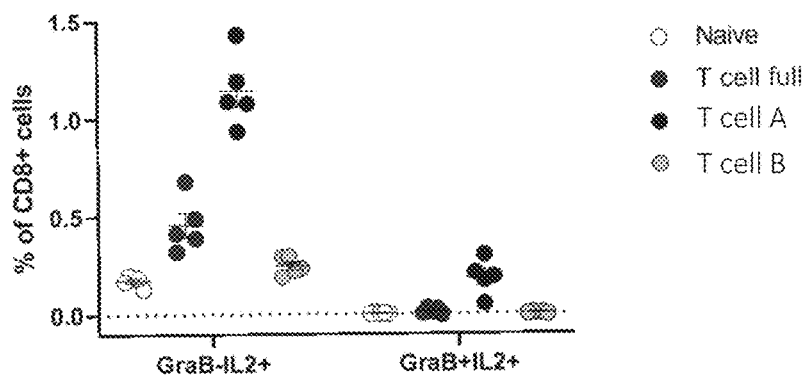

FIG. 8C
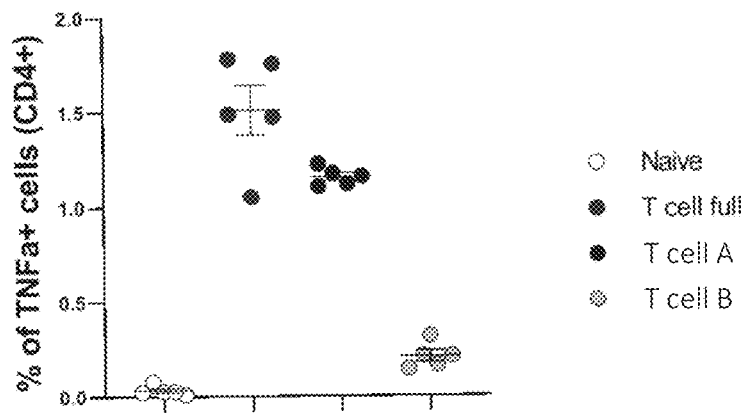
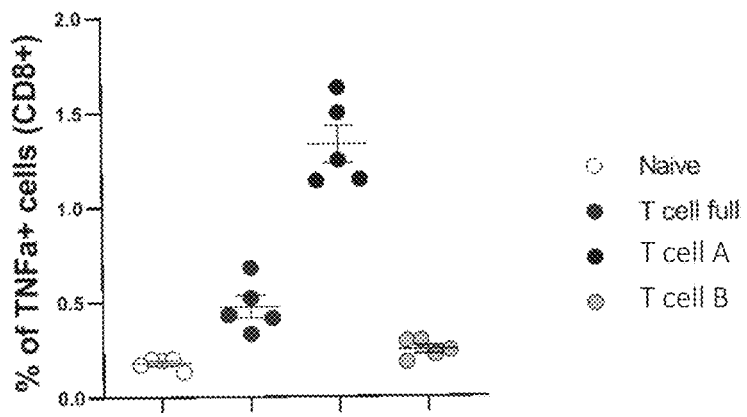
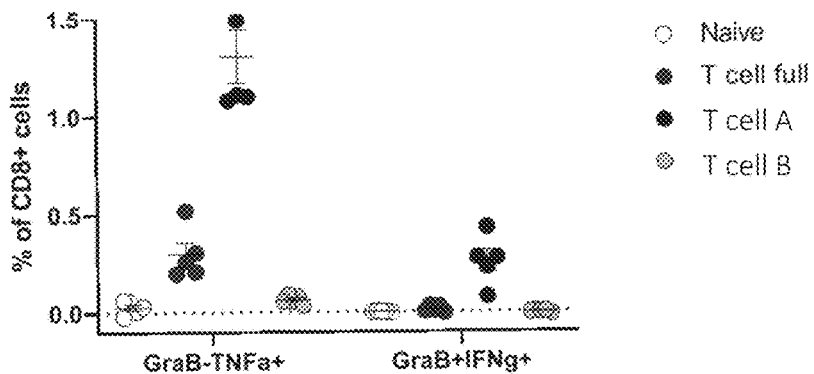

FIG. 8D
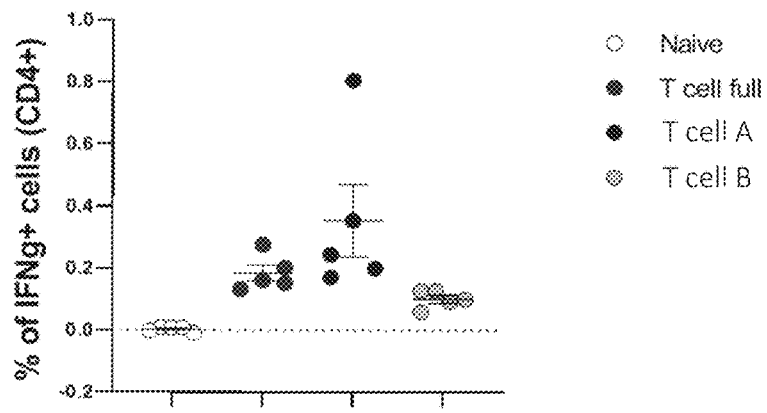
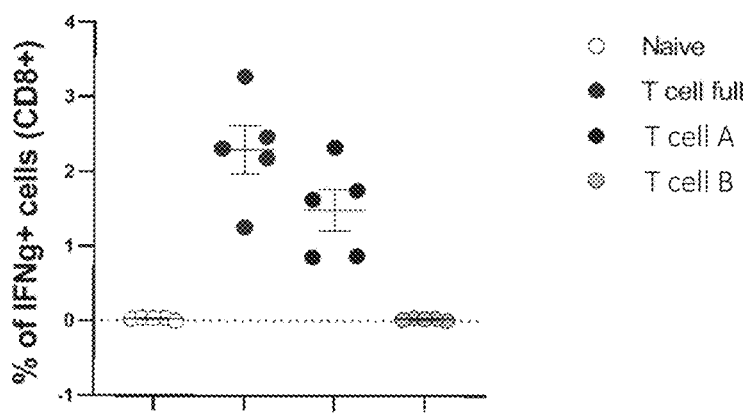
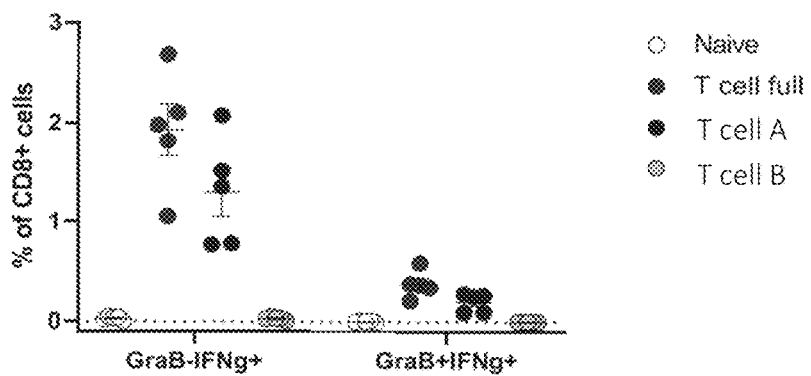

FIG. 8E
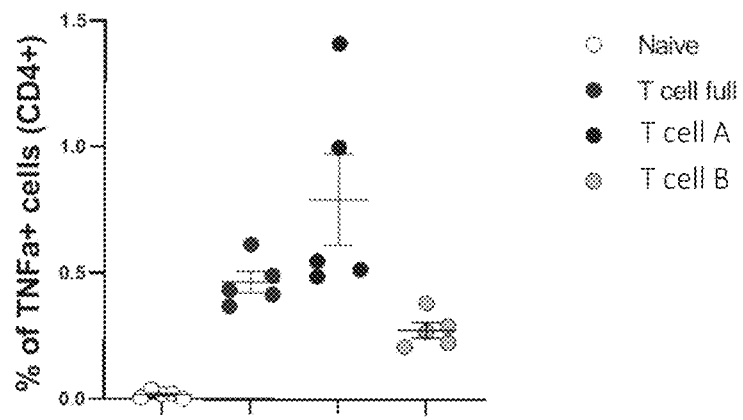
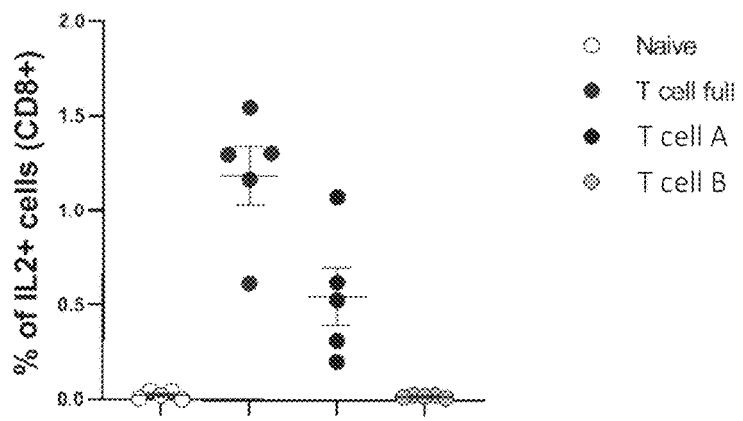
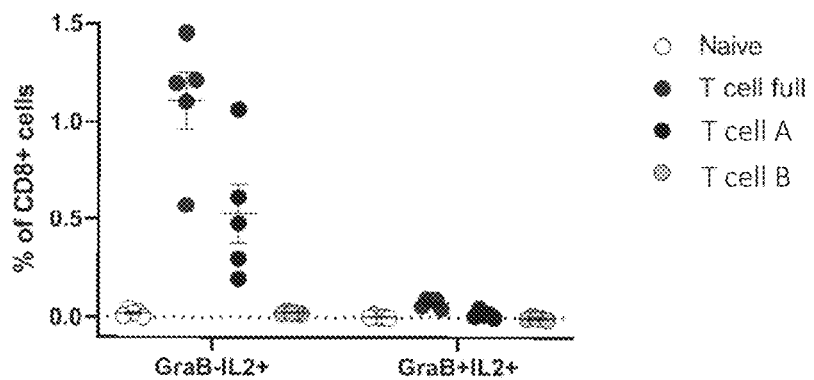

FIG. 8F
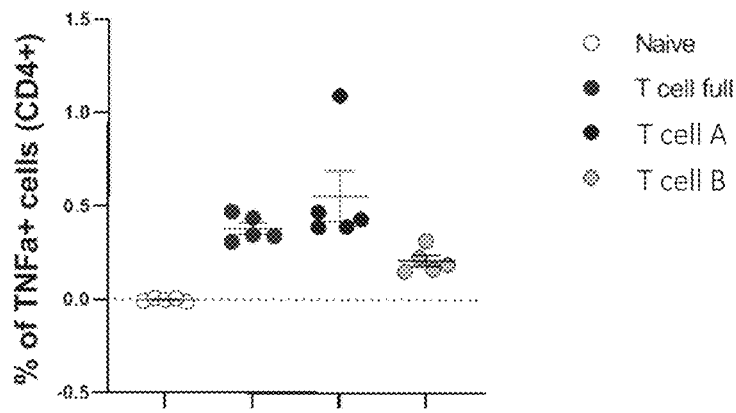
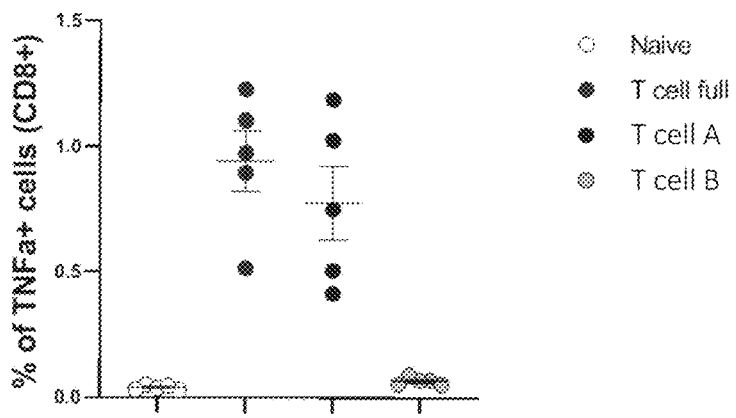
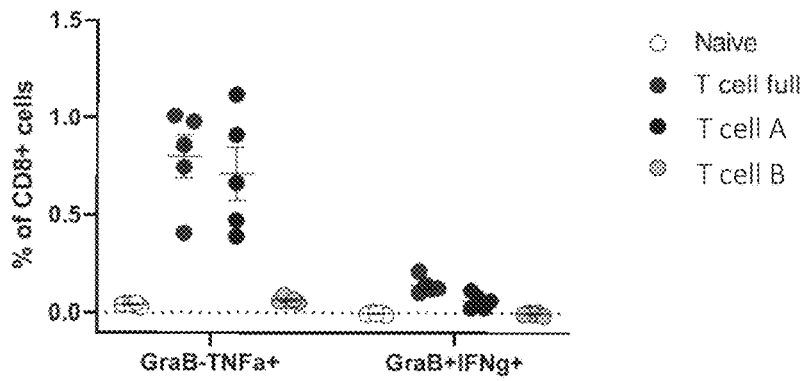

FIG. 11

```
       NC_045512 NCLDDRCILHCANFNVLFSTVFPPTSFGPLVRKIFVDGVPFVVSTGYHFRELGVVHNQDV   60
    Region-1-EG-2.1 --S---------S------------L----------M---------I-------------L-----
    Region-1-EG-2.2 --------V---------------F----------C--------------H---------Y----

NC_045512 NLHSSRLSFKELLVYAADPAMHAASGNLLLDKRTTCFSVAALTNNVAFQTVKPGNFNKDF  120
    Region-1-EG-2.1 ---------N-----------T------------M-----------------R---------
    Region-1-EG-2.2 ----F--------L---------V---------R--------------F------------

NC_045512 YDFAVSKGFFKEGSSVELKHFFFAQDGNAAISDYDYYRYNLPTMCDIRQLLFVVEVVDKY  180
    Region-1-EG-2.1 ----V-----------F-----------V------------I----------------N-
    Region-1-EG-2.2 ----L-----------P---------V----------E---------F-------F-----

NC_045512 FDCYDGGCINANQVIVNNLDKSAGFPFNKWGKARLYYDSMSYEDQDALFAYTKRNVIPTI  240
    Region-1-EG-2.1 ------------S---------------------F----------------V--------
    Region-1-EG-2.2 -------------T--------------------E----------V--------T----

NC_045512 TQMNLKYAISAKNRARTVAGVSICSTMTNRQFHQKLLKSIAATRGATVVIGTSKFYGGWH  300
    Region-1-EG-2.1 ---------------S---------F---------Y----------S---------I-----
    Region-1-EG-2.2 -----------V-------------I-----------------G------------------

NC_045512 NMLKTVYSDVENPHLMGWDYPKCDRAMPNMLRIMASLVLARKHTTCCSLSHRFYRLANEC  360
    Region-1-EG-2.1 ------I-------F-------------I---------F--------I---------S----
    Region-1-EG-2.2 -I--------Y-------------------V---------M---------T----

NC_045512 AQVLSEMVMCGGSLYVKPGGTSSGDATTAYANSVFNICQAVTANVNALLSTDGNKIADKY  420
    Region-1-EG-2.1 ------I------------------E----------------S---------------------
    Region-1-EG-2.2 ---------I-------------------------F---------T-----------N-

NC_045512 VRNLQHRLYECLYRNRDVDTDFVNEFYAYLRKHFSMMILSDDAVVCFNSTYASQGLVASI  480
    Region-1-EG-2.1 I---------A----------I-----------I-----------V---------L----
    Region-1-EG-2.2 ---------G---------Y---------T---------I-------------V---------

NC_045512 KNFKSVLYYQNNVFMSEAKCWTETDLTKGPHEFCSQHTMLVKQGDDYVYLPYPDPSRILG  540
    Region-1-EG-2.1 ---------I---------I-----------H---------S--------
    Region-1-EG-2.2 R-----------------V---------I----------I---------F---

NC_045512 AGCFVDDIVKTDGTLMIERFVSLAIDAYPLTKHPNQEYADVFHLYLQYIRKLHDELTGHM  600
    Region-1-EG-2.1 --------L-----------------I------------R------------Y------
    Region-1-EG-2.2 -------V---------V-------------F----------Y---------K---------I NC_045512 LDMYSVMLTNDNTSRYWEPEFYEAMYTPHTVLQAVGACVLCNSQTSLRCGACIRRPFLCC  660
    Region-1-EG-2.1 --I---------L--------D--------------V-------------V------
    Region-1-EG-2.2 ---------I---------S---------S---------S---------L-------K------

NC_045512 KCCYDHVISTSHKLVLSVNPYVCNAPGCDVTDVTQLYLGGMSYYCKSHKPPISFPLCANG  720
    Region-1-EG-2.1 E---------L-----------L-----------N---------S----------
    Region-1-EG-2.2 ---------I---------F-------V-------------C----------P-----------V---

NC_045512 QVFGLYKNTCVGSDNVTDFNAIATCDWTNAGDYILANTCTERLKLFAAETLKATEETFKL  780
    Region-1-EG-2.1 H---------F--------------I---------I---------I--------
    Region-1-EG-2.2 ---------A------------S--------------A----------M---------

NC_045512 SYGIATVREVLSDRELHLSWEVGKPRPPLNRNYVFTGYRVTKNSKVQIGEYTFEKGDYGD  840
    Region-1-EG-2.1 ------I---------Y----------F----------L---------D---------V-
    Region-1-EG-2.2 ----V---------K---------R----------H----------T---------Y----

NC_045512 AVVYRGTTTYKLNVGDYFVLTSHTVMPLSAPTLVPQEHYVRITGLYPTLNISDEFSSNVA  900
    Region-1-EG-2.1 -----------R-----------I---------D------------D-------
    Region-1-EG-2.2 -------I---------L-----------I---------I---------Y---------
```

FIG. 11 (cont.)

```
      NC_045512  NYQKVGMQKYSTLQGPPGTGKSHFAIGLALYYPSARIVYTACSHAAVDALCEKALKYLPI   960
   Region-1-EG-2.1  ------I----------------Y---------L----------------YT--------F-
   Region-1-EG-2.2  ---------R--------------------S---------M---------------D---------

NC_045512  DKCSRIIPARARVECFDKFKVNSTLEQYVFCTVNALPETTADIVVFDEISMATNYDLSVV  1020
   Region-1-EG-2.1  --------------D----------L---------------D---------------T---------
   Region-1-EG-2.2  ------------L----------L----------------------V---------T---------

NC_045512  NARLRAKHYVYIGDPAQLPAPRTLLTKGTLEPEYFNSVCRLMKTIGPDMFLGTCRRCPAE  1080
   Region-1-EG-2.1  ----C----------S------------I---------F-------------------S-
   Region-1-EG-2.2  -V----------V----------------I---------------I----------R---------

NC_045512  IVDTVSALVYDNKL  1094
   Region-1-EG-2.1  -------------R-
   Region-1-EG-2.2  ----L----------
```

FIG. 13

```
           NC_045512  NCLDDRCILHCANFNVLFSTVFPPTSFGPLVRKIFVDGVPFVVSTGYHFRELGVVHNQDV   60
   SARBECO-CoV-2-EG-3.1  -----------------------------L------------------------------
   SARBECO-CoV-2-EG-3.2  ------------------------------------------------------------

NC_045512  NLHSSRLSFKELLVYAADPAMHAASGNLLLDKRTTCFSVAALTNNVAFQTVKPGNFNKDF  120
   SARBECO-CoV-2-EG-3.1  -I-------------------------------------S--------------------
   SARBECO-CoV-2-EG-3.2  -I-------------------------------------S--------------------

NC_045512  YDFAVSKGFFKEGSSVELKHFFAQDGNAAISDYDYYRYNLPTMCDIRQLLFVVEVVDKY   180
   SARBECO-CoV-2-EG-3.1  ------------------------------------------------------------
   SARBECO-CoV-2-EG-3.2  ------------------------------------------------------------

NC_045512  FDCYDGGCINANQVIVNNLDKSAGFPFNKWGKARLYYDSMSYEDQDALFAYTKRNVIPTI  240
   SARBECO-CoV-2-EG-3.1  ----------------------------------------------------------L---
   SARBECO-CoV-2-EG-3.2  ----------------------------------------------------------L---

NC_045512  TQMNLKYAISAKNRARTVAGVSICSTMTNRQFHQKLLKSIAATRGATVVIGTSKFYGGWH  300
   SARBECO-CoV-2-EG-3.1  -----------------------------------------------------------N
   SARBECO-CoV-2-EG-3.2  -----------------------------------------------------------N

NC_045512  NMLKTVYSDVENPHLMGWDYPKCDRAMPNMLRIMASLVLARKHTTCCSLSHRFYRLANEC  360
   SARBECO-CoV-2-EG-3.1  -------T------------------------------S---N-----------------
   SARBECO-CoV-2-EG-3.2  -------S----------------------------------N---N-------------

NC_045512  AQVLSEMVMCGGSLYVKPGGTSSGDATTAYANSVFNICQAVTANVNALLSTDGNKIADKY  420
   SARBECO-CoV-2-EG-3.1  ----------------------------------------------------G-------
   SARBECO-CoV-2-EG-3.2  ------------------------------------------------------------

NC_045512  VRNLQHRLYECLYRNRDVDTDFVNEFYAYLRKHFSMMILSAAAVVCFNSTYASQGLVASI  480
   SARBECO-CoV-2-EG-3.1  I-------------HE--D-------------------------Y--N--A---------
   SARBECO-CoV-2-EG-3.2  --------------------------------------------Y--N--A---------

NC_045512  KNFKSVLYYQNNVFMSEAKCWTETDLTKGPHEFCSQHTMLVKQGDDYVYLPYPDPSRILG  540
   SARBECO-CoV-2-EG-3.1  ----A-------------------R-----------------------------------
   SARBECO-CoV-2-EG-3.2  ------------------------R-----------------------------------

NC_045512  AGCFVDDIVKTDGTLMIERFVSLAIDAYPLTKHPNQEYADVFHLYLQYIRKLHDELTGHM  600
   SARBECO-CoV-2-EG-3.1  ------------------------------------------------------------
   SARBECO-CoV-2-EG-3.2  ------------------------------------------------------------

NC_045512  LDMYSVMLTNDNTSRYWEPEFYEAMYTPHTVLQAVGACVLCNSQTSLRCGACIRRPFLCC  660
   SARBECO-CoV-2-EG-3.1  ------------S------------------I----------------------------
   SARBECO-CoV-2-EG-3.2  ------------------------------------------------------------

NC_045512  KCCYDHVISTSHKLVLSVNPYVCNAPGCDVTDVTQLYLGGMSYYCKSHKPPISFPLCANG  720
   SARBECO-CoV-2-EG-3.1  -----------------T-------------------A----------------------
   SARBECO-CoV-2-EG-3.2  -----------------------------------------L------------------

NC_045512  QVFGLYKNTCVGSDNVTDFNAIATCDWTNAGDYILANTCTERLKLFAAETLKATEETFKL  780
   SARBECO-CoV-2-EG-3.1  ------------------------------------------------------------
   SARBECO-CoV-2-EG-3.2  ------------------------------------------------------------
```

FIG. 13 (cont.)

```
         NC_045512  SYGIATVREVLSDRELHLSWEVGKPRPPLNRNYVFTGYRVTKNSKVQIGEYTFEKGDYGD  840
SARBECO-CoV-2-EG-3.1  -------------------Y------------------------T---------------
SARBECO-CoV-2-EG-3.2  ------------------------------------------------------------

NC_045512  AVVYRGTTTYKLNVGDYFVLTSHTVMPLSAPTLVPQEHYVRITGLYPTLNISDEFSSNVA  900
SARBECO-CoV-2-EG-3.1  ---------------------------------------------------E--------
SARBECO-CoV-2-EG-3.2  ------------------------------------------------------------

NC_045512  NYQKVGMQKYSTLQGPPGTGKSHFAIGLALYYPSARIVYTACSHAAVDALCEKALKYLPI  960
SARBECO-CoV-2-EG-3.1  ----I-------------------------------------------------------
SARBECO-CoV-2-EG-3.2  ----I-------------------------------------------------------

NC_045512  DKCSRIIPARARVECFDKFKVNSTLEQYVFCTVNALPETTADIVVFDEISMATNYDLSVV  1020
SARBECO-CoV-2-EG-3.1  ------------------------------------------------------------
SARBECO-CoV-2-EG-3.2  ------------------------------------------------------------

NC_045512  NARLRAKHYVYIGDPAQLPAPRTLLTKGTLEPEYFNSVCRLMKTIGPDMFLGTCRRCPAE  1080
SARBECO-CoV-2-EG-3.1  ------------------------------------------------------------
SARBECO-CoV-2-EG-3.2  ------------------------------------------------------------

NC_045512  IVDTVSALVYDNKL  1094
SARBECO-CoV-2-EG-3.1  --------------
SARBECO-CoV-2-EG-3.2  --------------
```

FIG. 15

```
         NC_045512  GGKPCIKVATVQSKMSDVKCTSVVLLSVLQQLRVESSSKLWAQCVQLHNDILLAKDTTEA   60
      Region-2-EG-2.1  ------V--------I------------L-----------L----------------I---------
      Region-2-EG-2.2  -------------T----------F---------F--------------R--------

NC_045512  FEKMVSLLSVLLSMQGAVDINKLCEEMLDNRATLQAIASEFSSLPSYAAFATAQEAYEQA  120
      Region-2-EG-2.1  -G--------------R----------I---------S---------S-------------R-
      Region-2-EG-2.2  -------------F----------F---------I-------------------L---------

NC_045512  VANGDSEVVLKKLKKSLNVAKSEFDRDAAMQRKLEKMADQAMTQMYKQARSEDKRAKVTS  180
      Region-2-EG-2.1  --------F--------------C-----------N----------V-----------
      Region-2-EG-2.2  -V-----------N--------------L------------S----------K--------I-

NC_045512  AMQTMLFTMLRKLDNDALNNIINNARDGCVPLNIIPLTTAAKLMVVIPDYNTYKNTCDGT  240
      Region-2-EG-2.1  ---I----------F----------V---------------F----------S------------I
      Region-2-EG-2.2  -----------F----------D----------------I---------T---------M-----

NC_045512  TFTYASALWEIQQVVDADSKIVQLSEISMDNSPNLAWPLIVTALRANSAVKLQNNELSPV  300
      Region-2-EG-2.1  --------------H----------F---------S-------I---------------------
      Region-2-EG-2.2  --I--------------N----------V-------------V----------I---------I NC_045512  ALRQMSCAAGTTQTACTDDNALAYYNTTKGGRFVLALLSDLQDLKWARFPKSDGTGTIYT  360
      Region-2-EG-2.1  V-------------I-------------I----------------N-------------------V--
      Region-2-EG-2.2  -------------I---------V--------F------------------S----------I NC_045512  ELEPPCRFVTDTPKGPKVKYLYFIKGLNNLNRGMVLGSLAATVRLQAGNATEVPANSTVL  420
      Region-2-EG-2.1  ------G--------L----------R---------I----------K---------I-
      Region-2-EG-2.2  -------------L----------R------------I----------I----------

NC_045512  SFCAFAVDAAKAYKDYLASGGQPITNCVKMLCTHTGTGQAITVTPEANMDQESFGGASCC  480
      Region-2-EG-2.1  -------I---------V--------------I--------I------------------
      Region-2-EG-2.2  F--------S---------------I------------I----------E--------

NC_045512  LYCRCHIDHPNPKGFCDLKGKYVQIPTTCANDPVGFTLKNTVCTVCGMWKGYGCSCDQLR  540
      Region-2-EG-2.1  M-----------D----------------I---------I--------S------------C
      Region-2-EG-2.2  ------------S----------R---------V-------------I---------G-------
```

FIG. 16

```
NC_045512  GGKPCIKVATVQSKMSDVKCTSVVLLSVLQQLRVESSSKLWAQCVQLHNDILLAKDTTEA   60
EG-1       ------------------------------------------------------------
EG-2       ------------------------------------------------------------

NC_045512  FEKMVSLLSVLLSMQGAVDINKLCEEMLDNRATLQAIASEFSSLPSYAAFATAQEAYEQA  120
EG-1       -----------------------R------------------------Y-----------
EG-2       -----------------------R------------------------------------

NC_045512  VANGDSEVVLKKLKKSLNVAKSEFDRDAAMQRKLEKMADQAMTQMYKQARSEDKRAKVTS  180
EG-1       -S------------------------H---------------------------------
EG-2       ------------------------------------------------------------

NC_045512  AMQTMLFTMLRKLDNDALNNIINNARDGCVPLNIIPLTTAAKLMVVIPDYNTYKNTCDGT  240
EG-1       --------------------------------------------V----G-------N--
EG-2       ---------------------------------------------V----------E-S

NC_045512  TFTYASALWEIQQVVDADSKIVQLSEISMDNSPNLAWPLIVTALRANSAVKLQNNELSPV  300
EG-1       -----------------------N------------------------------------
EG-2       ------------------P----N----Q-------------------------------

NC_045512  ALRQMSCAAGTTQTACTDDNALAYYNTTKGGRFVLALLSDLQDLKWARFPKSDGTGTIYT  360
EG-1       ----------------NE---------NS-------------H-----------------
EG-2       ----------------S-------------------------------------------

NC_045512  ELEPPCRFVTDTPKGPKVKYLYFIKGLNNLNRGMVLGSLAATVRLQAGNATEVPANSTVL  420
EG-1       ------------------------------------------------------------
EG-2       ------------------------------------------------------------

NC_045512  SFCAFAVDAAKAYKDYLASGGQPITNCVKMLCTHTGTGQAITVTPEANMDQESFGGASCC  480
EG-1       ----------P---------S---------------------------------------
EG-2       ---------S---R----------------------------------------------

NC_045512  LYCRCHIDHPNPKGFCDLKGKYVQIPTTCANDPVGFTLKNTVCTVCGMWKGYGCSCDQLR  540
EG-1       ---------------Y-E------------------R-----------------------
EG-2       ------------------------------------R-----------------------
```

CONSERVED REGION T CELL VACCINES FOR CORONAVIRUS AND METHODS OF USE

CROSS REFERENCE TO RELATED APPLICATIONS

This application is a divisional of U.S. application Ser. No. 17/234,590, filed Apr. 19, 2021, which in turns claims the benefit of U.S. Provisional Application No. 63/011,816, filed Apr. 17, 2020, both of which are incorporated herein by reference in their entireties.

ACKNOWLEDGMENT OF GOVERNMENT SUPPORT

This invention was made with government support under Contract No. 89233218CNA000001 awarded by the U.S. Department of Energy/National Nuclear Security Administration. The government has certain rights in the invention.

FIELD

This disclosure relates to conserved region T cell vaccines for coronaviruses, particularly SARS-CoV-2, and methods of use.

INCORPORATION OF SEQUENCE LISTING

The Sequence Listing is submitted as an XML file named "Sequence.xml" which was created on May 20, 2024, and is 40,354 bytes, which is incorporated by reference herein.

BACKGROUND

COVID-19 is a severe respiratory disease first reported in China in late December 2019. Severe acute respiratory syndrome coronavirus 2 (SARS-CoV-2) is the etiological agent of COVID-19, and is a new member of the diverse genus Betacoronavirus. It rapidly became epidemic in China, spread globally, and has had an unparalleled and devastating impact on humanity. Three factors combine to make this disease so dangerous: human beings have no immunological experience with this virus, leaving us vulnerable to infection; it is highly transmissible (estimates for $R_0$ range between 2-5); and it has a high mortality rate (estimates range between 0.5-5%).

SUMMARY

Provided herein are immunogenic compositions and methods of their use in eliciting immune responses to coronaviruses, such as SARS-CoV-2.

Methods of eliciting an immune response to a coronavirus in a subject are provided. In some embodiments, the methods include administering to the subject a composition comprising one or more polypeptides with at least 95% sequence identity (such as at least 99% sequence identity) to any one of SEQ ID NOs: 1-14 and 18 or a composition comprising one or more nucleic acids encoding one or more polypeptides with at least 95% sequence identity (such as at least 99% sequence identity) to any one of SEQ ID NOs: 1-14 and 18, thereby eliciting an immune response to the coronavirus. In some examples, the one or more polypeptides include or consist of the amino acid sequence of any one of SEQ ID NOs: 1-14 and 18.

In some embodiments, the methods include administering to the subject one or more (such as 1, 2, 3, or more) of the polypeptides, or one or more nucleic acids (such as 1, 2, 3, or more) nucleic acids encoding the polypeptides. In particular examples, the methods include administering to the subject the following polypeptides (or nucleic acids encoding the following polypeptides): SEQ ID NO: 5 and SEQ ID NO: 6; or SEQ ID NO: 5, SEQ ID NO: 6, and SEQ ID NO: 7; or SEQ ID NO: 5 and SEQ ID NO: 8; or SEQ ID NO: 5, SEQ ID NO: 8, and SEQ ID NO: 9; or SEQ ID NO: 10; or SEQ ID NO: 10 and SEQ ID NO: 11; or SEQ ID NO: 10, SEQ ID NO: 11, and SEQ ID NO: 12; or SEQ ID NO: 10 and SEQ ID NO: 13; or SEQ ID NO: 10, SEQ ID NO: 13, and SEQ ID NO: 14.

In particular embodiments, the nucleic acid encoding the one or more polypeptides is mRNA, which in some embodiments is formulated in a lipid nanoparticle. In some non-limiting examples, the lipid nanoparticle is ALC-0315. In other embodiments, the nucleic acid is included in an adenovirus vector administered to the subject. In some examples, the adenovirus vector is an Ad5, Ad26, Ad35, or Ad52 adenovirus vector or a ChAdOx1 or ChAdOx2 adenovirus vector.

Also provided are immunogenic compositions including one or more polypeptides with at least 95% sequence identity (such as at least 99% sequence identity) to any one of SEQ ID NOs: 1-14 and 18 or a nucleic acid encoding a polypeptide with at least 95% sequence identity (such as at least 99% sequence identity) to any one of SEQ ID NOs: 1-14 and 18; and a pharmaceutically acceptable carrier. In some examples, the one or more polypeptides include or consist of the amino acid sequence of any one of SEQ ID NOs: 1-14 and 18.

In some embodiments, the composition includes one or more (such as 1, 2, 3, or more) of the polypeptides, or one or more nucleic acids (such as 1, 2, 3, or more) nucleic acids encoding the polypeptides. In particular examples, the composition includes the following polypeptides (or nucleic acids encoding the following polypeptides): SEQ ID NO: 5 and SEQ ID NO: 6; or SEQ ID NO: 5, SEQ ID NO: 6, and SEQ ID NO: 7; or SEQ ID NO: 5 and SEQ ID NO: 8; or SEQ ID NO: 5, SEQ ID NO: 8, and SEQ ID NO: 9; or SEQ ID NO: 10; or SEQ ID NO: 10 and SEQ ID NO: 11; or SEQ ID NO: 10, SEQ ID NO: 11, and SEQ ID NO: 12; or SEQ ID NO: 10 and SEQ ID NO: 13; or SEQ ID NO: 10, SEQ ID NO: 13, and SEQ ID NO: 14.

In particular embodiments, the composition includes one or more mRNA encoding the one or more polypeptides, which in some embodiments is formulated in a lipid nanoparticle. In some non-limiting examples, the lipid nanoparticle is ALC-0315. Also provided are methods of eliciting an immune response to a coronavirus in a subject, including administering the composition to the subject.

Also provided are vectors including nucleic acids encoding one or more polypeptides with at least 95% sequence identity (such as at least 99% sequence identity) to any one of SEQ ID NOs: 1-14 and 18. In some examples, the vector includes a nucleic acid encoding the amino acid sequence of any one of SEQ ID NOs: 1-14 and 18. In particular examples, the vector is an adenovirus vector, such as an Ad5, Ad26, Ad35, or Ad52 adenovirus vector or a ChAdOx1 or ChAdOx2 vector. Also provided are immunogenic compositions including a disclosed vector and a pharmaceutically acceptable carrier and methods of eliciting an immune response to a coronavirus in a subject, including administering the composition to the subject.

BRIEF DESCRIPTION OF THE DRAWINGS

FIGS. 6A and 6B show expression of conserved region protein SEQ ID NO: 18 in 6wp HeLa cells infected with ChAdOx1.COVconsv or ChAdOx2.COVconsv. Samples were run on 3-8% Tris Acetate gel and analysed by Western blot (FIG. 6A) and Coomassie staining (FIG. 6B). Left panel shows size marker ladder. COVconsv theoretical size=182.57 kDa. Note that COVconsv has a C-terminal tag Pk recognized by monoclonal antibody 336.

FIGS. 8A-8F show T cell cytokine responses from Balb/c (FIG. 8A-8C) and BL/6 (FIG. 8D-8F) immunized with mRNA-LNP vaccines as indicated. "T cell full" includes the nucleic acid of SEQ ID NO: 15; "T cell A" includes the nucleic acid of SEQ ID NO: 16; and "T cell B" includes the nucleic acid of SEQ ID NO: 17. Representative experiments are shown.

FIG. 11 is an alignment of SEQ ID NOs: 1 (NC_045512), 6 (Region-1-EG-2.1), and 7 (Region 1-EG-2.2)

FIG. 13 is an alignment of SEQ ID NOs: 1 (NC_045512), 8 (SARBECO-CoV-2-EG-3.1), and 9 (SARBECO-CoV-2-EG-3.2).

FIG. 15 is an alignment of SEQ ID NO: 10 (NC_045512), 11 (Region-2-EG-2.1), and 12 (Region-2-EG-2.2).

FIG. 16 is an alignment of SEQ ID NO: 10 (NC_045512), 13 (EG-1), and 14 (EG-2).

SEQUENCE LISTING

Figure 1:
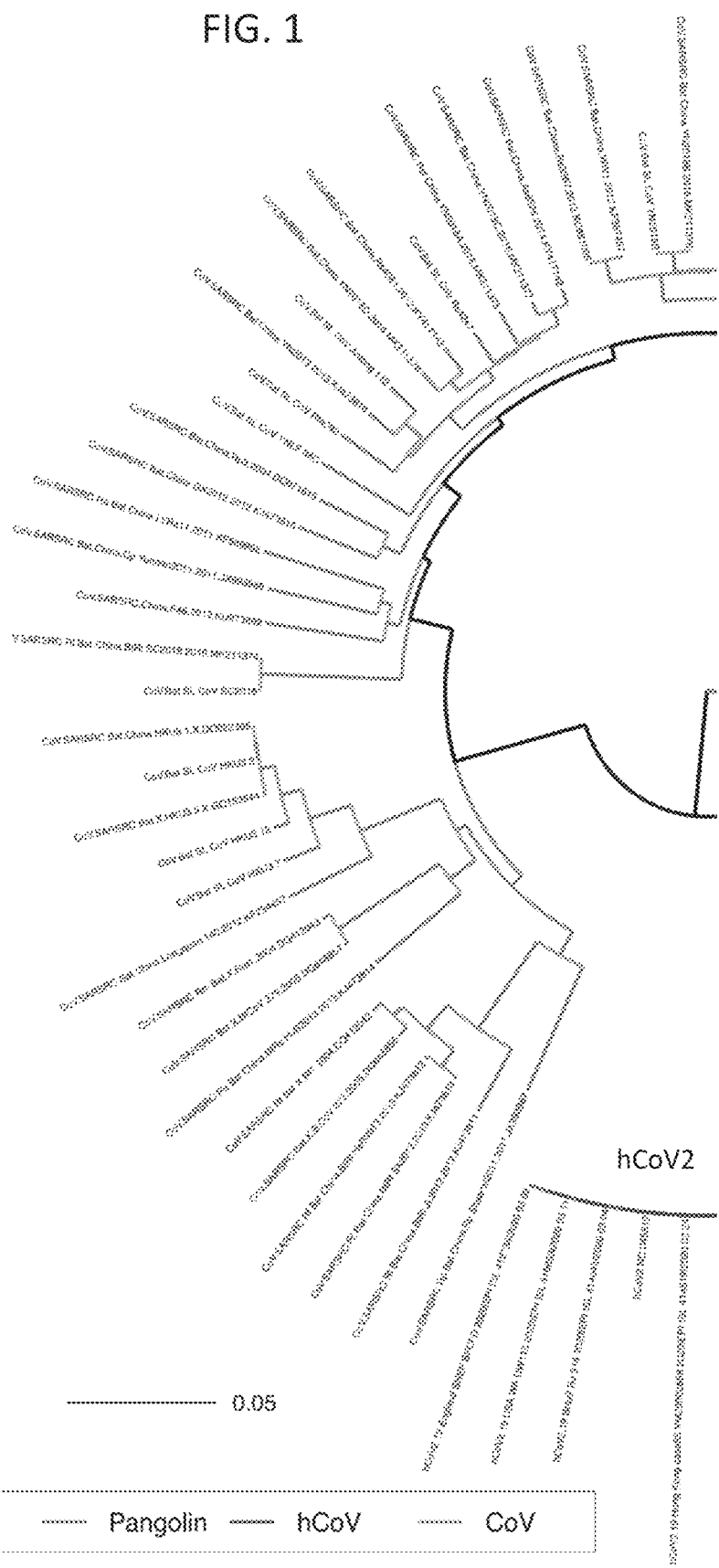
FIG. 1 is a tree illustrating the baseline Sarbecovirus alignment used to define conserved regions. The alignment includes 82 diverse Sarbecoviruses and a single MERS virus, including 49 diverse bat viruses, 14 SARS-CoV-2 pandemic sequences (representative of the sampling available in April 2020), 14 from the SARS-CoV-1 pandemic, and 5 pangolin viruses.
Figure 1:

Any nucleic acid and amino acid sequences provided herein and in the accompanying Sequence Listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

SEQ ID NO: 1 is the amino acid sequence of an exemplary conserved region SARS-CoV-2 polypeptide spanning RNA-dependent RNA polymerase and helicase proteins.

NCLDDRCILHCANFNVLFSTVFPPTSFGPLVRKIFVDGVPFVVSTGYHF

RELGVVHNQDVNLHSSRLSFKELLVYAADPAMHAASGNLLLDKRTTCFS

VAALTNNVAFQTVKPGNFNKDFYDFAVSKGFFKEGSSVELKHFFFAQDG

NAAISDYDYYRYNLPTMCDIRQLLFVVEVVDKYFDCYDGGCINANQVIV

NNLDKSAGFPFNKWGKARLYYDSMSYEDQDALFAYTKRNVIPTITQMNL

KYAISAKNRARTVAGVSICSTMTNRQFHQKLLKSIAATRGATVVIGTSK

FYGGWHNMLKTVYSDVENPHLMGWDYPKCDRAMPNMLRIMASLVLARKH

TTCCSLSHRFYRLANECAQVLSEMVMCGGSLYVKPGGTSSGDATTAYAN

SVFNICQAVTANVNALLSTDGNKIADKYVRNLQHRLYECLYRNRDVDTD

FVNEFYAYLRKHFSMMILSDDAVVCFNSTYASQGLVASIKNFKSVLYYQ

NNVFMSEAKCWTETDLTKGPHEFCSQHTMLVKQGDDYVYLPYPDPSRIL

GAGCFVDDIVKTDGTLMIERFVSLAIDAYPLTKHPNQEYADVFHLYLQY

IRKLHDELTGHMLDMYSVMLTNDNTSRYWEPEFYEAMYTPHTVLQAVGA

CVLCNSQTSLRCGACIRRPFLCCKCCYDHVISTSHKLVLSVNPYVCNAP

GCDVTDVTQLYLGGMSYYCKSHKPPISFPLCANGQVFGLYKNTCVGSDN

VTDFNAIATCDWTNAGDYILANTCTERLKLFAAETLKATEETFKLSYGI

ATVREVLSDRELHLSWEVGKPRPPLNRNYVFTGYRVTKNSKVQIGEYTF

EKGDYGDAVVYRGTTTYKLNVGDYFVLTSHTVMPLSAPTLVPQEHYVRI

TGLYPTLNISDEFSSNVANYQKVGMQKYSTLQGPPGTGKSHFAIGLALY

YPSARIVYTACSHAAVDALCEKALKYLPIDKCSRIIPARARVECFDKFK

```
VNSTLEQYVFCTVNALPETTADIVVFDEISMATNYDLSVVNARLRAKHY

VYIGDPAQLPAPRTLLTKGTLEPEYFNSVCRLMKTIGPDMFLGTCRRCP

AEIVDTVSALVYDNKL
```

SEQ ID NO: 2 is the amino acid sequence of an exemplary conserved region SARS-CoV-2 polypeptide from RNA-dependent RNA polymerase.

FQTVKPGNFNKDFYDFAVSKGFFKEGSSVELKHFF-FAQDGNAAISDYDYYRYNL PTMCDIRQLL-FVVEVVDKYFDCYDGGCI-NANQVIVNNLDKSAGFPFNKWGKARLY YDSMSYEDQDALFAYTKRNVIPTITQMNLKYAI-SAKNRARTVAGVSICSTMTNRQF HQKLLKSIAATR-GATVVIGTSKFYGGWHNMLKTVYSDVE

SEQ ID NO: 3 is the amino acid sequence of an exemplary conserved region SARS-CoV-2 polypeptide from helicase.

EFSSNVANYQKVGMQKYSTLQGPPGTGK-SHFAIGLALYYPSARIVYTACSHAAV DALCEKAL-KYLPIDKCSRIIPARARVECFDKFKVN-STLEQYVFCTVNALPETTADIVV FDEISMATNYDLSVVNARLRAKHYVYIGDPAQLPA-PRTLLTKGTLEPEYFNSVCRLM KTIGPDMFLGT-CRRCPAEIVDTVSALVYDNKL

SEQ ID NO: 4 is the amino acid sequence of an exemplary conserved region SARS-CoV-2 polypeptide spanning nsp6 through nsp10 proteins.

```
GGKPCIKVATVQSKMSDVKCTSVVLLSVLQQLRVESSSKLWAQCVQLHN

DILLAKDTTEAFEKMVSLVLLSMQGAVDINKLCEEMLDNRATLQAIASE

FSSLPSYAAFATAQEAYEQAVANGDSEVVLKKLKKSLNVAKSEFDRDAA

MQRKLEKMADQAMTQMYKQARSEDKRAKVTSAMQTMLFTMLRKLDNDAL

NNIINNARDGCVPLNIIPLTTAAKLMVVIPDYNTYKNTCDGTTFTYASA

LWEIQQVVDADSKIVQLSEISMDNSPNLAWPLIVTALRANSAVKLQNNE

LSPVALRQMSCAAGTTQTACTDDNALAYYNTTKGGRFVLALLSDLQDLK

WARFPKSDGTGTIYTELEPPCRFVTDTPKGPKVKYLYFIKGLNNLNRGM

VLGSLAATVRLQAGNATEVPANSTVLSFCAFAVDAAKAYKDYLASGGQP

ITNCVKMLCTHTGTGQAITVTPEANMDQESFGGASCCLYCRCHIDHPNP

KGFCDLKGKYVQIPTTCANDPVGFTLKNTVCTVCGMWKGYGCSCDQLR
```

SEQ ID NO: 5 is the amino acid sequence of a modified conserved region SARS-CoV-2 polypeptide spanning RNA-dependent RNA polymerase and helicase proteins (Region 1), including a polymerase inactivating mutation (SDD to SAA at amino acids 464-466).

```
NCLDDRCILHCANFNVLFSTVFPPTSFGPLVRKIFVDGVPFVVSTGYHF

RELGVVHNQDVNLHSSRLSFKELLVYAADPAMHAASGNLLLDKRTTCFS

VAALTNNVAFQTVKPGNFNKDFYDFAVSKGFFKEGSSVELKHFFFAQDG

NAAISDYDYYRYNLPTMCDIRQLLFVVEVVDKYFDCYDGGCINANQVIV

NNLDKSAGFPFNKWGKARLYYDSMSYEDQDALFAYTKRNVIPTITQMNL

KYAISAKNRARTVAGVSICSTMTNRQFHQKLLKSIAATRGATVVIGTSK

FYGGWHNMLKTVYSDVENPHLMGWDYPKCDRAMPNMLRIMASLVLARKH

TTCCSLSHRFYRLANECAQVLSEMVMCGGSLYVKPGGTSSGDATTAYAN

SVFNICQAVTANVNALLSTDGNKIADKYVRNLQHRLYECLYRNRDVDTD

FVNEFYAYLRKHFSMMILSAAAVVCFNSTYASQGLVASIKNFKSVLYYQ

NNVFMSEAKCWTETDLTKGPHEFCSQHTMLVKQGDDYVYLPYPDPSRIL

GAGCFVDDIVKTDGTLMIERFVSLAIDAYPLTKHPNQEYADVFHLYLQY

IRKLHDELTGHMLDMYSVMLTNDNTSRYWEPEFYEAMYTPHTVLQAVGA

CVLCNSQTSLRCGACIRRPFLCCKCCYDHVISTSHKLVLSVNPYVCNAP

GCDVTDVTQLYLGGMSYYCKSHKPPISFPLCANGQVFGLYKNTCVGSDN

VTDFNAIATCDWTNAGDYILANTCTERLKLFAAETLKATEETFKLSYGI

ATVREVLSDRELHLSWEVGKPRPPLNRNYVFTGYRVTKNSKVQIGEYTF

EKGDYGDAVVYRGTTTYKLNVGDYFVLTSHTVMPLSAPTLVPQEHYVRI

TGLYPTLNISDEFSSNVANYQKVGMQKYSTLQGPPGTGKSHFAIGLALY

YPSARIVYTACSHAAVDALCEKALKYLPIDKCSRIIPARARVECFDKFK

VNSTLEQYVFCTVNALPETTADIVVFDEISMATNYDLSVVNARLRAKHY

VYIGDPAQLPAPRTLLTKGTLEPEYFNSVCRLMKTIGPDMFLGTCRRCP

AEIVDTVSALVYDNKL
```

SEQ ID NO: 6 is the amino acid sequence of a SARS-CoV-2 Region 1 optimized polypeptide (Region 1 SARS-CoV2-EG-2.1):

```
NCSDDRCILHCSNFNVLFSTVFPLTSFGPLVRKMFVDGVPFVISTGYHF

RELGVLHNQDVNLHSSRLSFNELLVYAADPAMHTASGNLLLDKRTMCFS

VAALTNNVAFQTVRPGNFNKDFYDFVVSKGFFKEGSFVELKHFFFAQDG

NAVISDYDYYRYNLPTICDIRQLLFVVEVVDNYFDCYDGGCINASQVIV

NNLDKSAGFPFNKWGKARFYYDSMSYEDQDALFVYTKRNVIPTITQMNL

KYAISAKNRSRTVAGVSIFSTMTNRQFYQKLLKSIASTRGATVVIGISK

FYGGWHNMLKTIYSDVENPHFMGWDYPKCDRAMPNILRIMASLVFARKH

TTCCILSHRFYRLSNECAQVLSEIVMCGGSLYVKPGGTSSGEATTAYAN

SVFNICQSVTANVNALLSTDGNKIADKYIRNLQHRLYACLYRNRDVDID

FVNEFYAYLRKHFSIMILSAAAVVCVNSTYASQGLLASIKNFKSVLYYQ

NNIFMSEAKCWTEIDLTKGPHEFCSQHTMLVKHGDDYVYLSYPDPSRIL

GAGCFVDDILKTDGTLMIERFVSLAIDAYPLIKHPNQEYADVFRLYLQY

IRKLHYELTGHMLDIYSVMLINDNTLRYWEPEFYDAMYTPHTVLQAVGV

CVLCNSQTSLRCGVCIRRPFLCCECCYDHVISTLHKLVLSVNPYVCNAL

GCDVTDVTQLYLGGMNYYCKSHKPSISFPLCANGHVFGLYKNTCFGSDN

VTDFNAIATCDWINAGDYILANTCIERLKLFAAETLKAIEETFKLSYGI

AIVREVLSDRELYLSWEVGKPRPPFNRNYVFTGYRLTKNSKVQIGDYTF

EKGDYVDAVVYRGTTTYRLNVGDYFVLTSHTVIPLSAPTLVPQDHYVRI

TGLYPTLNISDDFSSNVANYQKVGIQKYSTLQGPPGTGKSYFAIGLALY
```

```
YLSARIVYTACSHAAVYTLCEKALKYFPIDKCSRIIPARARVDCFDKFK
VNLTLEQYVFCTVNALPDTTADIVVFDEISMTTNYDLSVVNARLCAKHY
VYIGDSAQLPAPRTLLIKGTLEPEYFNSVCRFMKTIGPDMFLGTCRRCP
SEIVDTVSALVYDNRL
```

SEQ ID NO: 7 is the amino acid sequence of an additional SARS-CoV-2 optimized Region 1 polypeptide (Region 1 SARS-CoV-2-EG-2.2):

```
NCLDDRCVLHCANFNVLFSTVFPPTSFGPLVRKICVDGVPFVVSTGHHF
RELGVVYNQDVNLHSFRLSFKELLLYAADPAMHVASGNLLLDRRTTCFS
VAALTNNFAFQTVKPGNFNKDFYDFALSKGFFKEGSPVELKHFFFVQDG
NAAISDYEYYRYNLPTMFDIRQLLFVFEVVDKYFDCYDGGCINANQVTV
NNLDKSAGFPFNKWGKARLYYESMSYEDQDVLFAYTKRNVTPTITQMNL
KYAISVKNRARTVAGVSICSTITNRQFHQKLLKSIAATGGATVVIGTSK
FYGGWHNILKTVYSDVENPYLMGWDYPKCDRAMPNMLRIVASLVLARKH
TMCCSLSHRFYRLTNECAQVLSEMVICGGSLYVKPGGTSSGDATTAYAN
SVFNIFQAVTANVNTLLSTDGNKIADNYVRNLQHRLYGCLYRNRDVYTD
FVNEFYTYLRKHFSMIILSAAAVVCFNSTYVSQGLVASIRNFKSVLYYQ
NNVFMSEVKCWTETDLIKGPHEFCSQHTILVKQGDDYVYFPYPDPSRIL
GAGCFVDDVVKTDGTLMVERFVSLAIDAYPFTKHPNQEYAYVFHLYLQY
IKKLHDELTGHILDMYSVMLINDNTSRYWESEFYEAMYTSHTVLQAVGS
CVLCNSQTLLRCGACIRKPFLCCKCCYDHIISTSHKLVFSVNPYVCNVP
GCDVTDVTQLCLGGMSYYCKPHKPPISFPLCVNGQVFGLYKNTCAGSDN
VTDFNAISTCDWTNAGDYILANACTERLKLFAAEMLKATEETFKLSYGV
ATVREVLSDKELHLSWEVGRPRPPLNRNYVFTGYHVTKNSKVQTGEYTF
EKGYYGDAVVYRGITTYKLNVGDYFLLTSHTVMPLSAPILVPQEHYVRI
IGLYPTLNISYEFSSNVANYQKVGMQRYSTLQGPPGTGKSHFAIGLSLY
YPSARIMYTACSHAAVDALCDKALKYLPIDKCSRIIPARALVECFDKFK
LNSTLEQYVFCTVNALPETTVDIVVFDEISMTTNYDLSVVNVRLRAKHY
VYVGDPAQLPAPRTLLTKGILEPEYFNSVCRLIKTIGPDMFLRTCRRCP
AEIVDTLSALVYDNKL
```

SEQ ID NO: 8 is the amino acid sequence of a sarbecovirus optimized region 1 polypeptide (Region 1 SARBECO-EG-2.1):

```
NCLDDRCILHCANFNVLFSTVFPLTSFGPLVRKIFVDGVPFVVSTGYHF
RELGVVHNQDVNIHSSRLSFKELLVYAADPAMHAASGNLLLDKRTTCFS
VAALTNNVSFQTVKPGNFNKDFYDFAVSKGFFKEGSSVELKHFFFAQDG
NAAISDYDYYRYNLPTMCDIRQLLFVVEVVDKYFDCYDGGCINANQVIV
NNLDKSAGFPFNKWGKARLYYDSMSYEDQDALFAYTKRNVLPTITQMNL
KYAISAKNRARTVAGVSICSTMTNRQFHQKLLKSIAATRGATVVIGTSK
FYGGWNNMLKTVYSDVETPHLMGWDYPKCDRAMPNMLRIMASLVLARKH
STCCNLSHRFYRLANECAQVLSEMVMCGGSLYVKPGGTSSGDATTAYAN
SVFNICQAVTANVNALLSTDGNKIGDKYIRNLQHRLYECLYRNRDVDHE
FVDEFYAYLRKHFSMMILSAAAVVCYNSNYAAQGLVASIKNFKAVLYYQ
NNVFMSEAKCWTETDLTRGPHEFCSQHTMLVKQGDDYVYLPYPDPSRIL
GAGCFVDDIVKTDGTLMIERFVSLAIDAYPLTKHPNQEYADVFHLYLQY
IRKLHDELTGHMLDMYSVMLTNDSTSRYWEPEFYEAMYTPHTILQAVGA
CVLCNSQTSLRCGACIRRPFLCCKCCYDHVISTSHKLVLSVNPYVCNAT
GCDVTDVTQLYLGGMSYYCKAHKPPISFPLCANGQVFGLYKNTCVGSDN
VTDFNAIATCDWTNAGDYILANTCTERLKLFAAETLKATEETFKLSYGI
ATVREVLSDRELYLSWEVGKPRPPLNRNYVFTGYRVTKNSKTQIGEYTF
EKGDYGDAVVYRGTTTYKLNVGDYFVLTSHTVMPLSAPTLVPQEHYVRI
TGLYPTLNISEEFSSNVANYQKIGMQKYSTLQGPPGTGKSHFAIGLALY
YPSARIVYTACSHAAVDALCEKALKYLPIDKCSRIIPARARVECFDKFK
VNSTLEQYVFCTVNALPETTADIVVFDEISMATNYDLSVVNARLRAKHY
VYIGDPAQLPAPRTLLTKGTLEPEYFNSVCRLMKTIGPDMFLGTCRRCP
AEIVDTVSALVYDNKL
```

SEQ ID NO: 9 is the amino acid sequence of an additional sarbecovirus optimized Region 1 polypeptide (Region 1 SARBECO-EG-2.2):

```
NCLDDRCILHCANFNVLFSTVFPPTSFGPLVRKIFVDGVPFVVSTGYHF
RELGVVHNQDVNIHSSRLSFKELLVYAADPAMHAASGNLLLDKRTTCFS
VAALTNSVAFQTVKPGNFNKDFYDFAVSKGFFKEGSSVELKHFFFAQDG
NAAISDYDYYRYNLPTMCDIRQLLFVVEVVDKYFDCYDGGCINANQVIV
NNLDKSAGFPFNKWGKARLYYDSMSYEDQDALFAYTKRNVLPTITQMNL
KYAISAKNRARTVAGVSICSTMTNRQFHQKLLKSIAATRGATVVIGTSK
FYGGWNNMLKTVYSDVESPHLMGWDYPKCDRAMPNMLRIMASLVLARKH
NTCCNLSHRFYRLANECAQVLSEMVMCGGSLYVKPGGTSSGDATTAYAN
SVFNICQAVTANVNALLSTDGNKIADKYVRNLQHRLYECLYRNRDVTDD
FVNEFYAYLRKHFSMMILSAAAVVCYNSNYAAQGLVASIKNFKSVLYYQ
NNVFMSEAKCWTETDLTRGPHEFCSQHTMLVKQGDDYVYLPYPDPSRIL
GAGCFVDDIVKTDGTLMIERFVSLAIDAYPLTKHPNQEYADVFHLYLQY
IRKLHDELTGHMLDMYSVMLTNDNTSRYWEPEFYEAMYTPHTVLQAVGA
CVLCNSQTSLRCGACIRRPFLCCKCCYDHVISTSHKLVLSVNPYVCNAP
GCDVTDVTQLYLGGMSYYCKLHKPPISFPLCANGQVFGLYKNTCVGSDN
VTDFNAIATCDWTNAGDYILANTCTERLKLFAAETLKATEETFKLSYGI
ATVREVLSDRELHLSWEVGKPRPPLNRNYVFTGYRVTKNSKVQIGEYTF
EKGDYGDAVVYRGTTTYKLNVGDYFVLTSHTVMPLSAPTLVPQEHYVRI
TGLYPTLNISDEFSSNVANYQKIGMQKYSTLQGPPGTGKSHFAIGLALY
```

```
YPSARIVYTACSHAAVDALCEKALKYLPIDKCSRIIPARARVECFDKFK

VNSTLEQYVFCTVNALPETTADIVVFDEISMATNYDLSVVNARLRAKHY

VYIGDPAQLPAPRTLLTKGTLEPEYFNSVCRLMKTIGPDMFLGTCRRCP

AEIVDTVSALVYDNKL
```

SEQ ID NO: 10 is the amino acid sequence of an alternative exemplary conserved region SARS-CoV-2 polypeptide spanning nsp6 through nsp10 proteins (Region 2)

```
GGKPCIKVATVQSKMSDVKCTSVVLLSVLQQLRVESSSKLWAQCVQLHN

DILLAKDTTEAFEKMVSLLSVLLSMQGAVDINKLCEEMLDNRATLQAIA

SEFSSLPSYAAFATAQEAYEQAVANGDSEVVLKKLKKSLNVAKSEFDRD

AAMQRKLEKMADQAMTQMYKQARSEDKRAKVTSAMQTMLFTMLRKLDND

ALNNIINNARDGCVPLNIIPLTTAAKLMVVIPDYNTYKNTCDGTTFTYA

SALWEIQQVVDADSKIVQLSEISMDNSPNLAWPLIVTALRANSAVKLQN

NELSPVALRQMSCAAGTTQTACTDDNALAYYNTTKGGRFVLALLSDLQD

LKWARFPKSDGTGTIYTELEPPCRFVTDTPKGPKVKYLYFIKGLNNLNR

GMVLGSLAATVRLQAGNATEVPANSTVLSFCAFAVDAAKAYKDYLASGG

QPITNCVKMLCTHTGTGQAITVTPEANMDQESFGGASCCLYCRCHIDHP

NPKGFCDLKGKYVQIPTTCANDPVGFTLKNTVCTVCGMWKGYGCSCDQL
```

SEQ ID NO: 11 is the amino acid sequence of a SARS-CoV-2 Region 2 optimized polypeptide (Region 2 SARS-CoV2-EG-2.1):

```
GGKPCVKVATVQSKISDVKCTSVVLLLVLQQLRVESLSKLWAQCVQLHN

DIILAKDTTEAFGKMVSLLSVLLSMQRAVDINKLCEEILDNRATLQSIA

SEFSSLSSYAAFATAQEAYERAVANGDSEVFLKKLKKSLNVAKSEFDCD

AAMQRKLENMADQAMTQMYKQVRSEDKRAKVTSAMQIMLFTMLRKFDND

ALNNIVNNARDGCVPLNIIPFTTAAKLMVVISDYNTYKNTCDGITFTYA

SALWEIQHVVDADSKIVQFSEISMDNSSNLAWPLIVIALRANSAVKLQN

NELSPVVLRQMSCAAGTTQTACIDDNALAYYNTIKGGRFVLALLSNLQD

LKWARFPKSDGTGTVYTELEPPCGFVTDTPKGLKVKYLYFIRGLNNLNR

GIVLGSLAATVRLQAGKATEVPANSIVLSFCAFAIDAAKAYKDYLVSGG

QPITNCVKMLCTHIGTGQAITVIPEANMDQESFGGASCCMYCRCHIDHP

DPKGFCDLKGKYVQIPTICANDPVGFILKNTVCTVCSMWKGYGCSCDQL

C
```

SEQ ID NO: 12 is the amino acid sequence of an additional SARS-CoV-2 optimized Region 2 polypeptide (Region 2 SARS-CoV2-EG-2.2):

```
GGKPCIKVATVQSKTSDVKCTSVVLLSVFQQLRVESSFKLWAQCVQLHN

DILLARDTTEAFEKMVSLLSVLFSMQGAVDINKFCEEMLDNRAILQAIA

SEFSSLPSYAALATAQEAYEQAVVNGDSEVVLKNLKKSLNVAKSEFDLD

AAMQRKLEKMSDQAMTQMYKQAKSEDKRAKVISAMQTMLFTMFRKLDND

ALNNIIDNARDGCVPLNIIPLITAAKLMVVTPDYNTYKNMCDGTTFIYA

SALWEIQQVVNADSKIVQLSEVSMDNSPNLAWPLVVTALRANSAIKLQN

NELSPIALRQMSCAAGTIQTACTDDNALVYYNTTKGGRFVFALLSDLQD

LKWARFSKSDGTGTIYIELEPPCRFVTDTLKGPKVKYLYFIKRLNNLNR

GMVLGSLAAIVRLQAGNAIEVPANSTVLFFCAFAVDASKAYKDYLASGG

QPIINCVKMLCTHTGIGQAITVTPEANMEQESFGGASCCLYCRCHIDHS

NPKGFCDLKGRYVQIPTTCVNDPVGFTLKNTVCTICGMWKGYGCGCDQL

R
```

SEQ ID NO: 13 is the amino acid sequence of a sarbecovirus Region 2 optimized polypeptide (Region 2 SARBECO-EG-2.1):

```
GGKPCIKVATVQSKMSDVKCTSVVLLSVLQQLRVESSSKLWAQCVQLHN

DILLAKDTTEAFEKMVSLLSVLLSMQGAVDINRLCEEMLDNRATLQAIA

SEFSSLPSYAAYATAQEAYEQAVSNGDSEVVLKKLKKSLNVAKSEFDHD

AAMQRKLEKMADQAMTQMYKQARSEDKRAKVTSAMQTMLFTMLRKLDND

ALNNIINNARDGCVPLNIIPLTTAAKLMVVVPDYGTYKNTCDGNTFTYA

SALWEIQQVVDADSKIVQLSEINMDNSPNLAWPLIVTALRANSAVKLQN

NELSPVALRQMSCAAGTTQTACNEDNALAYYNNSKGGRFVLALLSDHQD

LKWARFPKSDGTGTIYTELEPPCRFVTDTPKGPKVKYLYFIKGLNNLNR

GMVLGSLAATVRLQAGNATEVPANSTVLSFCAFAVDPAKAYKDYLSSGG

QPITNCVKMLCTHTGTGQAITVTPEANMDQESFGGASCCLYCRCHIDHP

NPKGYCELKGKYVQIPTTCANDPVGFTLRNTVCTVCGMWKGYGCSCDQL

R
```

SEQ ID NO: 14 is the amino acid sequence of an additional sarbecovirus region 2 optimized polypeptide (Region 2 SARBECO-EG-2.2):

```
GGKPCIKVATVQSKMSDVKCTSVVLLSVLQQLRVESSSKLWAQCVQLHN

DILLAKDTTEAFEKMVSLLSVLLSMQGAVDINRLCEEMLDNRATLQAIA

SEFSSLPSYAAFATAQEAYEQAVANGDSEVVLKKLKKSLNVAKSEFDRD

AAMQRKLEKMADQAMTQMYKQARSEDKRAKVTSAMQTMLFTMLRKLDND

ALNNIINNARDGCVPLNIIPLTTAAKLMVVVPDYNTYKNTCEGSTFTYA

SALWEIQQVVDADSKIVPLSEINMDNSQNLAWPLIVTALRANSAVKLQN

NELSPVALRQMSCAAGTTQTACTDDNALAYYNTSKGGRFVLALLSDLQD

LKWARFPKSDGTGTIYTELEPPCRFVTDTPKGPKVKYLYFIKGLNNLNR

GMVLGSLAATVRLQAGNATEVPANSTVLSFCAFAVDASKAYRDYLASGG

QPITNCVKMLCTHTGTGQAITVTPEANMDQESFGGASCCLYCRCHIDHP

NPKGFCDLKGKYVQIPTTCANDPVGFTLRNTVCTVCGMWKGYGCSCDQL

R
```

SEQ ID NO: 15 is an exemplary nucleic acid sequence encoding the protein of SEQ ID NO: 5.

SEQ ID NO: 16 is an exemplary nucleic acid sequence encoding the protein of SEQ ID NO: 3.

SEQ ID NO: 17 is an exemplary nucleic acid sequence encoding the protein of SEQ ID NO: 2.

SEQ ID NO: 18 is the amino acid sequence of COVconsv.

DETAILED DESCRIPTION

T-cell responses play an important part in viral clearance of influenza during infection, and are critical for mediating clearance of coronavirus and other acute viral infections of the lung. Furthermore, vaccine elicited cytotoxic T lymphocyte (CTL) responses can protect mice from lethal challenges with SARS coronavirus (CoV). Disclosed here are immunogenic polypeptides and nucleic acids encoding such polypeptides, designed using regions of the virus that are very highly or even totally conserved in the current outbreak, but are also highly conserved among other CoVs, thus identifying regions of the virus that are potentially vulnerable to immune attack. Provided are compositions and methods for eliciting T-cell responses to a spectrum of diverse viruses in a subject, with the targeted diversity coverage selected to include Sarbecoviruses in bats, pangolins, and humans, or alternatively the viral diversity that has evolved within the SARS-CoV-2 global pandemic. The methods include administering to the subject a composition comprising one or more of the disclosed polypeptides or one or more nucleic acids encoding the disclosed polypeptides. The specific regions of the coronavirus proteome targeted include the most conserved regions in the viral proteome across a diverse sampling of Sarbecoviruses.

Sarbecoviruses are a highly diverse subgenus of the family Coronaviridae. Sarbecoviruses are common in bats and also found in pangolins and other mammals, and members of this subgenus have twice entered the human population, the SARS CoV-1 epidemic nearly two decades ago, and the current SARS CoV-2 epidemic. The intent of defining highly conserved regions was two-fold. First, if these regions were immunogenic when delivered in a vaccine, and could elicit effective T cell responses that could prevent disease, the responses would be highly likely to be cross-reactive and potentially able to protect vaccinated individuals and allow a rapid response should another Sarbecovirus undergo zoonosis in the future. Second, it is believed that protein regions that are highly conserved among diverse population are under fitness constraints and would not be able to readily escape immune responses. Furthermore, T cell responses may be a factor in the disease severity outcome for people infected with SARS-CoV-2, and vaccine-elicited responses T cell responses to epitopes in highly conserved regions of the virus across Sarbecoviruses would not readily be able to evade the response through viral escape. Thus vaccine-elicited responses to conserved regions may be beneficial in terms of disease outcomes in the more limited diversity setting of SARS-CoV-2.

This conserved region approach, where a long stretch of contiguous amino acids are used, is believed to likely be optimal for a T-cell vaccine strategy, because it maximizes the number of potential epitopes that can be targeted, and if T cell responses are elicited, because they are by definition from conserved regions, such T cell responses are highly likely to be cross-reactive with variants, and also to be difficult to escape without a fitness cost. The cross-reactive potential confers value at the population level. The fitness cost of escape may help contain the virus in vivo. CTL responses in natural COVID-19 infection may help with improving disease outcomes, and CTL escape variants that arise in vivo may be associated with more serious outcomes, but would seldom be transmitted as they would arise after the period of high transmissibility early in infection. Thus even if escape mutations in CTL epitopes are rarely observed at the population level, they may still be relevant to disease outcome. Therefore, a vaccine that re-directed the response to conserved epitope(s) with a high mutation cost for escape could be valuable. Larger regions are utilized rather than alternative strategies that target a series of known epitopes, very short extremely conserved regions, or topologically constrained epitopes within short fragments, because longer conserved stretches will contain many more overlapping potential epitopes, and they are more likely to be targeted multiple times by most people.

The specific components in some embodiments include artificial sequences derived using the Epigraph algorithm (designated herein as sequences named "EG"), and these are designed to be complementary to, and in some instances used in combination with, the natural ancestral sequence of the COVID-19 pandemic that was first identified in Wuhan, China.

I. Terms

Unless otherwise noted, technical terms are used according to conventional usage. Definitions of common terms in molecular biology may be found in *Lewin's Genes X*, ed. Krebs et al., Jones and Bartlett Publishers, 2009 (ISBN 0763766321); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, Proteomics and Informatics*, $3^{rd}$ Edition, Springer, 2008 (ISBN: 1402067534), and other similar references, Unless otherwise explained, all technical and scientific terms used herein have the same meaning as commonly understood by one of ordinary skill in the art to which this disclosure belongs. The singular terms "a," "an," and "the" include plural referents unless the context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description.

Although methods and materials similar or equivalent to those described herein can be used in the practice or testing of the present disclosure, suitable methods and materials are described below. All publications, patent applications, patents, and other references mentioned herein are incorporated by reference in their entirety, as are the GenBank® Accession numbers. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Adjuvant: A vehicle or composition used to enhance antigenicity. Adjuvants include a suspension of minerals (alum, aluminum hydroxide, or phosphate) on which antigen is adsorbed; or water-in-oil emulsion in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). Immunostimulatory oligonucleotides (such as those including a CpG motif) can also be used as adjuvants. Adjuvants include biological molecules (a "biological adjuvant"), such as costimulatory molecules. Exemplary adjuvants include IL-2, RANTES, GM-CSF, TNF-α, IFN-γ, G-CSF, LFA-3, CD72, B7-1, B7-2, OX-40L and 41 BBL. Adjuvants can be used in combination with the disclosed conserved region polypeptides and nucleic acids.

Administration: The introduction of a composition into a subject by a chosen route. For example, if the chosen route is intramuscular, the composition (such as a disclosed antigen) is administered by introducing the composition intramuscularly into a subject.

Coronavirus: A family of positive-sense, single-stranded RNA viruses that can infect humans and non-human animals. The viral envelope is comprised of a lipid bilayer containing the viral membrane (M), envelope (E) and spike (S) proteins. Most coronaviruses cause mild to moderate upper respiratory tract illness, such as the common cold. However, three coronaviruses have emerged that can cause more serious illness and death in humans: severe acute respiratory syndrome coronavirus (SARS-CoV), SARS-CoV-2, and Middle East respiratory syndrome coronavirus (MERS-CoV). Other coronaviruses that infect humans include human coronavirus HKU1 (HKU1-CoV), human coronavirus OC43 (OC43-CoV), human coronavirus 229E (229E-CoV), human coronavirus NL63 (NL63-CoV). SARS-CoV-1, SARS-CoV-2, and related bat and pangolin viruses are members of the subgenus Sarbecovirus (group 2b).

Immunogen: A compound, composition, or substance that can stimulate the production of antibodies or a T cell response in a subject, including compositions that are injected or absorbed into a subject. An immunogen reacts with the products of specific humoral or cellular immunity, including those induced by heterologous antigens, such as the disclosed antigens. "Epitope" or "immunogenic determinant" refers to the region of an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and nuclear magnetic resonance.

Examples of immunogens include, but are not limited to, peptides, lipids, polysaccharides, and nucleic acids containing antigenic determinants, such as those recognized by an immune cell. In some examples, immunogens include peptides derived from a pathogen of interest. In specific examples, an immunogen is derived from a coronavirus, for example, one or more coronavirus polypeptides or a fragment thereof, such as at least a portion of one or more of RNA-dependent RNA polymerase, helicase, and nsp6-10 proteins or variants thereof.

Immunogenic polypeptide: A protein or a portion thereof that is capable of inducing an immune response in a subject, such as a subject infected or at risk of infection with a pathogen. Administration of an immunogenic polypeptide or its coding sequence derived from a pathogen of interest can induce an immune response. Administration of an immunogenic polypeptide or its coding sequence can in some examples lead to protective immunity against a pathogen of interest. In some examples, an immunogenic polypeptide is a polypeptide including one or more conserved regions from a coronavirus proteome, for example, a polypeptide including one or more conserved regions.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a $CD4^+$ T cell response or a $CD8^+$ T cell response.

Immunogenic composition: A composition comprising an immunogenic polypeptide or a nucleic acid encoding an immunogenic polypeptide that induces a measurable immune response, for example, a measurable CTL response against virus expressing the immunogenic polypeptide or a portion thereof, a measurable helper T cell response, or a measurable B cell response (such as production of antibodies) against the immunogenic polypeptide or a portion thereof. In one example, an "immunogenic composition" is composition including one or more conserved region polypeptides from a coronavirus, such as the conserved regions disclosed herein. It further refers to isolated nucleic acids encoding an immunogenic polypeptide, such as a nucleic acid (for example, a vector or an mRNA) that can be used to express the immunogenic polypeptide (and thus be used to elicit an immune response against the polypeptide or a portion thereof).

For in vitro use, an immunogenic composition may consist of at least one (such as two or more) isolated polypeptide, peptide epitope, or nucleic acids encoding the polypeptide or peptide epitope. For in vivo use, the immunogenic composition will typically include at least one (such as one, two, three, four, five, or more) polypeptide, peptide, or nucleic acid in a pharmaceutically acceptable carrier, and may also include other agents (such as adjuvant(s)). Any particular peptide, such as a disclosed conserved region polypeptide or a nucleic acid encoding the polypeptide, can be readily tested for its ability to induce an immune response by art-recognized assays. Immunogenic compositions can include adjuvants, which are well known to one of skill in the art.

Isolated: An "isolated" biological component (such as a protein, for example a disclosed polypeptide or nucleic acid encoding such a polypeptide) has been substantially separated or purified away from other biological components, such as other chromosomal and extrachromosomal DNA, RNA, and proteins. Proteins, peptides, and nucleic acids that have been "isolated" include proteins purified by standard purification methods. The term also embraces proteins or peptides prepared by recombinant expression in a host cell as well as chemically synthesized proteins, peptides, and nucleic acid molecules. Isolated does not require absolute purity, and can include protein, peptide, or nucleic acid molecules that are at least 50% isolated, such as at least 75%, 80%, 90%, 95%, 98%, 99%, or even 99.9% isolated.

Operably linked: A first nucleic acid is operably linked with a second nucleic acid when the first nucleic acid is placed in a functional relationship with the second nucleic acid. For instance, a promoter is operably linked to a coding sequence if the promoter affects the transcription or expression of the coding sequence. Generally, operably linked nucleic acids are contiguous and, where necessary to join two protein-coding regions, in the same reading frame. In some examples, the operably linked nucleic acids are heterologous, for example, the first and second nucleic acids are from different organisms, different genes, or different polypeptides and the resulting nucleic acid is not naturally occurring.

Pharmaceutically acceptable carriers: The pharmaceutically acceptable carriers useful in this disclosure are known to one of ordinary skill in the art. *Remington: The Science and Practice of Pharmacy*, The University of the Sciences in Philadelphia, Editor, Lippincott, Williams, & Wilkins, Philadelphia, PA, 21$^{st}$ Edition (2005), describes compositions and formulations suitable for pharmaceutical delivery of the proteins, nucleic acids, and other compositions herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions, powder, pill, tablet, or capsule forms, conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: Any compound composed of amino acids, amino acid analogs, chemically bound together. The term polypeptide as used herein includes oligomers of amino acids, amino acid analogs, or small and large peptides, including proteins. Any chain of amino acids, regardless of length or post-translational modification (such as glycosylation or phosphorylation) is referred to as a polypeptide. The term polypeptide applies to amino acid polymers including naturally occurring amino acid polymers and non-naturally occurring amino acid polymers as well as polymers in which one or more amino acid residue is a non-natural amino acid, for example an artificial chemical mimetic of a corresponding naturally occurring amino acid. As used herein, polypeptide also refers to recombinant amino acid polymers, such as polymers including portions that are obtained from different (typically non-contiguous) portions of a genome (such as a coronavirus genome) and/or are obtained from different genomes (such as two or more distinct coronaviruses). A "residue" refers to an amino acid or amino acid mimetic incorporated in a polypeptide by an amide bond or amide bond mimetic.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease. A "prophylactic" treatment is a treatment administered to a subject who does not exhibit signs of a disease or exhibits only early signs for the purpose of decreasing the risk of developing pathology. The prophylactic treatment can be pre-exposure or post-exposure.

Purified: The term purified does not require absolute purity; rather, it is intended as a relative term. Thus, for example, a purified protein is one in which the protein is more enriched than the protein is in its natural environment within a cell. Preferably, a preparation is purified such that the protein represents at least 50% of the protein content of the preparation.

Recombinant nucleic acid or polypeptide: A nucleic acid molecule or polypeptide that is not naturally occurring or has a sequence that is made by an artificial combination of two otherwise separated segments of nucleotide or amino acid sequence. This artificial combination is accomplished by chemical synthesis or, more commonly, by the artificial manipulation of isolated segments of nucleic acids, e.g., by genetic engineering techniques such as those described in Sambrook et al. (ed.), *Molecular Cloning: A Laboratory Manual*, 2$^{nd}$ ed., vol. 1-3, Cold Spring Harbor Laboratory Press, Cold Spring Harbor, NY, 1989. The term "recombinant" includes nucleic acids or polypeptides that have been altered solely by addition, substitution, or deletion of a portion of a natural nucleic acid molecule or peptide.

Sequence identity/similarity: Sequence identity between two or more nucleic acid sequences or between two or more amino acid sequences can be measured in terms of percentage identity; the higher the percentage, the more identical the sequences are. Homologs or orthologs of nucleic acid or amino acid sequences possess a relatively high degree of sequence identity/similarity when aligned using standard methods.

Methods of alignment of sequences for comparison are well known in the art. The NCBI Basic Local Alignment Search Tool (BLAST) is available from several sources, including the National Center for Biological Information (NCBI, National Library of Medicine, Building 38A, Room 8N805, Bethesda, MD 20894) and on the Internet, for use in connection with the sequence analysis programs blastp, blastn, blastx, tblastn, and tblastx. Blastn is used to compare nucleic acid sequences, while blastp is used to compare amino acid sequences. Additional information can be found at the NCBI web site.

In some examples, sequence similarity is assessed by the conservation of epitope-length fragments. The use of this measure of similarity was developed at Los Alamos National Laboratory, and tools are available on the World Wide Web at hiv.lanl.gov.

Subject: Living multi-cellular vertebrate organisms, a category that includes both human and non-human mammals (including non-human primates).

Therapeutically effective amount or Effective amount: The amount of agent, such as nucleic acid, polypeptide, or other therapeutic agent, that is sufficient to prevent, treat (including prophylaxis), reduce, and/or ameliorate the symptoms and/or underlying causes of any of a disorder or disease. In some embodiments, an "effective amount" is sufficient to reduce or eliminate a symptom of a disease, such as coronavirus infection, for example, COVID19. For instance, this can be the amount necessary to inhibit viral replication or to measurably alter outward symptoms of the viral infection. In general, this amount will be sufficient to measurably inhibit virus replication or infectivity.

T Cell: A white blood cell critical to the immune response. T cells include, but are not limited to, CD4$^+$ T cells and CD8$^+$ T cells. A CD4$^+$ T lymphocyte is an immune cell that carries a marker on its surface known as "cluster of differentiation 4" (CD4). These cells, also known as helper T cells, help orchestrate the immune response, including antibody responses as well as killer T cell responses. CD8$^+$ T cells carry the "cluster of differentiation 8" (CD8) marker. In one embodiment, a CD8$^+$ T cell is a cytotoxic T lymphocyte (CTL). In another embodiment, a CD8$^+$ cell is a suppressor T cell.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of DNA by electroporation, lipofection, and particle gun acceleration.

Vaccine: A pharmaceutical composition that elicits a prophylactic or therapeutic immune response in a subject. In some cases, the immune response is a protective immune response and can block subsequent infection, in other cases it can limit the pathological impact of an infection by containing the infection. Typically, a vaccine elicits an antigen-specific immune response to an antigen of a pathogen, for example a viral pathogen, or to a cellular constituent correlated with a pathological condition. A vaccine may include a polynucleotide (such as a nucleic acid encoding a disclosed polypeptide), a peptide or polypeptide, a virus, a cell, or one or more cellular constituents.

Vector: A nucleic acid molecule that can be introduced into a host cell, thereby producing a transformed host cell.

Exemplary amino acid sequences of coronavirus polypeptides included in the compositions and methods provided herein or encoded by the nucleic acids included in the compositions and methods provided herein include SEQ ID NOs: 1-14 and 18. In some examples, the disclosed polypeptides include, consist essentially of, or consist of an amino acid sequence at least 95% identical to the amino acid sequence of any one of SEQ ID NOs: 1-14 and 18, such as at least 95% identical, at least 96% identical, at least 97% identical, at least 98% identical, at least 99% identical, or even 100% identical to the amino acid sequence of any one of SEQ ID NOs: 1-14 and 18. In some non-limiting embodiments, the components have at least the percent identity shown in Table 1, compared to a naturally occurring (e.g., Wuhan reference strain, GenBank® Accession No. NC_045512) coronavirus, such as the indicated sequences provided herein.

TABLE 1

Exemplary sequence identity of disclosed vaccine polypeptides

| | Region 1 | | Region 2 | |
| --- | --- | --- | --- | --- |
| | SARS-CoV-2 | Sarbeco | SARS-CoV-2 | Sarbeco |
| Reference | SEQ ID NO: 1 | SEQ ID NO: 1 | SEQ ID NO: 10 | SEQ ID NO: 10 |
| Epigraph 1 | 96% | 98% | 95% | 97% |
| | (SEQ ID NO: 6) | (SEQ ID NO: 8) | (SEQ ID NO: 11) | (SEQ ID NO: 13) |
| Epigraph 2 | 96% | 99% | 95% | 98% |
| | (SEQ ID NO: 7) | (SEQ ID NO: 9) | (SEQ ID NO: 12) | (SEQ ID NO: 14) |

Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant DNA vectors having at least some nucleic acid sequences derived from one or more viruses.

II. Immunogenic Compositions

Provided herein are immunogenic compositions and methods of use for eliciting an immune response to a coronavirus (such as SARS-CoV-2) in a subject. In some embodiments, the compositions include optimized viral polypeptides that are computationally derived from naturally-occurring coronavirus proteomes. The optimized viral polypeptides allow for improved virus-specific immunity (e.g., T cell-based immune responses) following administration to a subject. In some embodiments, the composition includes at least two different optimized viral polypeptides for each represented viral polypeptide. Including at least two different optimized viral polypeptides allows for increased coverage and representation of immunogenic epitopes in the composition.

In some embodiments, the immunogenic composition includes one or more (such as 1, 2, 3, or more) polypeptides that are optimized to cover 9-mer diversity in a conserved region of SARS-CoV-2 proteomes. In other embodiments, the immunogenic composition includes one or more (such as 1, 2, 3, or more) polypeptides that are optimized to cover 9-mer diversity in a conserved region of Sarbecovirus proteomes (e.g., "pan-Sarbecovirus"). In other embodiments, the immunogenic composition includes one or more (such as 1, 2, 3, or more) nucleic acids encoding one or more of the disclosed polypeptides.

In particular embodiments, the disclosed compositions include one or more (such as 1, 2, 3, or more) polypeptides or one or more nucleic acids (such as 1, 2, 3, or more) encoding the polypeptides. In some embodiments, the compositions include one or more polypeptides or nucleic acids encoding polypeptides eliciting T-cell responses to a spectrum of diverse viruses in a subject, with the targeted diversity coverage selected to include the viral diversity that has evolved within the SARS-CoV-2 global pandemic. Thus, in some examples, the compositions include one or more "SARS-CoV-2 Region 1" polypeptides or nucleic acids encoding polypeptides selected from sequences with at least 95% sequence identity (such as at least 95%, at least 96%, at least 97%, at least 98%, at least 99%, or even 100% sequence identity) to SEQ ID NOs: 5-7. In particular examples, the compositions include polypeptides or nucleic acids encoding polypeptides as follows: SEQ ID NO: 5 and SEQ ID NO: 6; or SEQ ID NO: 5, SEQ ID NO: 6, and SEQ ID NO: 7; or SEQ ID NO: 5 and SEQ ID NO: 7. In other examples, the compositions include one or more "SARS-CoV-2 Region 2" polypeptides or nucleic acids encoding polypeptides selected from sequences with at least 95% sequence identity (such as at least 95%, at least 96%, at least 97%, at least 98%, at least 99%, or even 100% sequence identity) to SEQ ID NOs: 10-12. In particular examples, the compositions include polypeptides or nucleic acids encoding polypeptides as follows: SEQ ID NO: 10; or SEQ ID NO: 10 and SEQ ID NO: 11; or SEQ ID NO: 10, SEQ ID NO: 11, and SEQ ID NO: 12; or SEQ ID NO: 10 and SEQ ID NO: 12.

In other embodiments, the compositions include one or more polypeptides or nucleic acids encoding polypeptides eliciting T-cell responses to a spectrum of diverse viruses in a subject, with the targeted diversity coverage selected to include Sarbecoviruses in bats, pangolins, and humans. Thus, in some examples, the compositions include one or more "Sarbecovirus Region 1" polypeptides or nucleic acids encoding polypeptides selected from sequences with at least 95% sequence identity (such as at least 95%, at least 96%, at least 97%, at least 98%, at least 99%, or even 100% sequence identity) to SEQ ID NOs: 5, 8, and 9. In particular examples, the compositions include polypeptides or nucleic acids encoding polypeptides as follows: SEQ ID NO: 5 and SEQ ID NO: 8; or SEQ ID NO: 5, SEQ ID NO: 8, and SEQ ID NO: 9; or SEQ ID NO: 5 and SEQ ID NO: 9. In other examples, the compositions include one or more "Sarbecovirus Region 2" polypeptides or nucleic acids encoding polypeptides selected from sequences with at least 95% sequence identity (such as at least 95%, at least 96%, at least 97%, at least 98%, at least 99%, or even 100% sequence identity) to SEQ ID NOs: 10, 13, and 14. In particular examples, the compositions include polypeptides or nucleic acids encoding polypeptides as follows: SEQ ID NO: 10; or SEQ ID NO: 10 and SEQ ID NO: 13; or SEQ ID NO: 10, SEQ ID NO: 13, and SEQ ID NO: 14; or SEQ ID NO: 10 and SEQ ID NO: 14.

Nucleic acids encoding the disclosed polypeptides (e.g., SEQ ID NOs: 1-14 and 18) are also disclosed herein. Unless otherwise specified, a "nucleic acid encoding a polypeptide" includes all nucleotide sequences that are degenerate versions of each other and encode the same amino acid sequence. For example, a polynucleotide encoding a disclosed immunogenic polypeptide includes a nucleic acid sequence that is degenerate as a result of the genetic code. There are 20 natural amino acids, most of which are specified by more than one codon. Therefore, all degenerate nucleotide sequences are included as long as the amino acid sequence of the polypeptide encoded by the nucleotide sequence is unchanged. In some embodiments, the disclosed polypeptide sequences are back-translated to codon optimized DNA. In particular non-limiting examples, the nucleic acids include the sequences set forth as SEQ ID NOs: 15-17.

In some embodiments, the nucleic acid encoding a disclosed polypeptide is DNA, RNA, or mRNA. In some embodiments, the nucleic acid may include one or more modified, alternative, or synthetic nucleotides or nucleosides. Modified, alternative, or synthetic nucleotides or nucleosides may be included for reasons including but not limited to improving stability of the nucleic acid in which they are incorporated, decreasing potential immunogenicity of, or immune response to, the nucleic acid, or other advantageous properties. In some examples, the nucleic acid includes one or more chemical modifications to the sugar, base, and/or internucleoside linkages. Exemplary modifications to the sugar include, but are not limited to, bridged nucleic acids (such as locked nucleic acid (LNA) and 2',4'-constrained ethyl nucleic acid ((S)-cET)), 2'-O-methyl (OMe), 2'-O-methoxy-ethyl (MOE), 2'-fluoro, cEt and tricyclo (tc)-DNA. Modifications to the internucleoside linkages include, for example, phosphorothioate and phosphoramidate, or peptide nucleic acid. In other examples, the nucleic acid is RNA and may include one or more modified nucleosides, such as $m^5C$ (5-methylcytidine); $m^5U$ (5-methyluridine); $m^6A$ ($N^6$-methyladenosine); $s^2U$ (2-thiouridine); pseudouridine; Um (2'-O-methyluridine); $m^1A$ (1-methyladenosine); $m^2A$ (2-methyladenosine); Am (2'-O-methyladenosine); $ms^2$ $m^6A$ (2-methylthio-$N^6$-methyladenosine); $i^6A$ ($N^6$-isopentenyladenosine); $ms^2i6A$ (2-methylthio-$N^6$ isopentenyladenosine); $io^6A$ ($N^6$-(cis-hydroxyisopentenyl)adenosine); $ms^2i^6A$ (2-methylthio-$N^6$-(cis-hydroxyisopentenyl)adenosine); $g^6A$ ($N^6$-glycinylcarbamoyladenosine); $t^6A$ ($N^6$-threonylcarbamoyladenosine); $ms^2t^6A$ (2-methylthio-$N^6$-threonyl carbamoyladenosine); $m^6t^6A$ ($N^6$-methyl-$N^6$-threonylcarbamoyladenosine); $hn^6A$ ($N^6$-hydroxynorvalylcarbamoyladenosine); $ms^2hn^6A$ (2-methylthio-$N^6$-hydroxynorvalyl carbamoyladenosine); Ar(p) (2'-O-ribosyladenosine (phosphate)); I (inosine); $m^1I$ (1-methylinosine); $m^1Im$ (1,2'-O-dimethylinosine); $m^3C$ (3-methylcytidine); Cm (2'-O-methylcytidine); $s^2C$ (2-thiocytidine); $ac^4C$($N^4$-acetylcytidine); fC (5-formylcytidine); $m^5$ Cm (5,2'-O-dimethylcytidine); $ac^4Cm$ ($N^4$-acetyl-2'-O-methylcytidine); $k^2C$ (lysidine); $m^1G$ (1-methylguanosine); $m^2G$ ($N^2$-methylguanosine); $m^7G$ (7-methylguanosine); Gm (2'-O-methylguanosine); $m^{22}G$ ($N^2$,$N^2$-dimethylguanosine); $m^2Gm$ ($N^2$,2'-O-dimethylguanosine); $m^{22}Gm$ ($N^2$,$N^2$,2'-O-trimethylguanosine); Gr(p) (2'-O-ribosylguanosine (phosphate)); yW (wybutosine); $o_{2y}W$ (peroxywybutosine); OHyW (hydroxywybutosine); OHyW* (undermodified hydroxywybutosine); imG (wyosine); mimG (methylwyosine); Q (queuosine); oQ (epoxyqueuosine); galQ (galactosyl-queuosine); manQ (mannosyl-queuosine); $preQ_0$ (7-cyano-7-deazaguanosine); $preQ_1$ (7-aminomethyl-7-deazaguanosine); $G^+$ (archaeosine); D (dihydrouridine); $m^5Um$ (5,2'-O-dimethyluridine); $s^4U$ (4-thiouridine); $m^5s^2U$ (5-methyl-2-thiouridine); $s^2Um$ (2-thio-2'-O-methyluridine); $acp^3U$ (3-(3-amino-3-carboxypropyl)uridine); $ho^5U$ (5-hydroxyuridine); $mo^5U$ (5-methoxyuridine); $cmo^5U$ (uridine 5-oxyacetic acid); $mcmo^5U$ (uridine 5-oxyacetic acid methyl ester); $chm^5U$ (5-(carboxyhydroxymethyl)uridine)); $mchm^5U$ (5-(carboxyhydroxymethyl)uridine methyl ester); $mcm^5U$ (5-methoxycarbonylmethyluridine); $mcm^5Um$ (5-methoxycarbonylmethyl-2'-O-methyluridine); $mcm^5s^2U$ (5-methoxycarbonylmethyl-2-thiouridine); $nm^5s^2U$ (5-aminomethyl-2-thiouridine); $mnm^5U$ (5-methylaminomethyluridine); $mnm^5s^2U$ (5-methylaminomethyl-2-thiouridine); $mnm^5se^2U$ (5-methylaminomethyl-2-selenouridine); $ncm^5U$ (5-carbamoylmethyluridine); $ncm^5Um$ (5-carbamoylmethyl-2'-O-methyluridine); $cmnm^5U$ (5-carboxymethylaminomethyluridine); $cmnm^5Um$ (5-carboxymethylaminomethyl-2'-O-methyluridine); $cmnm^5s^2U$ (5-carboxymethylaminomethyl-2-thiouridine); $m^6{}_2A$ ($N^6$, $N^6$-dimethyladenosine); Im (2'-O-methylinosine); $m^4C$($N^4$-methylcytidine); $m^4$ Cm ($N^4$,2'-O-dimethylcytidine); $hm^5C$ (5-hydroxymethylcytidine); $m^3U$ (3-methyluridine); $cm^5U$ (5-carboxymethyluridine); $m^6Am$ ($N^6$,2'-O-dimethyladenosine); $m^6{}_2Am$ ($N^6$,$N^6$,O-2'-trimethyladenosine); $m^{2,7}G$ ($N^2$,7-dimethylguanosine); $m^{2,2,7}G$ ($N^2$,$N^2$,7-trimethylguanosine); $m^3Um$ (3,2'-O-dimethyluridine); $m^5D$ (5-methyldihydrouridine); $f^5Cm$ (5-formyl-2'-O-methylcytidine); $m^1Gm$ (1,2'-O-dimethylguanosine); $m^1Am$ (1,2'-O-dimethyladenosine); $\tau m^5U$ (5-taurinomethyluridine); $\tau m^5s^2U$ (5-taurinomethyl-2-thiouridine)); imG-14 (4-demethylwyosine); imG2 (isowyosine); $ac^6A$ ($N^6$-acetyladenosine); 1-methylpseudouridine; 5-methoxyuridine; or 5-methylcytidine.

In particular examples, the nucleic acid is mRNA. In some examples, the nucleic acid (such as an mRNA) is formulated with a lipid nanoparticle (LNP). See, e.g., Pardi et al., *Nat. Commun.* 9:3361, 2018; Pardi et al., *Mol. Ther. Nucleic Acids* 15:36-47, 2019; both of which are incorporated herein by reference in their entirety. The mRNA may include one or more modified nucleosides, which in non-limiting examples may be 1-methylpseudouridine, 5-methylcytidine, or both. Additional modified nucleosides that may be used are set out above. Such modifications may reduce innate immune responses that can inhibit synthesis of the encoded immunogen. The mRNA is incorporated in a lipid nanoparticle, which may decrease degradation of the mRNA and/or facilitate cellular uptake, for example, compared to naked mRNA. Exemplary lipid nanoparticles that can be used include, but are not limited to, Lipid H (see, e.g., Hassett et al., *Mol. Ther. Nucleic Acids* 15:1-11, 2019), Acuitas ALC-0315 (see, e.g., International Pat. Publ. WO 2017/075531), imidazole cholesterol ester (ICE) based lipids (see e.g., U.S. Pat. Publ. 2020/0155691), cystine cationic lipids (e.g., International Pat. Publ. No. WO 2020/214946), Lipid 2,2 (8,8)4C CH3 (see, e.g., U.S. Pat. No. 9,670,152), Acuitas A9 (see, e.g., U.S. Pat. No. 10,221,127), and Genevant CL1 (see, e.g., International Pat. Publ. WO 2020/219941).

In other embodiments, a nucleic acid encoding a disclosed polypeptide is incorporated into a vector. In some embodiments, the vector is a viral vector. Viral vectors that can be used to express the disclosed polypeptides include polyoma, e.g., SV40; adenovirus; non-replicating adenoviruses of chimpanzee origin (ChAdV); vaccinia virus; modified vaccinia Ankara (MVA) virus; adeno-associated virus; herpes viruses, including HSV and EBV; Sindbis viruses; alphaviruses; and retroviruses of avian, murine, and human origin. Baculovirus (*Autographa californica* multinuclear polyhedrosis virus; AcMNPV) vectors are also known in the art, and may be obtained from commercial sources (such as PharMingen®, San Diego, Calif.; Protein Sciences Corp., Meriden, Conn.; Stratagene®, La Jolla, Calif.).

In some examples, vector includes a nucleic acid encoding a disclosed protein operably linked to a promoter. In non-limiting examples, the promoter is a cytomegalovirus (CMV) promoter (such as a CMV immediate early promoter), an SV40 promoter, an elongation factor 1α (EF1α) promoter, a phosphoglycerate kinase (PGK) promoter, or a β-actin promoter, such as a chicken β-actin promoter. One of skill in the art can select additional promoters that can be used in the disclosed vectors. In additional examples, the nucleic acid is also operably linked to an enhancer element (such as a CMV enhancer) and/or a polyadenylation signal (such as a β-globin polyadenylation signal or an SV40 polyadenylation signal). Other elements that optionally can be included in the vector include tags (such as 6xHis, HA, or other tags for protein detection).

In some embodiments, the vector is an adenovirus vector. In some examples, the adenovirus vector is a recombinant adenovirus vector. In other examples, the adenovirus vector is a replication-competent adenovirus vector. In further examples, the adenovirus vector is a replication-deficient adenovirus vector. In some non-limiting examples, the adenovirus vector is derived from human adenovirus, such as an adenovirus serotype 5 (Ad5), adenovirus serotype 26 (Ad26), adenovirus serotype 35 (Ad35), or adenovirus serotype 52 (Ad52) vector. In other non-limiting examples, the adenovirus is a simian adenovirus (SAdV), such as of chimpanzee origin (ChAdV) or derived from a ChAdV. One potential advantage to using a ChAdV is that there may be lower prevalence of pre-existing antibodies against the vector in the human population. In some examples, the vector is ChAdOx1, which is derived from SAdV isolate Y25 of group E adenoviruses, modified by HAdV-5 E4 Orf4 and Orf6/7 (Ondondo et al., *Mol. Ther.* 24:832-842, 2016). In further examples, the vector is ChAdOx2, which is a C68 genome modified by removal of the E1 and E3 regions, and substitution of the E4 region with E4Orf4, Orf6, and Orf6/7 from HAdV-5 and E4Orf1, Orf2, and Orf3 from SAdV Y25 (see, e.g., US Pat. Publ. 2019/0175716).

Pharmaceutical compositions including the disclosed polypeptides, nucleic acids encoding the polypeptides, and/or vectors are also disclosed herein. Potential carriers include, but are not limited to, physiologically balanced culture medium, phosphate buffer saline solution, water, emulsions (e.g., oil/water or water/oil emulsions), various types of wetting agents, cryoprotective additives or stabilizers such as proteins, peptides or hydrolysates (e.g., albumin, gelatin), sugars (e.g., sucrose, lactose, sorbitol), amino acids (e.g., sodium glutamate), or other protective agents. The resulting aqueous solutions may be packaged for use as is or lyophilized. Lyophilized preparations are combined with a sterile solution prior to administration for either single or multiple dosing. The immunogenic compositions of the disclosure can contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate.

Formulated compositions, especially liquid formulations, may contain a bacteriostat to prevent or minimize degradation during storage, including but not limited to effective concentrations (usually ≤1% w/v) of benzyl alcohol, phenol, m-cresol, chlorobutanol, methylparaben, and/or propylparaben. A bacteriostat may be contraindicated for some patients; therefore, a lyophilized formulation may be reconstituted in a solution either containing or not containing such a component.

The pharmaceutical composition may optionally include an adjuvant to enhance an immune response of the host. Suitable adjuvants are, for example, toll-like receptor agonists, alum, $AlPO_4$, alhydrogel, Lipid-A and derivatives or variants thereof, oil-emulsions, saponins, neutral liposomes, liposomes containing the vaccine and cytokines, non-ionic block copolymers, and chemokines. Non-ionic block polymers containing polyoxyethylene (POE) and polyxylpropylene (POP), such as POE-POP-POE block copolymers, MPL™ (3-O-deacylated monophosphoryl lipid A; Corixa®, Hamilton, IN) and IL-12 (Genetics Institute@, Cambridge, MA), may be used as an adjuvant. These adjuvants have the advantage in that they help to stimulate the immune system in a non-specific way, thus enhancing the immune response to a pharmaceutical product. In some embodiments, an adjuvant is not required and is thus not included in the composition, or may be administered to a subject separately from the immunogenic composition.

In some embodiments, the compositions are provided as a sterile composition. The pharmaceutical composition typically contains an effective amount of a disclosed immunogen and can be prepared by techniques known to one of skill in the art. Typically, the amount of immunogen in each dose of the immunogenic composition is selected as an amount which elicits an immune response without significant, adverse side effects.

In some embodiments, the composition can be provided in unit dosage form for use to elicit an immune response in a subject, for example, to prevent or inhibit SARS-CoV-2 infection in the subject. A unit dosage form contains a suitable single preselected dosage for administration to a subject, or suitable marked or measured multiples of two or more preselected unit dosages, and/or a metering mechanism for administering the unit dose or multiples thereof.

In some embodiments, a pharmaceutical composition includes one or more nucleic acids encoding a disclosed polypeptide or a vector including one or more nucleic acids encoding a disclosed polypeptide. A therapeutically effective amount of the nucleic acid(s) can be administered to a subject in order to generate an immune response. In various embodiments, a nucleic acid encoding a biological adjuvant (such as those described above) can be cloned into same vector as a nucleic acid encoding a disclosed polypeptide, or the nucleic acid can be cloned into one or more separate vectors for co-administration. In addition, nonspecific immunomodulating factors such as Bacillus Calmette-Guerin (BCG) and levamisole can be co-administered.

III. Methods of Eliciting an Immune Response

The immunogenic polypeptides disclosed herein (such as SEQ ID NOs: 1-14 and 18, or polypeptides having at least 95% sequence identity to SEQ ID NOs: 1-14 and 18) or nucleic acids encoding the disclosed polypeptides can be administered to a subject to elicit an immune response in the subject, such as an immune response to a coronavirus (e.g., SARS-CoV-2). In some embodiments, one or more of the disclosed polypeptides (or one or more nucleic acids encoding the disclosed polypeptides) is administered to a subject with coronavirus infection or at risk of coronavirus infection. In some embodiments, the one or more immunogenic polypeptides or nucleic acids are administered in an amount sufficient to elicit an immune response to coronavirus in the subject. In particular examples, the immune response is a T cell immune response, such as a CTL response.

In particular embodiments, the methods include administering one or more (such as 1, 2, 3, or more) polypeptides or one or more (such as 1, 2, 3, or more) nucleic acids encoding the polypeptides to a subject. In some embodiments, the subject is administered a composition including one or more polypeptides or nucleic acids encoding polypeptides eliciting T-cell responses to a spectrum of diverse viruses in a subject, with the targeted diversity coverage selected to include the viral diversity that has evolved within the SARS-CoV-2 global pandemic. Thus, in some examples, the subject is administered one or more "SARS-CoV-2 Region 1" polypeptides or nucleic acids encoding polypeptides selected from sequences with at least 95% sequence identity (such as at least 95%, at least 96%, at least 97%, at least 98%, at least 99%, or even 100% sequence identity) to SEQ ID NOs: 5-7. In particular examples, the subject is administered polypeptides or nucleic acids encoding polypeptides as follows: SEQ ID NO: 5 and SEQ ID NO: 6; or SEQ ID NO: 5, SEQ ID NO: 6, and SEQ ID NO: 7; or SEQ ID NO: 5 and SEQ ID NO: 7. In other examples, the subject is administered one or more "SARS-CoV-2 Region 2" polypeptides or nucleic acids encoding polypeptides selected from sequences with at least 95% sequence identity (such as at least 95%, at least 96%, at least 97%, at least 98%, at least 99%, or even 100% sequence identity) to SEQ ID NOs: 10-12. In particular examples, the subject is administered a composition including polypeptides or nucleic acids encoding polypeptides as follows: SEQ ID NO: 10; or SEQ ID NO: 10 and SEQ ID NO: 11; or SEQ ID NO: 10, SEQ ID NO: 11, and SEQ ID NO: 12; or SEQ ID NO: 10 and SEQ ID NO: 12.

In other embodiments, the methods include administering to a subject a composition including one or more polypeptides or nucleic acids encoding polypeptides eliciting T-cell responses to a spectrum of diverse viruses in a subject, with the targeted diversity coverage selected to include Sarbecoviruses in bats, pangolins, and humans. Thus, in some examples, the subject is administered a composition including one or more "Sarbecovirus Region 1" polypeptides or nucleic acids encoding polypeptides selected from sequences with at least 95% sequence identity (such as at least 95%, at least 96%, at least 97%, at least 98%, at least 99%, or even 100% sequence identity) to SEQ ID NOs: 5, 8, and 9. In particular examples, the subject is administered a composition including polypeptides or nucleic acids encoding polypeptides as follows: SEQ ID NO: 5 and SEQ ID NO: 8; or SEQ ID NO: 5, SEQ ID NO: 8, and SEQ ID NO: 9; or SEQ ID NO: 5 and SEQ ID NO: 9. In other examples, the subject is administered a composition including one or more "Sarbecovirus Region 2" polypeptides or nucleic acids encoding polypeptides selected from sequences with at least 95% sequence identity (such as at least 95%, at least 96%, at least 97%, at least 98%, at least 99%, or even 100% sequence identity) to SEQ ID NOs: 10, 13, and 14. In particular examples, the subject is administered a composition including polypeptides or nucleic acids encoding polypeptides as follows: SEQ ID NO: 10; or SEQ ID NO: 10 and SEQ ID NO: 13; or SEQ ID NO: 10, SEQ ID NO: 13, and SEQ ID NO: 14; or SEQ ID NO: 10 and SEQ ID NO: 14.

One or more of the disclosed polypeptides or nucleic acids encoding the polypeptides (including vectors including the nucleic acid) or disclosed compositions can be administered by any means known to one of skill in the art, e.g., either locally or systemically, such as by intramuscular, subcutaneous, intradermal, or intravenous injection, but even oral, nasal, or anal administration is contemplated. In one embodiment, administration is by subcutaneous or intramuscular injection. In other embodiments, administration is intranasal or inhaled. In still other embodiments, administration is oral.

To extend the time during which the disclosed polypeptides are available to stimulate a response, the polypeptide or a nucleic acid encoding the polypeptide can be provided as an implant, an oily injection, or as a particulate system. The particulate system can be a microparticle, a microcapsule, a microsphere, a nanoparticle, a nanocapsule, or similar particle. A particulate carrier based on a synthetic polymer has been shown to act as an adjuvant to enhance the immune response, in addition to providing a controlled release.

In one embodiment, a nucleic acid encoding a disclosed immunogenic polypeptide is introduced directly into cells. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter. Typically, the nucleic acid is injected into muscle, although it can also be injected directly into other sites.

The amount of the disclosed immunogenic polypeptide, nucleic acid molecule encoding the immunogenic polypeptide, or vector including the nucleic acid molecule can vary depending upon the specific polypeptide(s), the route and protocol of administration, and the target population. An optimal amount for a particular composition can be ascertained by standard studies involving observation of responses in subjects (such as T cell responses).

In some embodiments, the immunogenic composition is administered in a single dose. In other embodiments, the immunogenic composition is administered as part of a prime-boost immunization protocol. In some examples, the same immunogenic composition is used as the prime dose and as the boost dose. It is also contemplated in some examples that the boost may be the same immunogen as another boost, or the prime. In other examples, a disclosed immunogenic composition is used as the prime dose, and a different coronavirus vaccine (such as a vaccine targeting another coronavirus protein) is administered as the boost dose. Alternatively a disclosed immunogenic composition is used as the boost dose, and a different coronavirus vaccine (such as a vaccine targeting a different coronavirus protein) is administered as the prime dose. In another example, the same immunogen is included in the prime and boost, but a different delivery system is used (for example, a different vector). It is contemplated that there can be several boosts, and that each boost can the same or different from each other and/or from the prime dose.

The prime and the boost can be administered as a single dose or multiple doses, for example, 1, 2, 3, 4, 5, 6 or more doses can be administered to a subject over days, weeks or months. In non-limiting examples, at least one boost is administered about 3-6 weeks following the prime (such as about 3 weeks, 4 weeks, 5 weeks, or 6 weeks later). Multiple boosts can also be given, such one to five, or more. Different dosages can be used in a series of sequential inoculations. For example, a relatively large dose in a primary inoculation and then a boost with relatively smaller doses. The immune response against the selected immunogen can be elicited by one or more inoculations of a subject.

In some embodiments, the subject is administered an adenovirus vector including a nucleic acid encoding one of the disclosed polypeptides. In some examples, the method includes administering a dose of about $10^5$ to about $10^{12}$ viral particles, such as about $10^5$ to about $10^7$ viral particles, about $10^6$ to about $10^8$ viral particles, about $10^7$ to about $10^8$ viral particles, about $10^8$ to about $10^{10}$ viral particles, about $10^9$ to about $10^{11}$ viral particles, or about $10^{10}$ to about $10^{12}$ viral particles. In some examples, the dose is about $1\times10^5$, about $5\times10^5$, about $1\times10^6$, about $5\times10^6$, about $1\times10^7$, about $5\times10^7$, about $1\times10^8$, about $5\times10^8$, about $1\times10^9$, about $5\times10^9$, about $1\times10^{10}$, about $5\times10^{10}$, about $1\times10^{11}$, about $5\times10^{11}$, or about $1\times10^{12}$ viral particles.

In other embodiments, the subject is administered an mRNA-lipid nanoparticle (LNP) composition encoding one of the disclosed polypeptides (see Section II). In some embodiments, the subject is administered about 1-100 µg of the mRNA-LNP (such as about 1-10 µg, about 5-15 µg, about 10-30 µg, about 20-40 µg, about 30-50 µg, about 40-60 µg, about 50-70 µg, about 60-80 µg, about 70-90 µg, or about 80-100 µg). In some examples, the dose is about 1 µg, about 2.5 µg, about 5 µg, about 7.5 µg, about 10 µg, about 12 µg, about g, about 20 µg, about 25 µg, about 30 µg, about 40 µg, about 50 µg, about 60 µg, about 70 µg, about 80 µg, about 90 µg, or about 100 µg mRNA-LNP.

In some embodiments, a disclosed polypeptide or nucleic acid is administered to the subject simultaneously with the administration of an adjuvant, for example administration of a composition that includes the polypeptide or nucleic acid and one or more adjuvants. In other embodiments, a disclosed polypeptide or nucleic acid is administered to the subject after the administration of an adjuvant and within a sufficient amount of time to elicit the immune response. In further embodiments, the subject is not administered an adjuvant.

Coronavirus (e.g., SARS-CoV-2) infection does not need to be completely inhibited for the disclosed methods to be effective. For example, eliciting an immune response can reduce or inhibit coronavirus infection by a desired amount, for example, by at least 10%, at least 20%, at least 30%, at least 40%, at least 50%, at least 60%, at least 70%, at least 80%, at least 90%, at least 95%, at least 98%, or even at least 100% (elimination or prevention of detectable infected cells), as compared to in the absence of immunization. In additional examples, coronavirus replication can be reduced or inhibited by the disclosed methods, for example, by at least 10%, at least 20%, at least 30%, at least 40%, at least 50%, at least 60%, at least 70%, at least 80%, at least 90%, at least 95%, at least 98%, or even at least 100% (elimination or prevention of detectable replication), as compared to in the absence of the immune response.

This disclosed immunogenic compositions can be used in combination with other immunogenic compositions or vaccines. In some embodiments, the disclosed immunogenic composition is used in combination (either simultaneously or sequentially) with a second coronavirus vaccine, including, a vaccine utilizing a different coronavirus protein immunogen.

EXAMPLES

The following examples are provided to illustrate certain particular features and/or embodiments. These examples should not be construed to limit the disclosure to the particular features or embodiments described.

Example 1

Identification of Conserved Regions of SARS-CoV-2 and Sarbecoviruses

An alignment of the full proteome of several hundred Sarbecoviruses was created, and then this was reduced to a set of 83 viruses that were representative of the diversity (FIG. 1). All overlapping 9-mers throughout the proteome were used to represent potential T Cell epitopes, and 9-mer coverage by the Wuhan reference strain (GenBank® Accession No. NC_045512) and also by Epigraphs were used to define the boundaries of the most conserved area.

Figure 2:
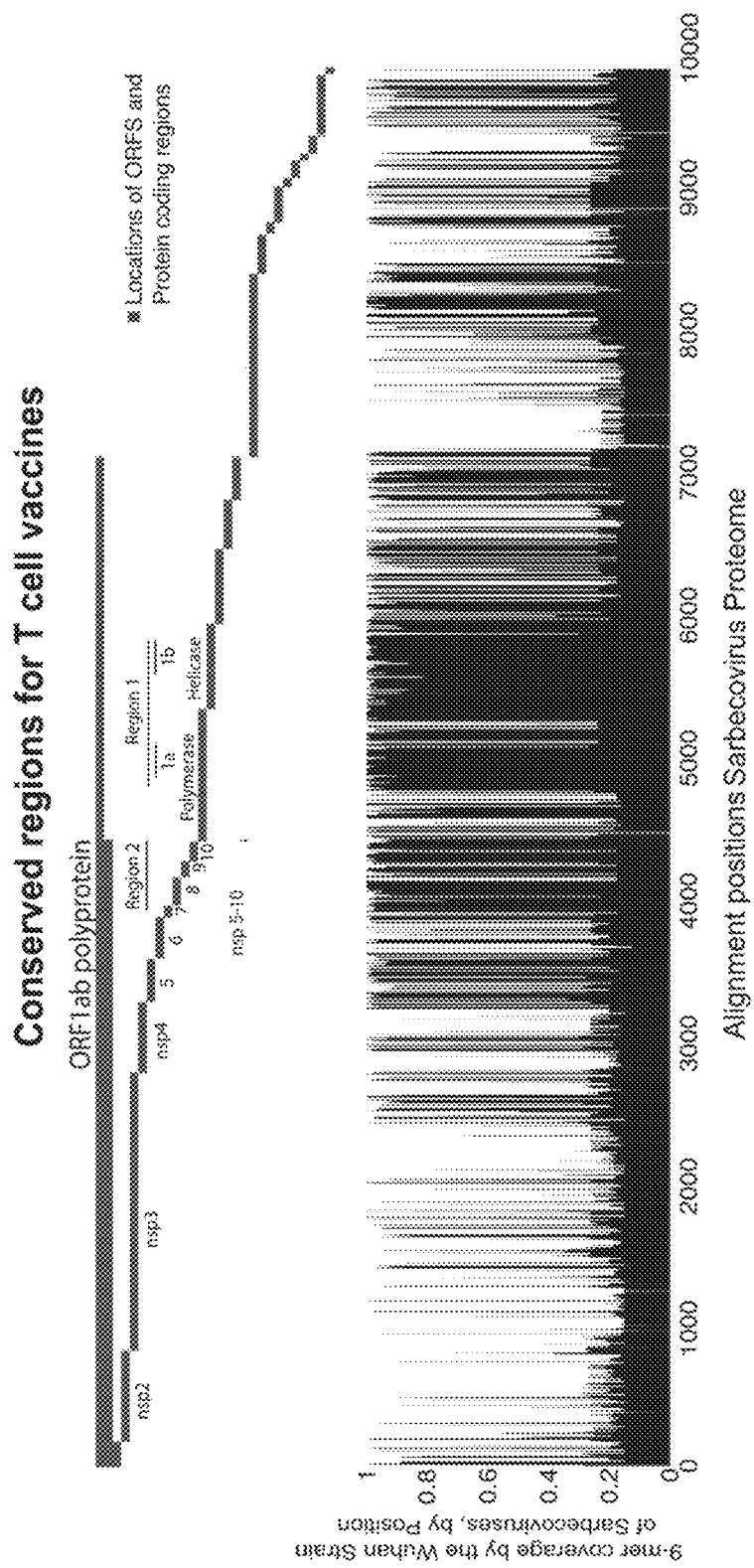
FIG. 2 is a schematic diagram illustrating 9-mer coverage in conserved regions of the betacoronavirus proteome. At the top is a schematic of all ORFs, with key proteins labeled. The frequency of perfect matches of each 9-mer to the Wuhan reference strain (GenBank® Accession No. NC-045512) is shown (bottom). Bars approaching 1 indicate nearly invariant 9-mers that match SARS-CoV-2, and dense clustering of these indicates the most conserved regions.
Figure 3:
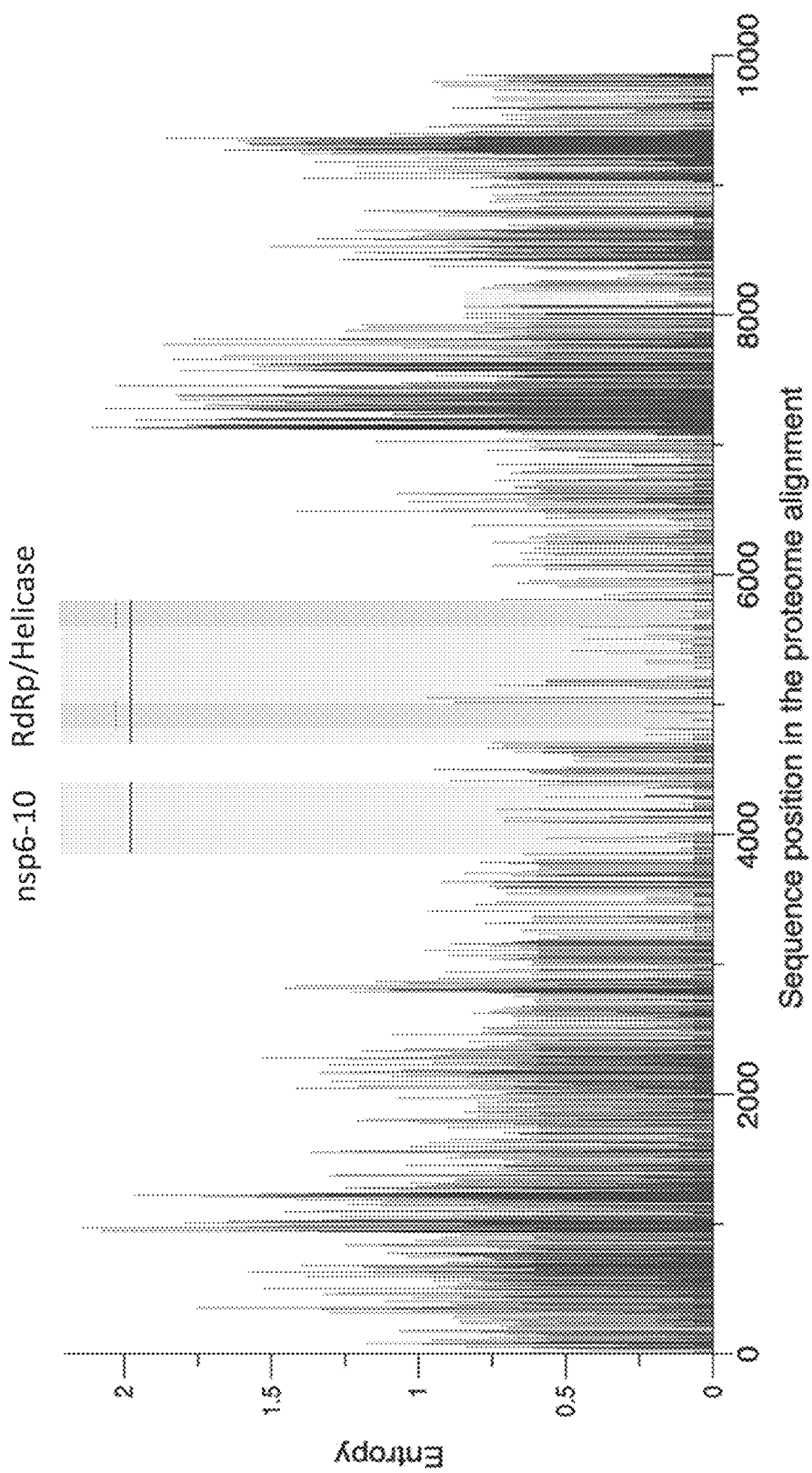
FIG. 3 is a graph showing positional entropy of amino acids in Sarbecovirus proteome alignment.

Adenovirus delivery systems are constrained to have protein inserts no more than 1200 amino acids long, so a region of the proteome of Sarbecoviruses with the greatest conservation spanning less than that upper bound in length, referred to herein as Region 1, was identified. 9-mers are stretches of 9 contiguous amino acids that are used as a surrogate for potential T cell epitopes. Epigraphs were generated to initially explore the potential for 9 mer coverage full proteome used to identify the most conserved regions from a linear CTL epitope perspective (FIG. 2) (Theiler et al., *Sci. Rep.* 6:33987, 2016; Theiler & Korber Stat Med. 2018 Jan. 30; 37(2):181-194). Per position entropy scores were used to aid in defining precise boundaries of the conserved region (FIG. 3). This yielded a protein fragment of 1,094 amino acids spanning positions of 4692-5785 in ORF1ab (positions 300-932 in RNA-dependent RNA polymerase, plus positions 1-461 in Helicase). The most conserved regions in terms of 9-mer coverage within the larger protein fragment were two stretches, Region 1a (positions 407-610 in RNA-dependent RNA polymerase), Region 1b (positions 261-461 in Helicase). The second most conserved region in the Sarbecovirus proteome alignment, positions 3848-4387 in ORF1ab, spanning the end nsp6, all of nsp7-9, and the beginning of nsp10, referred to herein as Region 2, was also identified.

Example 2

Evaluation of Immunogenicity of Adenovirus Vector Delivered SARS-CoV2 Conserved Region Immunogen Mice were immunized as shown in Table 2. A boost was administered at day 28, and samples were collected for analysis at days 28 and 56. S.pp is a stabilized Spike protein. Topt is SEQ ID NO: 1.

TABLE 2

Immunogenicity Study Plan

| Group | Vaccine Regimen |
|---|---|
| 1 | Ad26.S.pp |
| 2 | Ad26.S.pp (prime)/RhAd52.S.pp (boost) |
| 3 | Ad26.Topt |
| 4 | Ad26.Topt (prime)/RhAd52.Topt (boost) |
| 5 | Ad26.Topt (prime)/RhAd52.S.pp (boost) |
| 6 | PBS |

Figure 4:
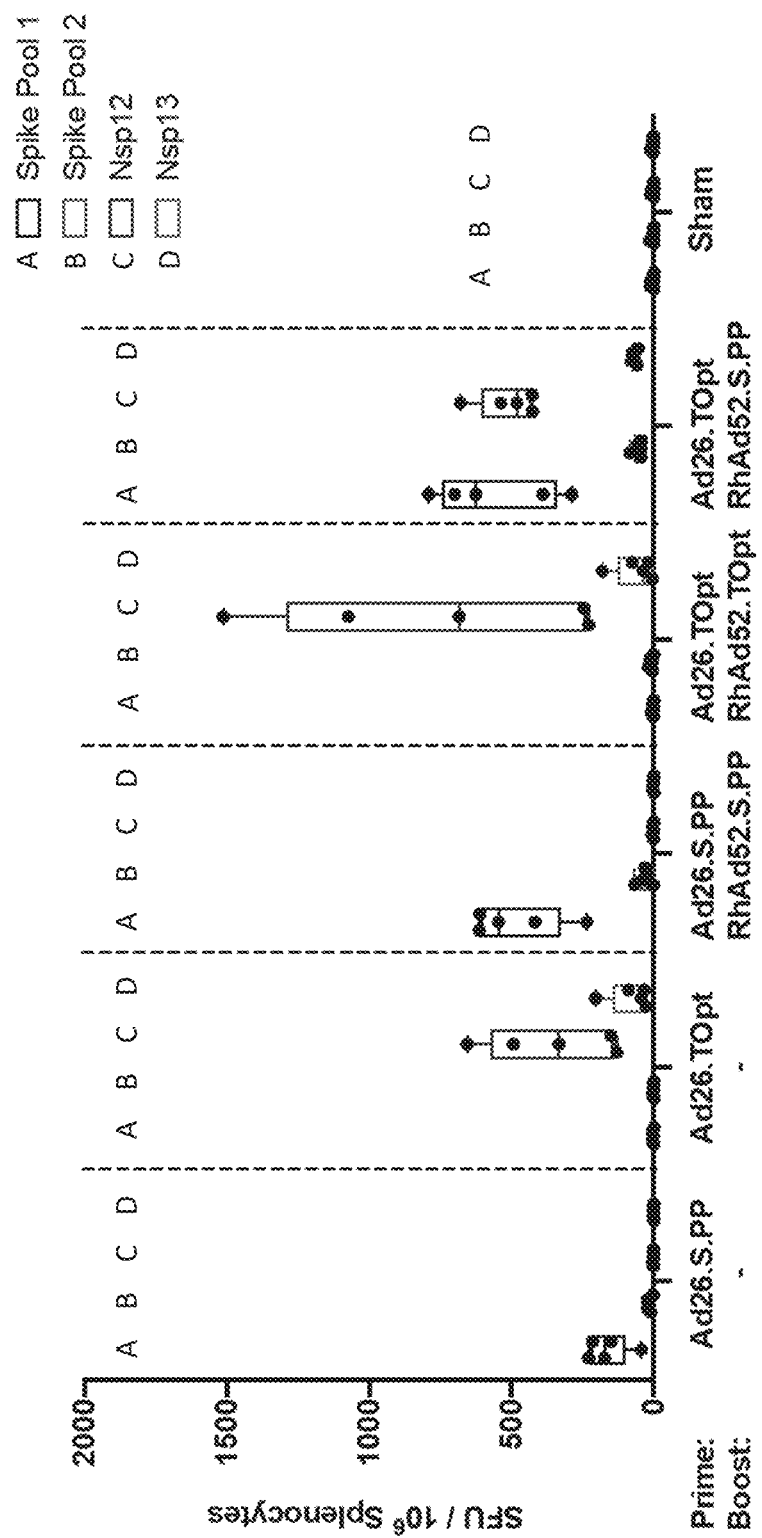
FIG. 4 illustrates interferon γ (IFNγ) response in splenocytes to the indicated proteins in mice vaccinated with the indicated protocols.
Figure 5A:
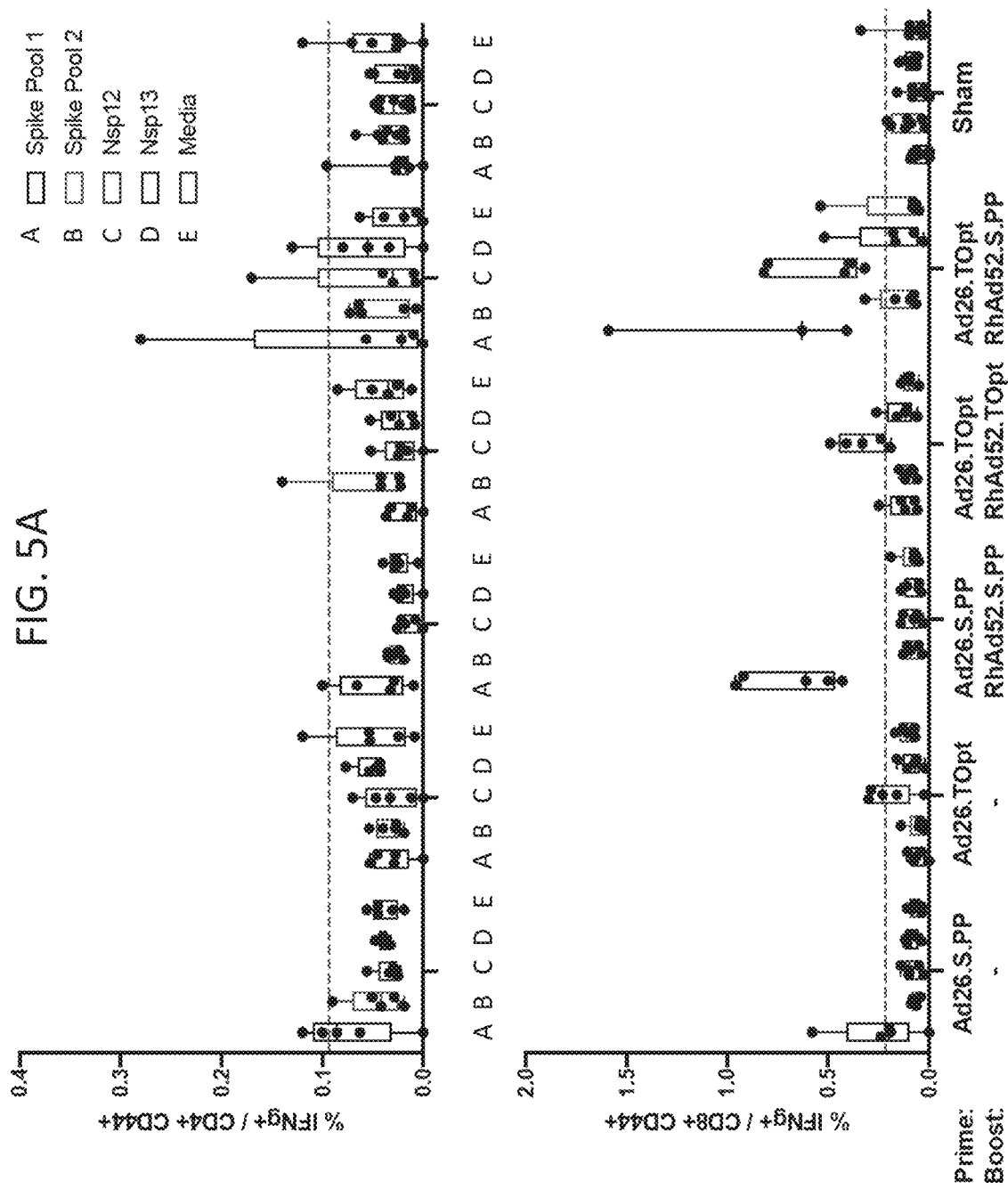
FIGS. 5A and 5B show intracellular IFNγ staining in lung (FIG. 5A) and spleen (FIG. 5B) in response to the indicated proteins in mice vaccinated with the indicated protocols.
Figure 5B:
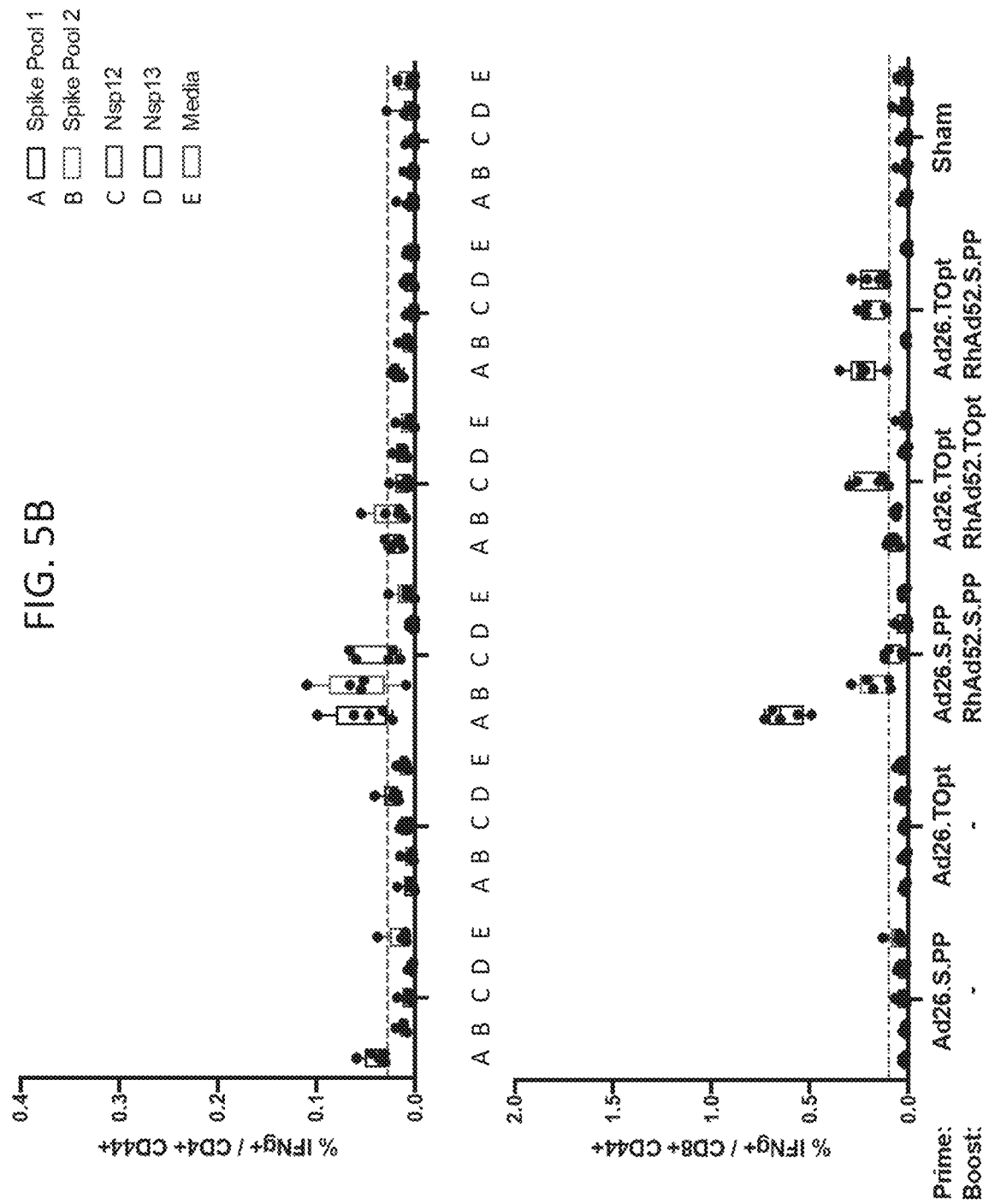

Interferon γ (IFNγ) in spleen was analyzed by ELIspot assay (FIG. 4) and IFNγ intracellular cytokine staining was analyzed in lung (FIG. 5A) and spleen (FIG. 5B).

Example 3

Evaluation of Immunogenicity of Chimpanzee Adenovirus Vector Delivered SARS-CoV2 Conserved Region Immunogen 6wp HeLa cells were infected with MOI 10 ($1\times10^7$ IU) of ChAdOx1.COVconsv or ChAdOx2.COVconsv in 1 ml volume for 2 h. COVconsv has the amino acid sequence of SEQ ID NO: 18. D10 was added and incubated for 24 h. Cells were lysed in 200 ml M-PER+HALT. Samples (10 μl inclusive of 4× sample buffer and 10× reducing agent) were run on 3-8% Tris Acetate gel and analysed by Western blot and Coomassie staining (FIGS. 6A and 6B). Full-size proteins were readily expressed from both vaccines were readily detectable. Note that the COVconsv protein has a Pk tag at its C-terminus recognized by mAb 336, which facilitated the protein detection. Mice were immunized intramuscularly with one dose of ChAdOx1.COVconsv. A group of 3 BALB/c mice were immunized i.m. with $10^8$ infectious units and sacrificed 9 day later. IFNγ ELISpot assay was performed on pooled splenocytes using 201 peptides 18/10 from across the COVconsv sequence.

Figure 7:
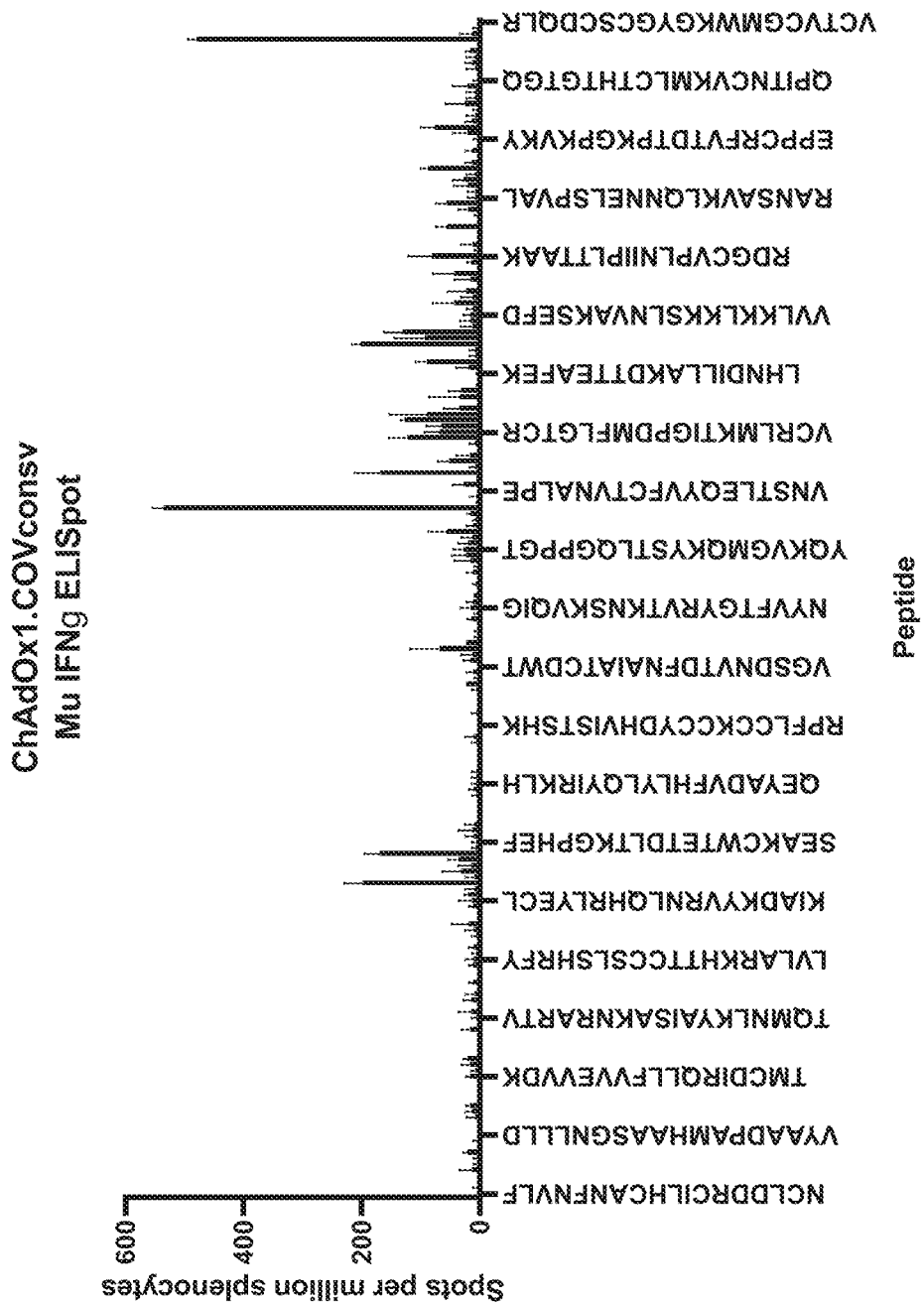
FIG. 7 is a graph showing IFNγ ELISpot assay results of immune BALB/c splenocytes tested against 18-mer peptides overlapping by 11 amino acids spanning the entire the COVconsv (region 1 and region 2) immunogen 9 days after a single intramuscular vaccination. Every $10^{th}$ peptide is listed.

A broad T cell response was induced dominated by two strong specificities and further five medium strong peptides (FIG. 7). These T cell responses can complement antibodies recognizing other coronavirus proteins elicited by currently available vaccines, and may further improve virus control and perhaps help resolve long COVID symptoms.

Example 4

Evaluation of Immunogenicity of SARS-CoV2 Conserved Region Immunogen Using Lipid Nanoparticle mRNA Delivery Balb/c or C57/Bl6 mice (8-10 weeks old) were immunized with nucleoside-modified mRNA-LNP vaccines encoding conserved regions of CoVs (SEQ ID NOs: 15-17). Ten days later, spleen cells were obtained and stimulated with peptide pools encompassing the immunogen used to vaccinate. Multicolor flow cytometry was performed. Data show CD4+ and CD8+ T cell responses (FIGS. 8A-8F).

Example 5

Evaluation of Efficacy of Adenovirus Delivery in SARS-CoV-2 Mouse Adapted Virus Model This example describes particular methods that can be used to evaluate vaccine efficacy. However, one skilled in the art will appreciate that methods that deviate from these specific methods can also be used. In addition, alternative coronavirus polypeptides (such as one or more of the polypeptides described herein) can be encoded by the adenovirus construct(s).

Figure 9:
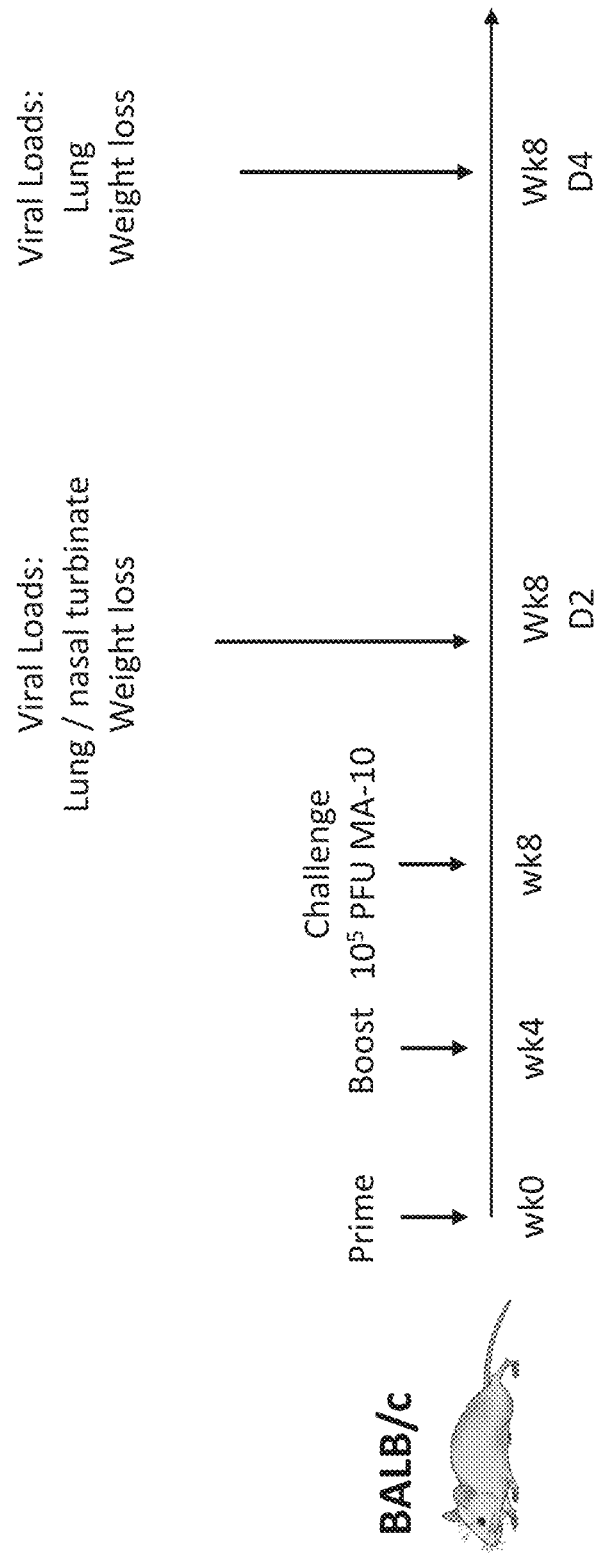
FIG. 9 is a schematic diagram showing an exemplary protocol for testing a disclosed immunogenic composition.

In some examples, adenovirus delivery of a conserved region polypeptide is tested in a mouse-adapted model of SARS-CoV-2. An exemplary protocol is shown in FIG. 9. The vaccination regimen is provided in Table 3. The adenovirus vectors are as described in Example 2.

TABLE 3

Vaccination regimen

| Group | Week 0 (prime) | Week 4 (boost) |
|---|---|---|
| 1 | Sham | Sham |
| 2 | $10^9$ vp RhAd52.S.PP | $10^9$ vp RhAd52.S.PP |
| 3 | — | $10^7$ vp RhAd52.S.PP |
| 4 | $10^7$ vp RhAd52.S.PP | — |
| 5 | $10^9$ vp RhAd52.TOpt | $10^9$ vp RhAd52.Topt |
| 6 | $10^7$ vp RhAd52.S.PP + $10^{\sim}9$ vp RhAd52.TOpt | $10^9$ vp RhAd52.TOpt |
| 7 | $10^9$ vp RhAd52.TOpt | $10^7$ vp RhAd52.S.PP + $10^{\sim}9$ vp RhAd52.TOpt |

Four weeks following the boost, mice are challenged with SARS-CoV-2 intranasally and assessed for viral load and weight loss 2 days and 4 days later. A decrease in viral load or weight loss compared to a control indicates efficacy of the immunization.

Example 6

Epigraph Sequence Development

Initially it was important to resolve that the regions of high potential epitope identified in Example 1 would be immunogenic using the COVID-19 vaccine delivery strategies; this proved to be the case using the SARS-CoV-2 ancestral sequence as a prototype (Examples 2-4). As even the most conserved regions of the virus show some variability, epigraph sequences were designed spanning Region 1 and Region 2. These Epigraphs were designed serially using the SARS-CoV-2 sequence as a baseline, and provide complementary sequences to provide 9-mer coverage using either the Sarbecovirus alignment for a pan-Sarbecovirus vaccine (FIG. 1), or a global alignment from GISAID for a SARS-CoV-2 vaccine that best covers known pandemic diversity based on ~461,092 sequences sampled from GISAID on Mar. 24, 2021. These epigraphs can be utilized in a combination of 2 or 3 vaccine antigens to prevent escape in SARS-CoV-2 infections and increase breadth of coverage: either (i) the Wuhan reference plus one epigraph, for a bivalent vaccine, or (ii) the Wuhan reference plus two epigraphs for a trivalent vaccine.

In the sequences provided herein, the first epigraph is complementary to the ancestral Wuhan form, and is an artificial sequence designed to provide optimal 9-mer diversity coverage of the input sequence alignment when combined with the Wuhan form; the second epigraph is complementary to the combination of the first two, and provides potentially optimal coverage for a trivalent vaccine.

Example 7

Region 1 Epigraphs

Epigraphs were designed to best cover known global SARS-CoV-2 9-mer diversity in conserved region 1 (SEQ ID NO: 5), as maintained in GISAID, based on the Mar. 24, 2021, full proteome SARS-COV-2 global alignment. The cov.lanl.gov FULL.ORFlab.protein.Human.fasta alignment on that day included 461,092 sequences.

Figure 10:
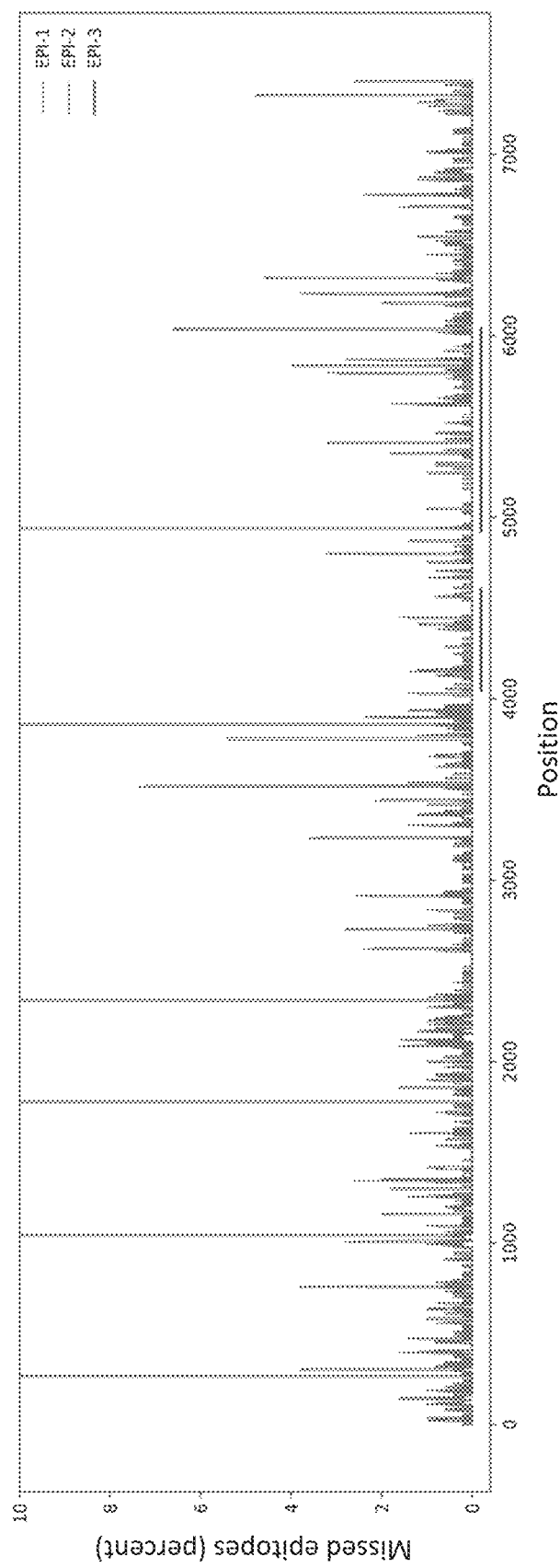
FIG. 10 is a plot showing the percent of missed 9-mers, or potential T cell epitopes, using the Wuhan reference strain (GenBank® Accession No. NC_045512) alone (EPI-1; GenBank® Accession No. NC_045512), or using the combination of the Wuhan sequence plus one epigraph (EPI-2; SEQ ID NO: 6) or plus two epigraphs (EPI-3; SEQ ID NO: 6 and SEQ ID NO: 7), spanning the lab polyprotein. EPI-2 provides a substantial increase in coverage. Region 2 is very highly conserved to date among pandemic strains. Region 1, despite being the most conserved region across Sarbecoviruses, has both some very highly conserved regions and some modestly conserved regions.

Two epigraphs were selected: Region 1 SARS-CoV-2-EG-2.1 (SEQ ID NO: 6) and Region 1 SARS-CoV-2-EG-2.2 (SEQ ID NO: 7). The percentage of missed 9-mers (potential T cell epitopes) using SEQ ID NO: 5 alone, SEQ ID NO: 5 plus SEQ ID NO: 6, or all of SEQ ID NOs: 5-7 (FIG. 10). The combination of SEQ ID NO: 5 and SEQ ID NO: 6 provided a substantial increase in coverage; addition of SEQ ID NO: 7 provided an additional improvement (Table 4), with less than 0.1% of missed 9-mers (>99.9% coverage). An alignment of SEQ ID NOs: 1, 6, and 7 is shown in FIG. 11.

TABLE 4

Potential T cell epitopes missed by combinations of Region 1 SARS-CoV2 polypeptides (percentage) across SARS-CoV-2

|  | All (A) | Positions 4044-4605 (B) | Positions 4921-6041 (C) | All except B and C |
|---|---|---|---|---|
| Region 1 | 0.5959 | 0.2750 | 1.1459 | 0.5168 |
| Region 1 + Region 1 SARS-CoV-2-EG-2.1 | 0.1397 | 0.1177 | 0.0904 | 0.1518 |
| Region 1 + Region 1 SARS-CoV-2-EG-2.1 + Region 1 SARS-CoV-2-EG-2.2 | 0.0931 | 0.0683 | 0.0584 | 0.1026 |

Figure 12:
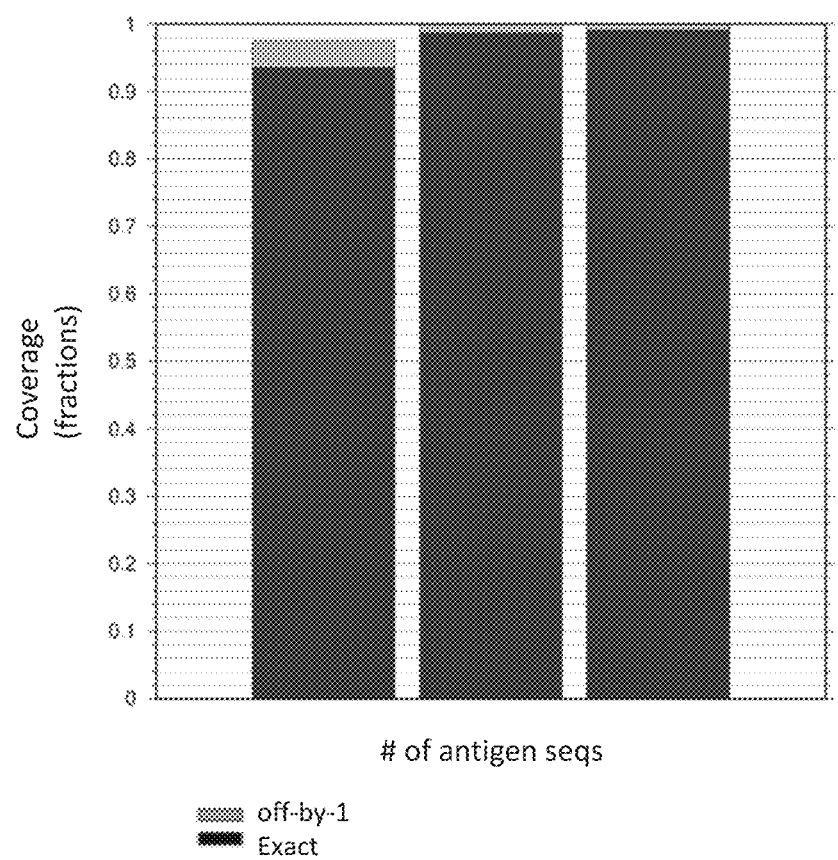
FIG. 12 is a graph showing coverage of pan-Sarbecovirus Region 1 of Wuhan alone (SEQ ID NO: 5, left), Wuhan Region 1 plus Region 1 SARBECO-EG-2.1 (SEQ ID NO: 8, center), and Wuhan Region 1 plus Region 1 SARBECO-EG-2.1, and Region 1 SARBECO-EG-2.2 (SEQ ID NO: 9, right).

Region 1 is extremely conserved among Sarbecoviruses, such that the Wuhan strain alone captures much of the diversity in the Sarbecovirus aligned sequences (FIG. 1). A single epigraph (SEQ ID NO: 8) provided additional coverage given the diversity of the input sample; the addition of the second epigraph (SEQ ID NO: 9) provides an incremental benefit (Table 5 and FIG. 12). An alignment of SEQ ID NOs: 1, 8, and 9 is shown in FIG. 13.

TABLE 5

Sarbecovirus coverage for Region 1

|  | Coverage (exact) | Coverage (offby ≤1) |
|---|---|---|
| Wuhan (SEQ ID NO: 5) | 0.935196 | 0.975149 |
| Wuhan plus epigraph 1 (SEQ ID NO: 5 and SEQ ID NO: 8) | 0.987062 | 0.999574 |
| Wuhan plus epigraphs 1 and 2 (SEQ ID NOs: 5, 8, and 9) | 0.990941 | 0.999574 |

Example 8

Region 2 Epigraphs

Figure 14:
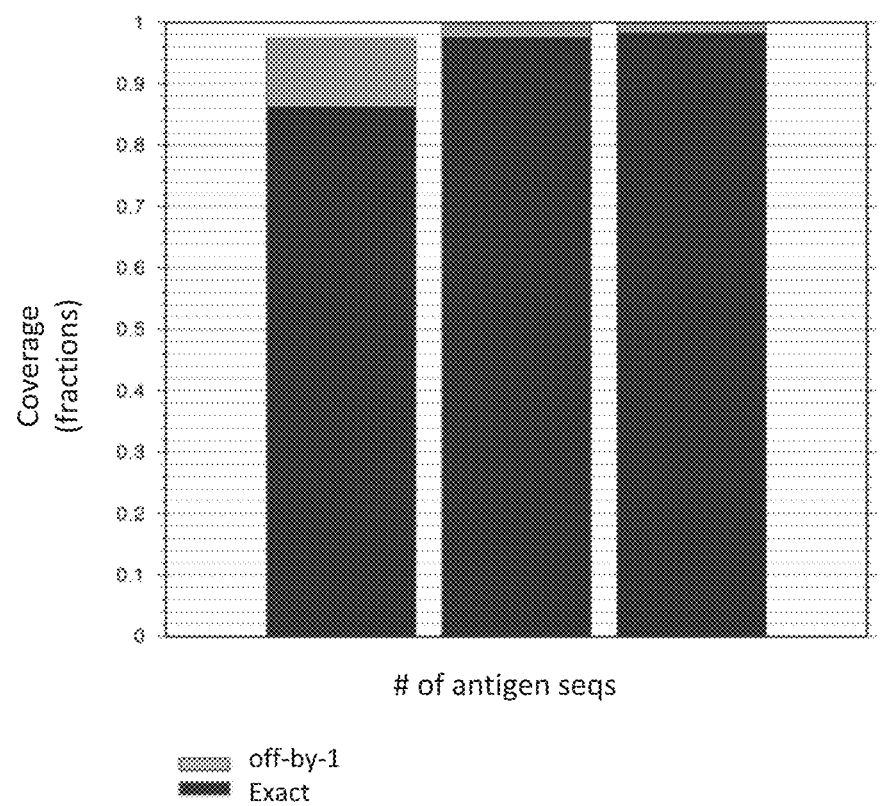
FIG. 14 is a graph showing coverage of pan-Sarbecovirus Region 2 of Wuhan alone (SEQ ID NO: 10, left), Wuhan Region 2 plus Region 2 SARBECO-EG-2.1 (SEQ ID NO: 13, center), and Wuhan Region 2 plus Region 2 SARBECO-EG-2.1, and region 2 SARBECO-EG-2.2 (SEQ ID NO: 14, right).

Region 2 was the second most conserved long stretch in the Sarbecovirus proteome. It was defined to be ~600 amino acids, which is compatible with RNA (such as mRNA-LNP) delivery systems. Epigraphs to best cover known global SARS-CoV-2 9-mer diversity and in Sarbecoviruses were designed as described above. The SARS-CoV-2 epigraphs are SEQ ID NOs: 11 and 12, and pan-Sarbecovirus epigraphs are SEQ ID NOs: 13 and 14. Table 6 and FIG. 14 summarize the Sarbecovirus coverage for Region 2 provided by the Wuhan reference sequence (SEQ ID NO: 10), and one or two of the pan-Sarbecovirus epigraphs. Alignments of the sequences are shown in FIGS. 15 and 16.

TABLE 6

Sarbecovirus coverage for Region 2

|  | Coverage (exact) | Coverage (offby ≤1) |
|---|---|---|
| Wuhan (SEQ ID NO: 10) | 0.862376 | 0.974106 |
| Wuhan plus epigraph 1 (SEQ ID NO: 10 and SEQ ID NO: 13) | 0.975516 | 0.996945 |
| Wuhan plus epigraphs 1 and 2 (SEQ ID NOs: 10, 13, and 14) | 03982260 | 0.998355 |

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. An immunogenic composition comprising:
   one or more polypeptides with at least 99% sequence identity to any one of SEQ ID NOs: 11-14; or a nucleic acid encoding a polypeptide with at least 99% sequence identity to any one of SEQ ID NOs: 11-14; and
   a pharmaceutically acceptable carrier.

2. The immunogenic composition of claim 1, wherein the one or more polypeptides comprise or consist of the amino acid sequence of any one of SEQ ID NOs: 11-14.

3. The immunogenic composition of claim 1, wherein the one or more polypeptides comprise:
   SEQ ID NO: 11;
   SEQ ID NO: 12;
   SEQ ID NO: 13;
   SEQ ID NO: 14;
   SEQ ID NO: 11 and SEQ ID NO: 12;
   SEQ ID NO: 11 and SEQ ID NO: 13;
   SEQ ID NO: 11 and SEQ ID NO: 14;
   SEQ ID NO: 12 and SEQ ID NO: 13;
   SEQ ID NO: 12 and SEQ ID NO: 14;
   SEQ ID NO: 13 and SEQ ID NO: 14;
   SEQ ID NO: 11, SEQ ID NO: 12, and SEQ ID NO: 13;
   SEQ ID NO: 11, SEQ ID NO: 12, and SEQ ID NO: 14;
   SEQ ID NO: 11, SEQ ID NO: 13, and SEQ ID NO: 14; or
   SEQ ID NO: 12, SEQ ID NO: 13, and SEQ ID NO: 14.

4. The immunogenic composition of claim 1, wherein the one or more polypeptides comprise two or more polypeptides, and at least one of the two or more polypeptides further comprise SEQ ID NO: 10.

5. The immunogenic composition of claim 4, wherein the two or more polypeptides comprise:
   SEQ ID NO: 10 and SEQ ID NO: 11;
   SEQ ID NO: 10 and SEQ ID NO: 12;
   SEQ ID NO: 10 and SEQ ID NO: 13;
   SEQ ID NO: 10 and SEQ ID NO: 14;
   SEQ ID NO: 10, SEQ ID NO: 11, and SEQ ID NO: 12;
   SEQ ID NO: 10, SEQ ID NO: 11, and SEQ ID NO: 13;
   SEQ ID NO: 10, SEQ ID NO: 11, and SEQ ID NO: 14;
   SEQ ID NO: 10, SEQ ID NO: 12, and SEQ ID NO: 13;
   SEQ ID NO: 10, SEQ ID NO: 12, and SEQ ID NO: 14; or
   SEQ ID NO: 10, SEQ ID NO: 13, and SEQ ID NO: 14.

6. The immunogenic composition of claim 1, wherein the nucleic acid is an mRNA and the mRNA is formulated in a lipid nanoparticle.

7. The immunogenic composition of claim 6, wherein the lipid nanoparticle comprises ALC-0315.

8. A vector comprising a nucleic acid encoding a polypeptide with at least 99% sequence identity to any one of SEQ ID NOs: 11-14.

9. The vector of claim 8, wherein the polypeptide comprises or consists of the amino acid sequence of any one of SEQ ID NOs: 11-14.

10. The vector of claim 8, wherein the vector is an adenovirus vector.

11. The vector of claim 10, wherein the adenovirus vector is an Ad5, Ad26, Ad35, or Ad52 adenovirus vector or a ChAdOx1 or ChAdOx2 adenovirus vector.

12. An immunogenic composition, comprising the vector of claim 8 and a pharmaceutically acceptable carrier.

13. A method of eliciting an immune response to a coronavirus in a subject, comprising administering to the subject the immunogenic composition of claim 1, thereby eliciting an immune response to the coronavirus.

14. The method of claim 13, wherein the one or more polypeptides comprise:
SEQ ID NO: 11;
SEQ ID NO: 12;
SEQ ID NO: 13;
SEQ ID NO: 14;
SEQ ID NO: 11 and SEQ ID NO: 12;
SEQ ID NO: 11 and SEQ ID NO: 13;
SEQ ID NO: 11 and SEQ ID NO: 14;
SEQ ID NO: 12 and SEQ ID NO: 13;
SEQ ID NO: 12 and SEQ ID NO: 14;
SEQ ID NO: 13 and SEQ ID NO: 14;
SEQ ID NO: 11, SEQ ID NO: 12, and SEQ ID NO: 13;
SEQ ID NO: 11, SEQ ID NO: 12, and SEQ ID NO: 14;
SEQ ID NO: 11, SEQ ID NO: 13, and SEQ ID NO: 14; or
SEQ ID NO: 12, SEQ ID NO: 13, and SEQ ID NO: 14.

15. The method of claim 13, wherein the one or more polypeptides comprise two or more polypeptides, and at least one of the two or more polypeptides further comprise SEQ ID NO: 10.

16. The method of claim 15, wherein the two of more polypeptides comprise:
SEQ ID NO: 10 and SEQ ID NO: 11;
SEQ ID NO: 10 and SEQ ID NO: 12;
SEQ ID NO: 10 and SEQ ID NO: 13;
SEQ ID NO: 10 and SEQ ID NO: 14;
SEQ ID NO: 10, SEQ ID NO: 11, and SEQ ID NO: 12;
SEQ ID NO: 10, SEQ ID NO: 11, and SEQ ID NO: 13;
SEQ ID NO: 10, SEQ ID NO: 11, and SEQ ID NO: 14;
SEQ ID NO: 10, SEQ ID NO: 12, and SEQ ID NO: 13;
SEQ ID NO: 10, SEQ ID NO: 12, and SEQ ID NO: 14; or
SEQ ID NO: 10, SEQ ID NO: 13, and SEQ ID NO: 14.

17. The method of claim 13, wherein the nucleic acid encoding the polypeptide is mRNA.

18. The method of claim 17, wherein the mRNA is formulated in a lipid nanoparticle, optionally wherein the lipid nanoparticle comprises ALC-0315.

19. The method of claim 13, wherein administering the nucleic acid encoding the polypeptide comprises administering an adenovirus vector comprising the nucleic acid.

20. The method of claim 19, wherein the adenovirus vector is an Ad5, Ad26, Ad35, or Ad52 adenovirus vector or a ChAdOx1 or ChAdOx2 adenovirus vector.

* * * * *

SEQUENCE LISTING

```
Sequence total quantity: 18
SEQ ID NO: 1            moltype = AA  length = 1094
FEATURE                 Location/Qualifiers
REGION                  1..1094
                        note = SARS-CoV-2 RNA-dependent RNA polymerase/helicase
                        region
source                  1..1094
                        mol_type = protein
                        organism = synthetic construct
SEQUENCE: 1
NCLDDRCILH CANFNVLFST VFPPTSFGPL VRKIFVDGVP FVVSTGYHFR ELGVVHNQDV   60
NLHSSRLSFK ELLVYAADPA MHAASGNLLL DKRTTCFSVA ALTNNVAFQT VKPGNFNKDF  120
YDFAVSKGFF KEGSSVELKH FFFAQDGNAA ISDYDYYRYN LPTMCDIRQL LFVVEVVDKY  180
FDCYDGGCIN ANQVIVNNLD KSAGFPFNKW GKARLYYDSM SYEDQDALFA YTKRNVIPTI  240
TQMNLKYAIS AKNRARTVAG VSICSTMTNR QFHQKLLKSI AATRGATVVI GTSKFYGGWH  300
NMLKTVYSDV ENPHLMGWDY PKCDRAMPNM LRIMASLVLA RKHTTCCSLS HRFYRLANEC  360
AQVLSEMVMC GGSLYVKPGG TSSGDATTAY ANSVFNICQA VTANVNALLS TDGNKIADKY  420
VRNLQHRLYE CLYRNRDVDT DFVNEFYAYL RKHFSMMILS DDAVVCFNST YASQGLVASI  480
KNFKSVLYYQ NNVFMSEAKC WTETDLTKGP HEFCSQHTML VKQGDDYVYL PYPDPSRILG  540
AGCFVDDIVK TDGTLMIERF VSLAIDAYPL TKHPNQEYAD VFHLYLQYIR KLHDELTGHM  600
```

```
LDMYSVMLTN DNTSRYWEPE FYEAMYTPHT VLQAVGACVL CNSQTSLRCG ACIRRPFLCC  660
KCCYDHVIST SHKLVLSVNP YVCNAPGCDV TDVTQLYLGG MSYYCKSHKP PISFPLCANG  720
QVFGLYKNTC VGSDNVTDFN AIATCDWTNA GDYILANTCT ERLKLFAAET LKATEETFKL  780
SYGIATVREV LSDRELHLSW EVGKPRPPLN RNYVFTGYRV TKNSKVQIGE YTFEKGDYGD  840
AVVYRGTTTY KLNVGDYFVL TSHTVMPLSA PTLVPQEHYV RITGLYPTLN ISDEFSSNVA  900
NYQKVGMQKY STLQGPPGTG KSHFAIGLAL YYPSARIVYT ACSHAAVDAL CEKALKYLPI  960
DKCSRIIPAR ARVECFDKFK VNSTLEQYVF CTVNALPETT ADIVVFDEIS MATNYDLSVV 1020
NARLRAKHYV YIGDPAQLPA PRTLLTKGTL EPEYFNSVCR LMKTIGPDMF LGTCRRCPAE 1080
IVDTVSALVY DNKL                                                  1094

SEQ ID NO: 2              moltype = AA   length = 204
FEATURE                   Location/Qualifiers
REGION                    1..204
                          note = SARS-CoV-2 RNA-dependent RNA polymerase region
source                    1..204
                          mol_type = protein
                          organism = synthetic construct
SEQUENCE: 2
FQTVKPGNFN KDFYDFAVSK GFFKEGSSVE LKHFFFAQDG NAAISDYDYY RYNLPTMCDI  60
RQLLFVVEVV DKYFDCYDGG CINANQVIVN NLDKSAGFPF NKWGKARLYY DSMSYEDQDA 120
LFAYTKRNVI PTITQMNLKY AISAKNRART VAGVSICSTM TNRQFHQKLL KSIAATRGAT 180
VVIGTSKFYG GWHNMLKTVY SDVE                                       204

SEQ ID NO: 3              moltype = AA   length = 201
FEATURE                   Location/Qualifiers
REGION                    1..201
                          note = SARS-CoV-2 helicase region
source                    1..201
                          mol_type = protein
                          organism = synthetic construct
SEQUENCE: 3
EFSSNVANYQ KVGMQKYSTL QGPPGTGKSH FAIGLALYYP SARIVYTACS HAAVDALCEK  60
ALKYLPIDKC SRIIPARARV ECFDKFKVNS TLEQYVFCTV NALPETTADI VVFDEISMAT 120
NYDLSVVNAR LRAKHYVYIG DPAQLPAPRT LLTKGTLEPE YFNSVCRLMK TIGPDMFLGT 180
CRRCPAEIVD TVSALVYDNK L                                          201

SEQ ID NO: 4              moltype = AA   length = 538
FEATURE                   Location/Qualifiers
REGION                    1..538
                          note = SARS-CoV-2 nsp6-10 region
source                    1..538
                          mol_type = protein
                          organism = synthetic construct
SEQUENCE: 4
GGKPCIKVAT VQSKMSDVKC TSVVLLSVLQ QLRVESSSKL WAQCVQLHND ILLAKDTTEA  60
FEKMVSLVLL SMQGAVDINK LCEEMLDNRA TLQAIASEFS SLPSYAAFAT AQEAYEQAVA 120
NGDSEVVLKK LKKSLNVAKS EFDRDAAMQR KLEKMADQAM TQMYKQARSE DKRAKVTSAM 180
QTMLFTMLRK LDNDALNNII NNARDGCVPL NIIPLTTAAK LMVVIPDYNT YKNTCDGTTF 240
TYASALWEIQ QVVDADSKIV QLSEISMDNS PNLAWPLIVT ALRANSAVKL QNNELSPVAL 300
RQMSCAAGTT QTACTDDNAL AYYNTTKGGR FVLALLSDLQ DLKWARFPKS DGTGTIYTEL 360
EPPCRFVTDT PKGPKVKYLY FIKGLNNLNR GMVLGSLAAT VRLQAGNATE VPANSTVLSF 420
CAFAVDAAKA YKDYLASGGQ PITNCVKMLC THTGTGQAIT VTPEANMDQE SFGGASCCLY 480
CRCHIDHPNP KGFCDLKGKY VQIPTTCAND PVGFTLKNTV CTVCGMWKGY GCSCDQLR   538

SEQ ID NO: 5              moltype = AA   length = 1094
FEATURE                   Location/Qualifiers
REGION                    1..1094
                          note = Modified RNA-dependent RNA polymerase and helicase
                           (region 1)
source                    1..1094
                          mol_type = protein
                          organism = synthetic construct
SEQUENCE: 5
NCLDDRCILH CANFNVLFST VFPPTSFGPL VRKIFVDGVP FVVSTGYHFR ELGVVHNQDV  60
NLHSSRLSFK ELLVYAADPA MHAASGNLLL DKRTTCFSVA ALTNNVAFQT VKPGNFNKDF 120
YDFAVSKGFF KEGSSVELKH FFFAQDGNAA ISDYDYYRYN LPTMCDIRQL LFVVEVVDKY 180
FDCYDGGCIN ANQVIVNNLD KSAGFPFNKW GKARLYYDSM SYEDQDALFA YTKRNVIPTI 240
TQMNLKYAIS AKNRARTVAG VSICSTMTNR QFHQKLLKSI AATRGATVVI GTSKFYGGWH 300
NMLKTVYSDV ENPHLMGWDY PKCDRAMPNM LRIMASLVLA RKHTTCCSLS HRFYRLANEC 360
AQVLSEMVMC GGSLYVKPGG TSSGDATTAY ANSVFNICQA VTANVNALLS TDGNKIADKY 420
VRNLQHRLYE CLYRNRDVDT DFVNEFYAYL RKHFSMMILS AAAVVCFNST YASQGLVASI 480
KNFKSVLYYQ NNVFMSEAKC WTETDLTKGP HEFCSQHTML VKQGDDYVYL PYPDPSRILG 540
AGCFVDDIVK TDGTLMIERF VSLAIDAYPL TKHPNQEYAD VFHLYLQYIR KLHDELTGHM 600
LDMYSVMLTN DNTSRYWEPE FYEAMYTPHT VLQAVGACVL CNSQTSLRCG ACIRRPFLCC 660
KCCYDHVIST SHKLVLSVNP YVCNAPGCDV TDVTQLYLGG MSYYCKSHKP PISFPLCANG 720
QVFGLYKNTC VGSDNVTDFN AIATCDWTNA GDYILANTCT ERLKLFAAET LKATEETFKL 780
SYGIATVREV LSDRELHLSW EVGKPRPPLN RNYVFTGYRV TKNSKVQIGE YTFEKGDYGD 840
AVVYRGTTTY KLNVGDYFVL TSHTVMPLSA PTLVPQEHYV RITGLYPTLN ISDEFSSNVA 900
NYQKVGMQKY STLQGPPGTG KSHFAIGLAL YYPSARIVYT ACSHAAVDAL CEKALKYLPI 960
```

```
DKCSRIIPAR ARVECFDKFK VNSTLEQYVF CTVNALPETT ADIVVFDEIS MATNYDLSVV  1020
NARLRAKHYV YIGDPAQLPA PRTLLTKGTL EPEYFNSVCR LMKTIGPDMF LGTCRRCPAE  1080
IVDTVSALVY DNKL                                                   1094

SEQ ID NO: 6            moltype = AA  length = 1094
FEATURE                 Location/Qualifiers
REGION                  1..1094
                        note = Optimized region 1 polypeptide (region 1 EG-2.1)
source                  1..1094
                        mol_type = protein
                        organism = synthetic construct
SEQUENCE: 6
NCSDDRCILH CSNFNVLFST VFPLTSFGPL VRKMFVDGVP FVISTGYHFR ELGVLHNQDV  60
NLHSSRLSFN ELLVYAADPA MHTASGNLLL DKRTMCFSVA ALTNNVAFQT VRPGNFNKDF  120
YDFVVSKGFF KEGSFVELKH FFFAQDGNAV ISDYDYYRYN LPTICDIRQL LFVVEVVDNY  180
FDCYDGGCIN ASQVIVNNLD KSAGPPFNKW GKARFYYDSM SYEDQDALFV YTKRNVIPTI  240
TQMNLKYAIS AKNRSRTVAG VSIFSTMTNR QFYQKLLKSI ASTRGATVVI GISKFYGGWH  300
NMLKTIYSDV ENPHFMGWDY PKCDRAMPNI LRIMASLVFA RKHTTCCILS HRFYRLSNEC  360
AQVLSEIVMC GGSLYVKPGG TSSGEATTAY ANSVFNICQS VTANVNALLS TDGNKIADKY  420
IRNLQHRLYA CLYRNRDVDI DFVNEFYAYL RKHFSIMILS AAAVVCVNST YASQGLLASI  480
KNFKSVLYYQ NNIFMSEAKC WTEIDLTKGP HEFCSQHTML VKHGDDYVYL SYPDPSRILG  540
AGCFVDDILK TDGTLMIERF VSLAIDAYPL IKHPNQEYAD VFRLYLQYIR KLHYELTGHM  600
LDIYSVMLTN DNTLRYWEPE FYDAMYTPHT VLQAVGVCVL CNSQTSLRCG VCIRRPFLCC  660
ECCYDHVIST LHKLVLSVNP YVCNALGCDV TDVTQLYLGG MNYYCKSHKP SISFPLCANG  720
HVFGLYKNTC FGSDNVTDFN AIATCDWINA GDYILANTCI ERLKLFAAET LKAIEETFKL  780
SYGIAIVREV LSDRELYLSW EVGKPRPPFN RNYVFTGYRL TKNSKVQIGD YTFEKGDYVD  840
AVVYRGTTTY RLNVGDYFVL TSHTVIPLSA PTLVPQDHYV RITGLYPTLN ISDDFSSNVA  900
NYQKVGIQKY STLQGPPPTG KSYFAIGLAL YYLSARIVYT ACSHAAVYTL CEKALKYFPI  960
DKCSRIIPAR ARVDCFDKFK VNLTLEQYVF CTVNALPDTT ADIVVFDEIS MTTNYDLSVV  1020
NARLCAKHYV YIGDSAQLPA PRTLLIKGTL EPEYFNSVCR FMKTIGPDMF LGTCRRCPSE  1080
IVDTVSALVY DNRL                                                   1094

SEQ ID NO: 7            moltype = AA  length = 1094
FEATURE                 Location/Qualifiers
REGION                  1..1094
                        note = Additional optimized region 1 polypeptide (region 1
                        EG-2.2)
source                  1..1094
                        mol_type = protein
                        organism = synthetic construct
SEQUENCE: 7
NCLDDRCVLH CANFNVLFST VFPFTSFGPL VRKICVDGVP FVVSTGHHFR ELGVVYNQDV  60
NLHSFRLSFK ELLLYAADPA MHVASGNLLL DRRTTCFSVA ALTNNFAFQT VKPGNFNKDF  120
YDFALSKGFF KEGSPVELKH FFFVQDGNAA ISDYEYYRYN LPTMFDIRQL LFVFEVVDKY  180
FDCYDGGCIN ANQVTVNNLD KSAGPPFNKW GKARLYYESM SYEDQDVLFA YTKRNVTPTI  240
TQMNLKYAIS VKNRARTVAG VSICSTITNR QFHQKLLKSI AATGGATVVI GTSKFYGGWH  300
NILKTVYSDV ENPYLMGWDY PKCDRAMPNM LRIVASLVKA RKHTMCCSLS HRFYRLTNEC  360
AQVLSEMVIC GGSLYVKPGG TSSGDATTAY ANSVFNIFQA VTANVNTLLS TDGNKIADNY  420
VRNLQHRLYG CLYRNRDVYT DFVNEFYTYL RKHFSMIILS AAAVVCFNST YVSQGLVASI  480
RNFKSVLYYQ NNVFMSEVKC WTETDLIKGP HEFCSQHTIL VKQGDDYVYF PYPDPSRILG  540
AGCFVDDVVK TDGTLMVERF VSLAIDAYPF TKHPNQEYAV VFHLYLQYIK KLHDELTGHI  600
LDMYSVMLIN DNTSRYWESE FYEAMYTSHT VLQAVGSCVL CNSQTLLRCG ACIRKPFLCC  660
KCCYDHIIST SHKLVFSVNP YVCNVPGCDV TDVTQLCLGG MSYYCKPHKP PISFPLCVNG  720
QVFGLYKNTC AGSDNVTDFN AISTCDWTNA GDYILANACT ERLKLFAAEM LKATEETFKL  780
SYGVATVREV LSDKELHLSW EVGRPRPPLN RNYVFTGYRL TKNSKVQTGE YTFEKGYYGD  840
AVVYRGITTY KLNVGDYFLL TSHTVMPLSA PILVPQEHYV RIIGLYPTLN ISYEFSSNVA  900
NYQKVGMQRY STLQGPPPTG KSHFAIGLSL YYPSARIMYT ACSHAAVDAL CDKALKYPLI  960
DKCSRIIPAR ALVECFDKFK LNSTLEQYVF CTVNALPETT VDIVVFDEIS MTTNYDLSVV  1020
NVRLRAKHYV YVGDPAQLPA PRTLLTKGIL EPEYFNSVCR LIKTIGPDMF LRTCRRCPAE  1080
IVDTLSALVY DNKL                                                   1094

SEQ ID NO: 8            moltype = AA  length = 1094
FEATURE                 Location/Qualifiers
REGION                  1..1094
                        note = Sarbecovirus optimized region 1 polypeptide (region
                        1 SARBECO-EG-2.1)
source                  1..1094
                        mol_type = protein
                        organism = synthetic construct
SEQUENCE: 8
NCLDDRCILH CANFNVLFST VFPLTSFGPL VRKIFVDGVP FVVSTGYHFR ELGVVHNQDV  60
NIHSSRLSFK ELLVYAADPA MHAASGNLLL DKRTTCFSVA ALTNNVSFQT VKPGNFNKDF  120
YDFAVSKGFF KEGSSVELKH FFFAQDGNAA ISDYDYYRYN LPTMCDIRQL LFVVEVVDKY  180
FDCYDGGCIN ANQVIVNNLD KSAGPPFNKW GKARLYYDSM SYEDQDALFV YTKRNVLPTI  240
TQMNLKYAIS AKNRARTVAG VSICSTMTNR QFHQKLLKSI AATRGATVVI GTSKFYGGWN  300
NMLKTVYSDV ETPHLMGWDY PKCDRAMPNM LRIMASLVLA RKHSTCCNLS HRFYRLANEC  360
AQVLSEMVMC GGSLYVKPGG TSSGDATTAY ANSVFNICQA VTANVNALLS TDGNKIGDKY  420
IRNLQHRLYE CLYRNRDVDH EFVDEFYAYL RKHFSMMILS AAAVVCYNSN YAAQGLVASI  480
KNFKAVLYYQ NNVFMSEAKC WTETDLTRGP HEFCSQHTML VKQGDDYVYL PYPDPSRILG  540
```

```
AGCFVDDIVK TDGTLMIERF VSLAIDAYPL TKHPNQEYAD VFHLYLQYIR KLHDELTGHM    600
LDMYSVMLTN DSTSRYWEPE FYEAMYTPHT ILQAVGACVL CNSQTSLRCG ACIRRPFLCC    660
KCCYDHVIST SHKLVLSVNP YVCNATGCDV TDVTQLYLGG MSYYCKAHKP PISFPLCANG    720
QVFGLYKNTC VGSDNVTDFN AIATCDWTNA GDYILANTCT ERLKLFAAET LKATEETFKL    780
SYGIATVREV LSDRELYLSW EVGKPRPPLN RNYVFTGYRV TKNSKTQIGE YTFEKGDYGD    840
AVVYRGTTTY KLNVGDYFVL TSHTVMPLSA PTLVPQEHYV RITGLYPTLN ISEEFSSNVA    900
NYQKIGMQKY STLQGPPGTG KSHFAIGLAL YYPSARIVYT ACSHAAVDAL CEKALKYLPI    960
DKCSRIIPAR ARVECFDKFK VNSTLEQYVF CTVNALPETT ADIVVFDEIS MATNYDLSVV   1020
NARLRAKHYV YIGDPAQLPA PRTLLTKGTL EPEYFNSVCR LMKTIGPDMF LGTCRRCPAE   1080
IVDTVSALVY DNKL                                                     1094

SEQ ID NO: 9            moltype = AA  length = 1094
FEATURE                 Location/Qualifiers
REGION                  1..1094
                        note = Additional sarbecovirus optimized region 1
                          polypeptide (region 1 SARBECO-EG-2.2):
source                  1..1094
                        mol_type = protein
                        organism = synthetic construct
SEQUENCE: 9
NCLDDRCILH CANFNVLFST VFPPTSFGPL VRKIFVDGVP FVVSTGYHFR ELGVVHNQDV     60
NIHSSRLSFK ELLVYAADPA MHAASGNLLL DKRTTCFSVA ALTNSVAFQT VKPGNFNKDF    120
YDFAVSKGFF KEGSSVELKH FFFAQDGNAA ISDYDYYRYN LPTMCDIRQL LFVVEVVDKY    180
FDCYDGGCIN ANQVIVNNLD KSAGFPFNKW GKARLYYDSM SYEDQDALFA YTKRNVLPTI    240
TQMNLKYAIS AKNRARTVAG VSICSTMTNR QFHQKLLKSI AATRGATVVI GTSKFYGGWN    300
NMLKTVYSDV ESPHLMGWDY PKCDRAMPNM LRIMASLVLA RKHNTCCNLS HRFYRLANEC    360
AQVLSEMVMC GGSLYVKPGG TSSGDATTAY ANSVFNICQA VTANVNALLS TDGNKIADKY    420
VRNLQHRLYE CLYRNRDVDT DFVNEFYAYL RKHFSMMILS AAAVVCYNSN YAAQGLVASI    480
KNFKSVLYYQ NNVFMSEAKC WTETDLTRGP HEFCSQHTML VKQGDDYVYL PYPDPSRILG    540
AGCFVDDIVK TDGTLMIERF VSLAIDAYPL TKHPNQEYAD VFHLYLQYIR KLHDELTGHM    600
LDMYSVMLTN DNTSRYWEPE FYEAMYTPHT VLQAVGACVL CNSQTSLRCG ACIRRPFLCC    660
KCCYDHVIST SHKLVLSVNP YVCNAPGCDV TDVTQLYLGG MSYYCKLHKP PISFPLCANG    720
QVFGLYKNTC VGSDNVTDFN AIATCDWTNA GDYILANTCT ERLKLFAAET LKATEETFKL    780
SYGIATVREV LSDRELHLSW EVGKPRPPLN RNYVFTGYRV TKNSKVQIGE YTFEKGDYGD    840
AVVYRGTTTY KLNVGDYFVL TSHTVMPLSA PTLVPQEHYV RITGLYPTLN ISDEFSSNVA    900
NYQKIGMQKY STLQGPPGTG KSHFAIGLAL YYPSARIVYT ACSHAAVDAL CEKALKYLPI    960
DKCSRIIPAR ARVECFDKFK VNSTLEQYVF CTVNALPETT ADIVVFDEIS MATNYDLSVV   1020
NARLRAKHYV YIGDPAQLPA PRTLLTKGTL EPEYFNSVCR LMKTIGPDMF LGTCRRCPAE   1080
IVDTVSALVY DNKL                                                     1094

SEQ ID NO: 10           moltype = AA  length = 540
FEATURE                 Location/Qualifiers
REGION                  1..540
                        note = Alternative SARS-CoV-2 nsp6-10 polypeptide (region 2)
source                  1..540
                        mol_type = protein
                        organism = synthetic construct
SEQUENCE: 10
GGKPCIKVAT VQSKMSDVKC TSVVLLSVLQ QLRVESSSKL WAQCVQLHND ILLAKDTTEA     60
FEKMVSLLSV LLSMQGAVDI NKLCEEMLDN RATLQAIASE FSSLPSYAAF ATAQEAYEQA    120
VANGDSEVVL KKLKKSLNVA KSEFDRDAAM QRKLEKMADQ AMTQMYKQAR SEDKRAKVTS    180
AMQTMLFTML RKLDNDALNN IINNARDGCV PLNIIPLTTA AKLMVVIPDY NTYKNTCDGT    240
TFTYASALWE IQQVVDADSK IVQLSEISMD NSPNLAWPLI VTALRANSAV KLQNNELSPV    300
ALRQMSCAAG TTQTACTDDN ALAYYNTTKG GRFVLALLSD LQDLKWARFP KSDGTGTIYT    360
ELEPPCRFVT DTPKGPKVKY LYFIKGLNNL NRGMVLGSLA ATVRLQAGNA TEVPANSTVL    420
SFCAFAVDAA KAYKDYLASG GQPITNCVKM LCTHTGTGQA ITVTPEANMD QESFGGASCC    480
LYCRCHIDHP NPKGFCDLKG KYVQIPTTCA NDPVGFTLKN TVCTVCGMWK GYGCSCDQLR    540

SEQ ID NO: 11           moltype = AA  length = 540
FEATURE                 Location/Qualifiers
REGION                  1..540
                        note = SARS-CoV-2 region 2 optimized polypeptide (region 2
                          SARS-CoV2-EG-2.1)
source                  1..540
                        mol_type = protein
                        organism = synthetic construct
SEQUENCE: 11
GGKPCVKVAT VQSKISDVKC TSVVLLLVLQ QLRVESLSKL WAQCVQLHND IILAKDTTEA     60
FGKMVSLLSV LLSMQRAVDI NKLCEEILDN RATLQSIASE FSSLSSYAAF ATAQEAYERA    120
VANGDSEVFL KKLKKSLNVA KSEFDCDAAM QRKLENMADQ AMTQMYKQVR SEDKRAKVTS    180
AMQIMLFTML RKFDNDALNN IVNNARDGCV PLNIIPFTTA AKLMVVISDY NTYKNTCDGI    240
TFTYASALWE IQHVVDADSK IVQFSEISMD NSSNLAWPLI VIALRANSAV KLQNNELSPV    300
VLRQMSCAAG TTQTACIDDN ALAYYNTIKG GRFVLALLSD LQDLKWARFP KSDGTGTVYT    360
ELEPPCGFVT DTPKGLKVKY LYFIRGLNNL NRGIVLGSLA ATVRLQAGKA TEVPANSIVL    420
SFCAFAIDAA KAYKDYLVSG GQPITNCVKM LCTHIGTGQA ITVIPEANMD QESFGGASCC    480
MYCRCHIDHP DPKGFCDLKG KYVQIPTICA NDPVGFILKN TVCTVCSMWK GYGCSCDQLC    540

SEQ ID NO: 12           moltype = AA  length = 540
FEATURE                 Location/Qualifiers
```

| | | |
|---|---|---|
| REGION | 1..540 | |
| | note = Additional SARS-CoV-2 optimized region 2 polypeptide (region 2 SARS-CoV2-EG-2.2) | |
| source | 1..540 | |
| | mol_type = protein | |
| | organism = synthetic construct | |

SEQUENCE: 12
```
GGKPCIKVAT VQSKTSDVKC TSVVLLSVFQ QLRVESSFKL WAQCVQLHND ILLARDTTEA  60
FEKMVSLLSV LFSMQGAVDI NKFCEEMLDN RAILQAIASE FSSLPSYAAL ATAQEAYEQA 120
VVNGDSEVVL KNLKKSLNVA KSEFDLDAAM QRKLEKMSDQ AMTQMYKQAK SEDKRAKVIS 180
AMQTMLFTMF RKLDNDALNN IIDNARDGCV PLNIIPLITA AKLMVVTPDY NTYKNMCDGT 240
TFIYASALWE IQQVVNADSK IVQLSEVSMD NSPNLAWPLV VTALRANSAI KLQNNELSPI 300
ALRQMSCAAG TIQTACTDDN ALVYYNTTKG GRFVFALLSD LQDLKWARFS KSDGTGTIYI 360
ELEPPCRFVT DTLKGPKVKY LYFIKRLNNL NRGMVLGSLA AIVRLQAGNA IEVPANSTVL 420
FFCAFAVDAS KAYKDYLASG GQPIINCVKM LCTHTGIGQA ITVTPEANME QESFGGASCC 480
LYCRCHIDHS NPKGFCDLKG RYVQIPTTCV NDPVGFTLKN TVCTICGMWK GYGCGCDQLR 540
```

| | | |
|---|---|---|
| SEQ ID NO: 13 | moltype = AA length = 540 | |
| FEATURE | Location/Qualifiers | |
| REGION | 1..540 | |
| | note = sarbecovirus region 2 optimized polypeptide (region 2 SARBECO-EG-2.1): | |
| source | 1..540 | |
| | mol_type = protein | |
| | organism = synthetic construct | |

SEQUENCE: 13
```
GGKPCIKVAT VQSKMSDVKC TSVVLLSVLQ QLRVESSSKL WAQCVQLHND ILLAKDTTEA  60
FEKMVSLLSV LLSMQGAVDI NRLCEEMLDN RATLQAIASE FSSLPSYAAY ATAQEAYEQA 120
VSNGDSEVVL KKLKKSLNVA KSEFDHDAAM QRKLEKMADQ AMTQMYKQAR SEDKRAKVTS 180
AMQTMLFTML RKLDNDALNN IINNARDGCV PLNIIPLTTA AKLMVVVPDY GTYKNTCDGN 240
TFTYASALWE IQQVVDADSK IVQLSEINMD NSPNLAWPLI VTALRANSAV KLQNNELSPV 300
ALRQMSCAAG TTQTACNEDN ALAYYNNSKG GRFVLALLSD HQDLKWARFP KSDGTGTIYT 360
ELEPPCRFVT DTPKGPKVKY LYFIKGLNNL NRGMVLGSLA ATVRLQAGNA TEVPANSTVL 420
SFCAFAVDPA KAYKDYLSSG GQPITNCVKM LCTHTGTGQA ITVTPEANMD QESFGGASCC 480
LYCRCHIDHP NPKGYCELKG KYVQIPTTCA NDPVGFTLRN TVCTVCGMWK GYGCSCDQLR 540
```

| | | |
|---|---|---|
| SEQ ID NO: 14 | moltype = AA length = 540 | |
| FEATURE | Location/Qualifiers | |
| REGION | 1..540 | |
| | note = Additional sarbecovirus region 2 optimized polypeptide (region 2 SARBECO-EG-2.2) | |
| source | 1..540 | |
| | mol_type = protein | |
| | organism = synthetic construct | |

SEQUENCE: 14
```
GGKPCIKVAT VQSKMSDVKC TSVVLLSVLQ QLRVESSSKL WAQCVQLHND ILLAKDTTEA  60
FEKMVSLLSV LLSMQGAVDI NRLCEEMLDN RATLQAIASE FSSLPSYAAF ATAQEAYEQA 120
VANGDSEVVL KKLKKSLNVA KSEFDRDAAM QRKLEKMADQ AMTQMYKQAR SEDKRAKVTS 180
AMQTMLFTML RKLDNDALNN IINNARDGCV PLNIIPLTTA AKLMVVVPDY NTYKNTCEGS 240
TFTYASALWE IQQVVDADSK IVPLSEINMD NSQNLAWPLI VTALRANSAV KLQNNELSPV 300
ALRQMSCAAG TTQTACTDDN ALAYYNTSKG GRFVLALLSD LQDLKWARFP KSDGTGTIYT 360
ELEPPCRFVT DTPKGPKVKY LYFIKGLNNL NRGMVLGSLA ATVRLQAGNA TEVPANSTVL 420
SFCAFAVDAS KAYRDYLASG GQPITNCVKM LCTHTGTGQA ITVTPEANMD QESFGGASCC 480
LYCRCHIDHP NPKGFCDLKG KYVQIPTTCA NDPVGFTLRN TVCTVCGMWK GYGCSCDQLR 540
```

| | | |
|---|---|---|
| SEQ ID NO: 15 | moltype = DNA length = 3288 | |
| FEATURE | Location/Qualifiers | |
| misc_feature | 1..3288 | |
| | note = Nucleic acid encoding modified conserved region SARS-CoV-2 polypeptide spanning RNA-dependent RNA polymerase and helicase proteins (region 1) | |
| source | 1..3288 | |
| | mol_type = other DNA | |
| | organism = synthetic construct | |

SEQUENCE: 15
```
atgaactgcc tggacgaccg ctgcatcctg cactgcgcca acttcaacgt gctgttctcc  60
accgtgttcc cccccacctc cttcggcccc ctggtgcgca agatcttcgt ggacggcgtg 120
cccttcgtgg tgtccaccgg ctaccacttc cgcgagctgg cgtggtgca caaccaggac 180
gtgaactgc actcctcccg cctgtccttc aaggagctgc tggtgtacgc cgccgacccc 240
gccatgcacg ccgcctccgg caacctgctg ctggacaagg caccaccctg cttctccgtg 300
gccgccctga ccaacaacgt ggccttccag accgtgaagc ccgcaactt caacaaggac 360
ttctacgact cgccgtgtc caagggcttc ttcaaggagg ctcctccgt ggagctgaag 420
cacttcttct tcgcccagga cggcaacgcc gccatcccg actacgacta ctaccgctac 480
aacccacatg tgcga catccgccag ctgctgttcg tggtggacaa 540
tacttcgact gctacgacgg cggctgcatc aacgccaacc aggtgatcgt gaacaacctg 600
gacaagtccg ccggcttccc cttcaacaag tggggcaagg cccgcctgta ctacgactcc 660
atgtcctacg aggaccagga cgccctgttc gcctacacca gcgcaacgt gatccccacc 720
atcacccaga tgaacctgaa gtacgccatc ccgccaaga ccgcgcccg caccgtggcc 780
ggcgtgtcca tctgctccac catgaccaac cgccagttca ccagaagct gctgaagtcc 840
```

```
atcgccgcca cccgcggcgc caccgtggtg atcggcacct ccaagttcta cggcggctgg    900
cacaacatgc tgaagaccgt gtactccgac gtggagaacc cccacctgat gggctgggac    960
tacccccaagt gcgaccgcgc catgcccaac atgctgcgca tcatggcctc cctggtgctg   1020
gcccgcaagc acaccacctg ctgctccctg tccaccgct tctaccgcct ggccaacgag    1080
tgcgccagg tgctgtccga gatggtgatg tgcggcgct ccctgtacgt gaagcccgac     1140
ggcacctcct ccggcgacgc caccaccgcc tacgccaact ccgtgttcaa catctgccag   1200
gccgtgaccg ccaacgtgaa cgccctgctg tccaccgacg gcaacaagat cgccgacaag   1260
tacgtgcgca acctgcagca ccgcctgtac gagtgcctgt accgcaaccg cgacgtggac   1320
accgacttcg tgaacgagtt ctacgcctac ctgcgcaagc acttctccat gatgatcctg   1380
tccgccgccg ccgtggtgtg cttcaactcc acctacgcct cccagggcct ggtggcctcc   1440
atcaagaact tcaagtccgt gctgtactac cagaacaacg tgttcatgtc cgaggccaag   1500
tgctggaccg agaccgacct gaccaagggc cccacgagt ctgctcccca gcacaccatg    1560
ctggtgaagc agggcgacga ctacgtgtac ctgccctacc ccgacccctc ccgcatcctg   1620
ggcgccggct gcttcgtgga cgacatcgtg aagaccgacg gcaccctgat gatcgagcgg   1680
ttcgtgtccc tggccatcga cgcctacccc ctgaccaagc accccaacca ggagtacgcc   1740
gacgtgttcc acctgtacct gcagtacatc cgcaagctgc acgacgagct gaccggccac   1800
atgctggaca tgtactccgt gatgctgacc aacgacaaca cctcccgcta ctgggagccc   1860
gagttctacg aggccatgta cacccccac accgtgctgc acccctgcgtg cgcctgcgtg   1920
ctgtgcaact cccagacctc cctgcgctgc ggcgcctgca tccgccgccc cttcctgtgc   1980
tgcaagtgct gctacgacca cgtgatctcc acctcccaca agctggtgct gtccgtgaac   2040
ccctacgtgt gcaacgcccc cggctgcgac gtgaccgacg tgacccagct gtacctgggc   2100
ggcatgtcct actactgcaa gtcccacaag ccccccatct ccttcccctct ctgcgccaac   2160
ggccaggtgt tcggcctgta caagaacacc tgcgtgggcc ccgacaacgt gaccgacttc   2220
aacgccatcg ccacctgcga ctggaccaac gccggcgact acatcctggc caacacctgc   2280
accgagcgcc tgaagctgtt cgccgccgag accctgaagg ccaccgagga gacccttcaag   2340
ctgtcctacg gcatcgccac cgtgcgcgag gtgctgtccg accgcgagct gcacctgtcc   2400
tgggaggtgg gcaagcccg cccccccctg aaccgcaact acgtgttcac cggctaccgc   2460
gtgaccaaga actccaaggt gcagatcggc gagtacacct tcgagaaggg cgactacggc   2520
gacgccgtgg tgtaccgcgg caccaccacc tacaagctga acgtgggcga ctacttcgtg   2580
ctgacctccc acaccgtgat gccccctgtcc gccccccctac tggtgcccca ggagcactac   2640
gtgcgcatca ccggcctgta ccccaccctg aacatctccg acgagttctc ctccaacgtg   2700
gccaactacc agaaggtggg catgcagaag tactccaccc tgcagggccc cccggcacc    2760
ggcaagtccc acttcgccat cggcctggcc ctgtactacc cctccgcccg catcgtgtac   2820
accgcctgct cccacgccgc cgtggacgcc ctgtgcgaga aggccctgaa gtacctgccc   2880
atcgacaagt gctcccgcat catccccgcc cgcgcccgcg tggagtgctt cgacaagttc   2940
aaggtgaact ccaccctgga gcagtacgtg ttctgccacg tgaacgccct gcccgagacc   3000
accgccgaca tcgtggtgtt cgacgagatc tccatggcca ccaactacga cctgtccgtg   3060
gtgaacgccc gcctgcgcgc caagcactac gtgtacatcg gcgaccccgc ccagctgccc   3120
gccccccgcc ccctgctgac caagggcacc ctggagcccg agtactttcaa ctccgtgtgc   3180
cgcctgatga agaccatcgg ccccgacatg ttcctgggca cctgccgccg ctgccccgcc   3240
gagatcgtgg acaccgtgtc cgccctggtg tacgacaaca gctgtaa                 3288

SEQ ID NO: 16           moltype = DNA  length = 609
FEATURE                 Location/Qualifiers
misc_feature            1..609
                        note = Nucleic acid encoding conserved region SARS-CoV-2
                         polypeptide from helicase
source                  1..609
                        mol_type = other DNA
                        organism = synthetic construct
SEQUENCE: 16
atggagttct cctccaacgt ggccaactac cagaaggtgg gcatgcagaa gtactccacc     60
ctgcagggcc ccccggcac cggcaagtcc cacttcgcca tcggcctggcc ctgtactac    120
ccctccgccc gcatcgtgta caccgcctgc tcccacgccg ccgtgacgc cctgtgcgag   180
aaggccctga agtacctgcc catcgacaag tgctcccgca tcatccccgc ccgcgcccgc   240
gtggagtgct tcgacaagtt caaggtgaac tccaccctgg agcagtacg gttctgcacc    300
gtgaacgccc tgcccgagac caccgccgac atcgtggtgt tcgacgagat ctccatggcc   360
accaactacg acctgtccgt ggtgaacgcc cgcctgcgcg ccaagcacta cgtgtacatc   420
ggcgaccccg cccagctgcc cgccccccgc ccctgctga ccaagggcac cctggagccc    480
gagtacttca actccgtgtg ccgcctgatg aagaccatcg gccccgacat gttcctgggc   540
acctgccgcc gctgccccgc cgagatcgtg gacaccgtgt ccgccctggt gtacgacaac   600
aagctgtaa                                                             609

SEQ ID NO: 17           moltype = DNA  length = 618
FEATURE                 Location/Qualifiers
misc_feature            1..618
                        note = Nucleic acid encoding conserved region SARS-CoV-2
                         polypeptide from RNA-dependent RNA polymerase
source                  1..618
                        mol_type = other DNA
                        organism = synthetic construct
SEQUENCE: 17
atgttccaga ccgtgaagcc cggcaacttc aacaaggact ctacgactt cgccgtgtcc      60
aagggcttct tcaaggaggg ctcctccgtg gagctccgaa gc acttcttctt cgcccaggac   120
ggcaacgccg ccatctccga ctactccgac taccgctaca acctgcccac catgtgcgac   180
atccgccagc tgctgttcgt ggtggaggtg gtggacaagt acttcgactg ctacgacggc   240
ggctgcatca acgccaacca ggtgatcgtg aacaacctgg acaagtccgc cggcttcccc   300
ttcaacaagt ggggcaaggc ccgcctgtac tacgactcca tgtcctacga ggaccaggac   360
gccctgttcg cctacaccaa gcgcaacgtg atccccacca tcacccagat gaacctgaag   420
```

```
tacgccatct  ccgccaagaa  ccgcgcccgc  accgtggccg  gcgtgtccat  ctgctccacc    480
atgaccaacc  gccagttcca  ccagaagctg  ctgaagtcca  tcgccgccac  ccgcggcgcc    540
accgtggtga  tcggcacctc  caagttctac  ggcggctggc  acaacatgct  gaagaccgtg    600
tactccgacg  tggagtaa                                                     618

SEQ ID NO: 18           moltype = AA  length = 1642
FEATURE                 Location/Qualifiers
REGION                  1..1642
                        note = COVconsv amino acid sequence
source                  1..1642
                        mol_type = protein
                        organism = synthetic construct
SEQUENCE: 18
MNCLDDRCIL  HCANFNVLFS  TVFPPTSFGP  LVRKIFVDGV  PFVVSTGYHF  RELGVVHNQD     60
VNLHSSRLSF  KELLVYAADP  AMHAASGNLL  LDKRTTCFSV  AALTNNVAFQ  TVKPGNFNKD    120
FYDFAVSKGF  FKEGSSVELK  HFFFAQDGNA  AISDYDYYRY  NLPTMCDIRQ  LLFVVEVVDK    180
YFDCYDGGCI  NANQVIVNNL  DKSAGFPFNK  WGKARLYYDS  MSYEDQDALF  AYTKRNVIPT    240
ITQMNLKYAI  SAKNRARTVA  GVSICSTMTN  RQFHQKLLKS  IAATRGATVV  IGTSKFYGGW    300
HNMLKTVYSD  VENPHLMGWD  YPKCDRAMPN  MLRIMASLVL  ARKHTTCCSL  SHRFYRLANE    360
CAQVLSEMVM  CGGSLYVKPG  GTSSGDATTA  YANSVFNICQ  AVTANVNALL  STDGNKIADK    420
YVRNLQHRLY  ECLYRNRDVD  TDFVNEFYAY  LRKHFSMMIL  SAAAVVCFNS  TYASQGLVAS    480
IKNFKSVLYY  QNNVFMSEAK  CWTETDLTKG  PHEFCSQHTM  LVKQGDDYVY  LPYPDPSRIL    540
GAGCFVDDIV  KTDGTLMIER  FVSLAIDAYP  LTKHPNQEYA  DVFHLYLQYI  RKLHDELTGH    600
MLDMYSVMLT  NDNTSRYWEP  EFYEAMYTPH  TVLQAVGACV  LCNSQTSLRC  GACIRRPFLC    660
CKCCYDHVIS  TSHKLVLSVN  PYVCNAPGCD  VTDVTQLYLG  GMSYYCKSHK  PPISFPLCAN    720
GQVFGLYKNT  CVGSDNVTDF  NAIATCDWTN  AGDYILANTC  TERLKLFAAE  TLKATEETFK    780
LSYGIATVRE  VLSDRELHLS  WEVGKPRPPL  NRNYVFTGYR  VTKNSKVQIG  EYTFEKGDYG    840
DAVVYRGTTT  YKLNVGDYFV  LTSHTVMPLS  APTLVPQEHY  VRITGLYPTL  NISDEFSSNV    900
ANYQKVGMQK  YSTLQGPPGT  GKSHFAIGLA  LYYPSARIVY  TACSHAAVDA  LCEKALKYLP    960
IDKCSRIIPA  RARVECFDKF  KVNSTLEQYV  FCTVNALPET  TADIVVFDEI  SMATNYDLSV   1020
VNARLRAKHY  VYIGDPAQLP  APRTLLTKGT  LEPEYFNSVC  RLMKTIGPDM  FLGTCRRCPA   1080
EIVDTVSALV  YDNKLGGKPC  IKVATVQSKM  SDVKCTSVVL  LSVLQQLRVE  SSSKLWAQCV   1140
QLHNDILLAK  DTTEAFEKMV  SLVLLSMQGA  VDINKLCEEM  LDNRATLQAI  ASEFSSLPSY   1200
AAFATAQEAY  EQAVANGDSE  VVLKKLKKSL  NVAKSEFDRD  AAMQRKLEKM  ADQAMTQMYK   1260
QARSEDKRAK  VTSAMQTMLF  TMLRKLDNDA  LNNIINNARD  GCVPLNIIPL  TTAAKLMVVI   1320
PDYNTYKNTC  DGTTFTYASA  LWEIQQVVDA  DSKIVQLSEI  SMDNSPNLAW  PLIVTALRAN   1380
SAVKLQNNEL  SPVALRQMSC  AAGTTQTACT  DDNALAYYNT  TKGGRFVLAL  LSDLQDLKWA   1440
RFPKSDGTGT  IYTELEPPCR  FVTDTPKGPK  VKYLYFIKGL  NNLNRGMVLG  SLAATVRLQA   1500
GNATEVPANS  TVLSFCAFAV  DAAKAYKDYL  ASGGQPITNC  VKMLCTHTGT  GQAITVTPEA   1560
NMDQESFGGA  SCCLYCRCHI  DHPNPKGFCD  LKGKYVQIPT  TCANDPVGFT  LKNTVCTVCG   1620
MWKGYGCSCD  QLRIPNPLLG  LD                                              1642
```